United States Patent
Zhao et al.

(10) Patent No.: US 10,818,849 B2
(45) Date of Patent: Oct. 27, 2020

(54) ELECTRON ACCEPTORS BASED ON ALPHA-POSITION SUBSTITUTED PDI FOR OPV SOLAR CELLS

(71) Applicant: The University of Chicago, Chicago, IL (US)

(72) Inventors: Donglin Zhao, Hyougo (JP); Qinghe Wu, Chicago, IL (US); Luping Yu, Chicago, IL (US); Zhengxu Cai, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 0 days.

(21) Appl. No.: 16/067,501

(22) PCT Filed: Dec. 29, 2016

(86) PCT No.: PCT/US2016/069356
§ 371 (c)(1),
(2) Date: Jun. 29, 2018

(87) PCT Pub. No.: WO2017/117477
PCT Pub. Date: Jul. 6, 2017

(65) Prior Publication Data
US 2019/0044074 A1    Feb. 7, 2019

Related U.S. Application Data

(60) Provisional application No. 62/319,990, filed on Apr. 8, 2016, provisional application No. 62/272,278, filed on Dec. 29, 2015.

(51) Int. Cl.
*H01L 51/00* (2006.01)
*C09B 5/62* (2006.01)
(Continued)

(52) U.S. Cl.
CPC ........ *H01L 51/0072* (2013.01); *C07D 519/00* (2013.01); *C08G 61/123* (2013.01); *C08G 61/126* (2013.01); *C09B 3/14* (2013.01); *C09B 5/62* (2013.01); *C09B 57/001* (2013.01); *C09B 69/008* (2013.01); *C09B 69/102* (2013.01);
(Continued)

(58) Field of Classification Search
CPC .................................................. H01L 51/0072
See application file for complete search history.

(56) References Cited

U.S. PATENT DOCUMENTS

| 7,183,418 B2 | 2/2007 | Heeney et al. |
| 7,332,223 B2 | 2/2008 | Sotzing et al. |

(Continued)

FOREIGN PATENT DOCUMENTS

| WO | WO 2008/011957 A1 | 1/2008 |
| WO | WO 2015/042609 A1 | 3/2015 |

OTHER PUBLICATIONS

Jiang et al. (Polym. Chem., 2013, 4, 4631-4638) (Year: 2013).*

(Continued)

*Primary Examiner* — Liam J Heincer
(74) *Attorney, Agent, or Firm* — Brinks Gilson & Lione; Yuezhong Feng

(57) ABSTRACT

The present disclosure relates to α-substituted perylene diimide (PDI) derivatives as small molecular and polymerized electron acceptors in organic photovoltaic cells.

23 Claims, 26 Drawing Sheets

The synthetic procedure of PDI-2Bpin and synthesis of αPPID, βPPID, αPBDT and βPBDT.

(51) Int. Cl.
- C09B 69/00 (2006.01)
- H01L 27/142 (2014.01)
- H01L 51/42 (2006.01)
- C09B 3/14 (2006.01)
- C09B 57/00 (2006.01)
- C07D 519/00 (2006.01)
- C08G 61/12 (2006.01)
- C09B 69/10 (2006.01)

(52) U.S. Cl.
CPC ........ *H01L 27/142* (2013.01); *H01L 51/0032* (2013.01); *H01L 51/0036* (2013.01); *H01L 51/0052* (2013.01); *H01L 51/0053* (2013.01); *H01L 51/0056* (2013.01); *H01L 51/0058* (2013.01); *H01L 51/0068* (2013.01); *H01L 51/0071* (2013.01); *H01L 51/0074* (2013.01); *H01L 51/0094* (2013.01); *H01L 51/42* (2013.01); *H01L 51/4253* (2013.01); *Y02E 10/549* (2013.01)

(56) References Cited

U.S. PATENT DOCUMENTS

| | | |
|---|---|---|
| 2005/0082525 A1 | 4/2005 | Heeney et al. |
| 2005/0209419 A1 | 9/2005 | Zahn et al. |
| 2008/0102559 A1 | 5/2008 | Ong et al. |
| 2008/0103286 A1 | 5/2008 | Ong et al. |
| 2009/0194167 A1 | 8/2009 | Brabec |
| 2010/0283047 A1* | 11/2010 | Facchetti ............... C08G 61/10 257/40 |
| 2011/0124822 A1* | 5/2011 | Yu ....................... H01L 51/0036 525/389 |
| 2011/0266529 A1* | 11/2011 | Zhao .................... B82Y 10/00 257/40 |
| 2014/0021448 A1* | 1/2014 | Polander ............. H01L 51/0072 257/40 |
| 2014/0145119 A1* | 5/2014 | Yu ....................... H01L 51/0036 252/500 |
| 2014/0230900 A1 | 8/2014 | Cull et al. |
| 2014/0231773 A1* | 8/2014 | Suraru .................. C09K 11/06 257/40 |
| 2015/0041726 A1* | 2/2015 | He ........................ C08G 75/06 252/500 |
| 2015/0105520 A1 | 4/2015 | Bao et al. |
| 2016/0233448 A1* | 8/2016 | Yang .................. H01L 51/4253 |
| 2017/0104162 A1* | 4/2017 | Rosselli ............. H01L 51/0055 |
| 2018/0057492 A1* | 3/2018 | Rosselli ............. C07D 471/06 |
| 2019/0044074 A1* | 2/2019 | Zhao .................. H01L 51/0072 |
| 2019/0211035 A1* | 7/2019 | Welch ................ H01L 51/0058 |

OTHER PUBLICATIONS

Harnett et al. (Chem. Sci., 2016, 7, 3543-3555) (Year: 2016).*
International Search Report for International Application No. PCT/US2009/044364, 2 pages (dated Aug. 27, 2009).
International Search Report for corresponding International Application No. PCT/US2016/069356, 4 pages (dated Apr. 28, 2017).
Liang, Y., et al., "Control in Energy Levels of Conjugated Polymers for Photovoltaic Application," *J. Phys. Chem. C*, 112(21):7866-7871 (2008).

* cited by examiner

The synthetic procedure of PDI-2Bpin and synthesis of αPPID, βPPID, αPBDT and βPBDT.

Synthesis procedure for Compounds 1, 2, 3, PID and PID-2Bpin

Synthesis procedure for Compound QH0267

Synthesis procedure for Compound QH0290

Synthesis procedure for Compound QH0311

Synthesis procedure for Polymer QH0327

The solution absorption spectra of PPID, PBDT, TPBDT and PPBDT.

Synthesis procedure for Compound QH0275

0.1mmol α-bromo PDI and 1.0mmol Cu were stirred 6.0ml DMSO at 100 °C overnight. Product was purified by column chromatography.

Synthesis protocol for QH0289, QH0290, QH02106, QH02111, and QH02136

Detailed procedure is same as described in synthesis of QH0290.

Synthesis protocol for QH0297, QH02120, QH02138, and QH02141

Detailed procedure is same as described in synthesis of QH0267.

Synthesis protocol for QH0311, QH0333, QH0306, QH0318 and QH03105

Detailed procedure is same as described in synthesis of QH0311.

A

JV curves of ternary OPV devices using QH0311;

B

EQE curves of ternary OPV devices using QH0311

Scheme 1. A-D-A molecules and their fused ring compounds.

Reaction Conditions: a). Pd$_2$(dba)$_3$, P(o-MePh)$_3$, b). FeCl$_3$

J-V curves of PTB7-Th/conjugated molecules devices.

a) PTB7-Th/3r and PTB7-Th/C3r;

b) PTB7-Th/5r, PTB7-Th/C5r and PTB7-Th/C5r-DIO;

c) PTB7-Th/9r and PTB7-Th/C9r;

d) Open circuit voltage (VOC) versus and lowest unoccupied molecular orbital energy (ELUMO) versus the backbone conjugation length of a series of A-D-A molecules.

External quantum efficiency (EQE) spectra of PTB7-Th/conjugated molecules devices.

a) PTB7-Th/3r and PTB7-Th/C3r;

b) PTB7-Th/5r and PTB7-Th/C5r;

c) PTB7-Th/9r and PTB7-Th/C9r.

General synthetic procedure for TPC, TPSi and TPSe

General synthetic procedure for βTPB6-C

ELECTRON ACCEPTORS BASED ON ALPHA-POSITION SUBSTITUTED PDI FOR OPV SOLAR CELLS

CROSS REFERENCE TO RELATED APPLICATIONS

This application is a 371 national phase of PCT/US2016/069356, filed Dec. 29, 2016, which claims the benefit under 35 U.S.C. § 119(e) of U.S. Provisional Patent Application No. 62/319,990, filed Apr. 8, 2016, and of U.S. Provisional Patent Application No. 62/272,278, filed Dec. 29, 2015, the disclosures of which are incorporated, in their entirety, by this reference.

FEDERALLY SPONSORED RESEARCH OF DEVELOPMENT

This invention was made with government support under grant numbers DMR0213745, DMR1263006, DE-SC0001059, and KC020301 awarded by The United States National Science Foundation and The United States Department of Energy. The government has certain rights in the invention.

BACKGROUND

1. Field

The present disclosure relates to α-substituted perylene diimide (PDI) derivatives as small molecular and polymerized electron acceptors in organic photovoltaic cells.

2. Background

Organic photovoltaic (OPV) solar cells have advanced to the current stage that faces two challenges. One challenge is to further increase the power conversion efficiency (PCE) of those cells. Currently, PCE values as high as >11% are disclosed in small devices. This value is encouraging, but not enough for significant commercial exploration. The significant achievement in high PCE values has been made possible in bulky heterojunction (BHJ) solar cells which utilize conjugated molecules or polymers as the donor and fullerene derivatives as the acceptor. The second challenge is the cost of materials. Both donor and acceptor OPV materials are rather expensive. Due to the variety of different donor polymers available, the cost for donor materials can be managed. Although the fullerene derivatives ($PC_{61}BM$, $PC_{71}BM$) have superior electron accepting properties, their drawbacks are also clear: high cost, limited visible light absorption and instability in morphology in blend film, which hinders their industrial application and further improvement in device performance.

Recently, intensive research interest has been devoted to explore new acceptors with electron-deficient unit (such as, diketopyrrolopyrrole, dicyanovinyl, naphthalene diimide, perylene diimide) to replace the fullerene derivatives. Among them, perylene diimide (PDI) is the most promising building motif to develop electron-deficient acceptors for OPV applications. The PDI exhibits several appealing properties: low cost, chemically robust, easy to be functionalized, suitable absorption range and strong electron deficiency. Due to the strong tendency of aggregation of the extended conjugated backbone of PDI, two strategies were adopted to reduce the strong π-stacking, to enhance the processibility of materials and form favorable BHJ domain. One is to disrupt the strong π-π interaction of PDI by introducing the torsion in the conjugated backbone, such as twisted PDI dimmers connected at N-position or bay-positions (1,6,7,12-positions). Another is to synthesize A-D-A (Acceptor-Donor-Acceptor) molecules with donor coupled to PDIs at the bay positions. Both approaches have been effective to generating non-fullerene electron acceptors that showed improved OPV performance comparing to single PDI molecules. Unfortunately, the functionalization at the bay-positions of PDI lead to the twist of the perylene core that has been demonstrated to disrupt the close π-stacking of π-surface and diminish the electron transporting in the bulky solid state, thus limiting the OPV performances.

Thus, a need exists for strategies to functionalize PDI without introducing torsion in the perylene core.

SUMMARY

The present disclosure relates to α-substituted perylene diimide (PDI) derivatives as small molecular and polymerized electron acceptors in organic photovoltaic cells.

In one embodiment, a molecular acceptor is represented by formula A:

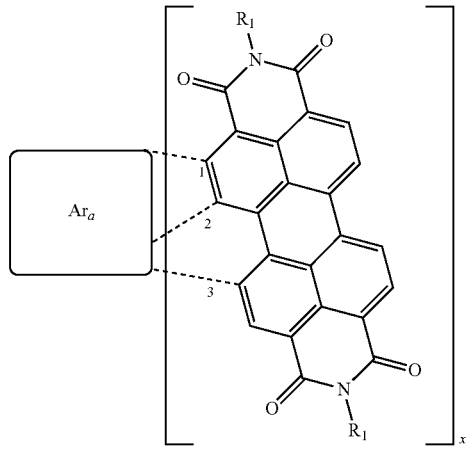

x is an integer selected from: 2, 4 and 6;

wherein when $Ar_a$ is bonded at 1, and x is 2, $Ar_a$ is selected from: a bond,

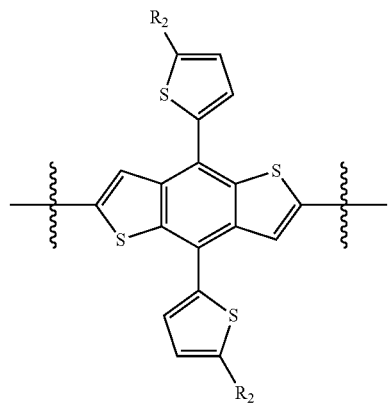

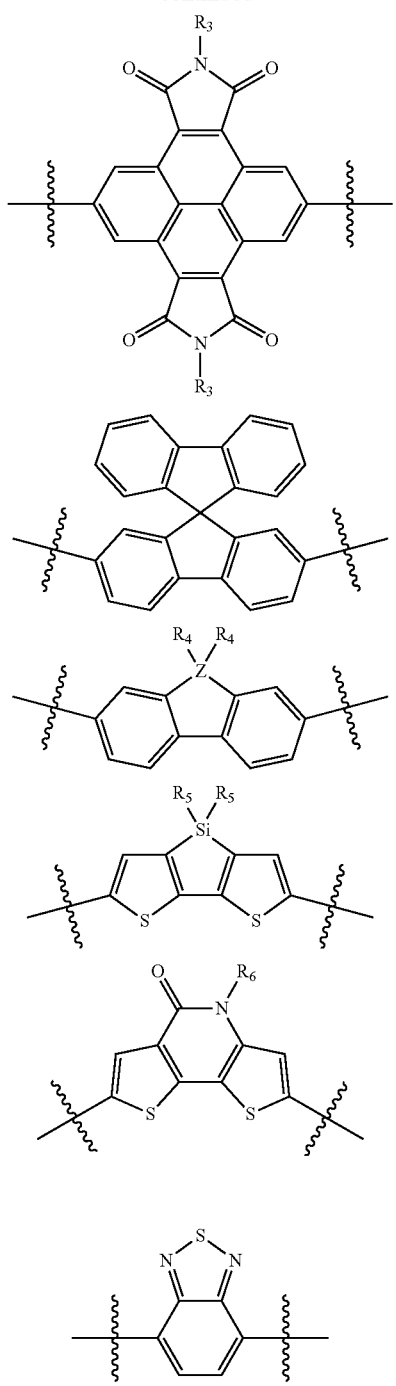
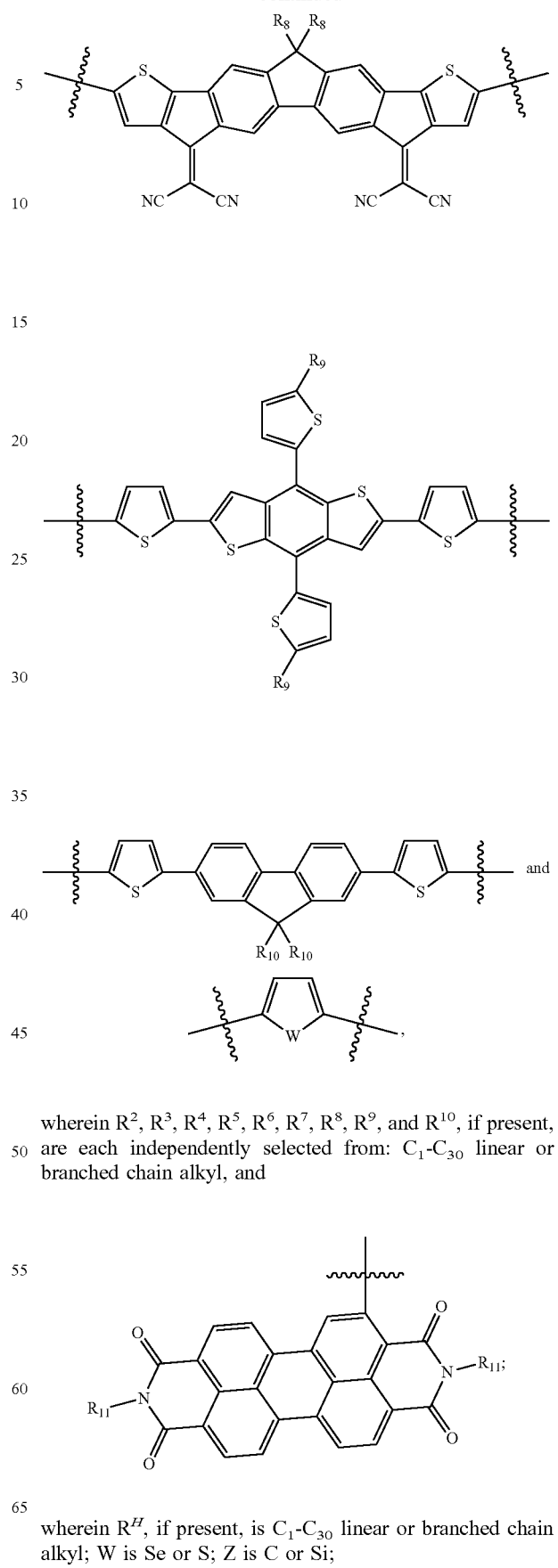
wherein $R^2$, $R^3$, $R^4$, $R^5$, $R^6$, $R^7$, $R^8$, $R^9$, and $R^{10}$, if present, are each independently selected from: $C_1$-$C_{30}$ linear or branched chain alkyl, and
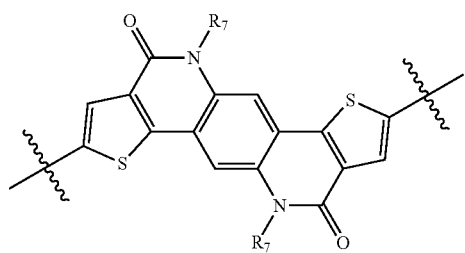
wherein $R^H$, if present, is $C_1$-$C_{30}$ linear or branched chain alkyl; W is Se or S; Z is C or Si;

or when Ar$_a$ is bonded at 1, and x is 4, Ar$_a$ is selected from:
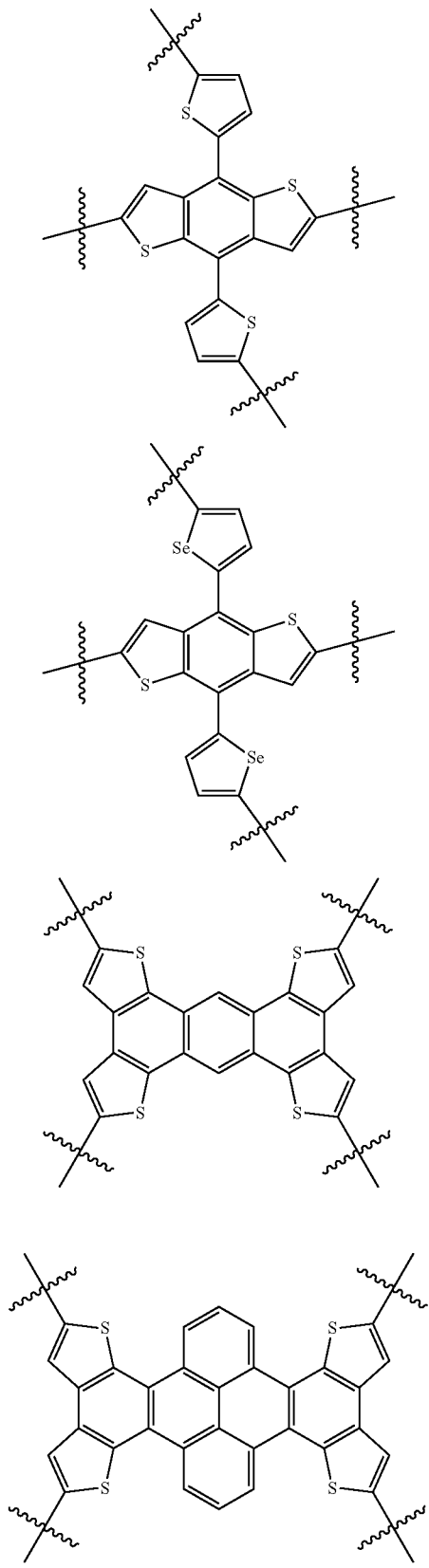
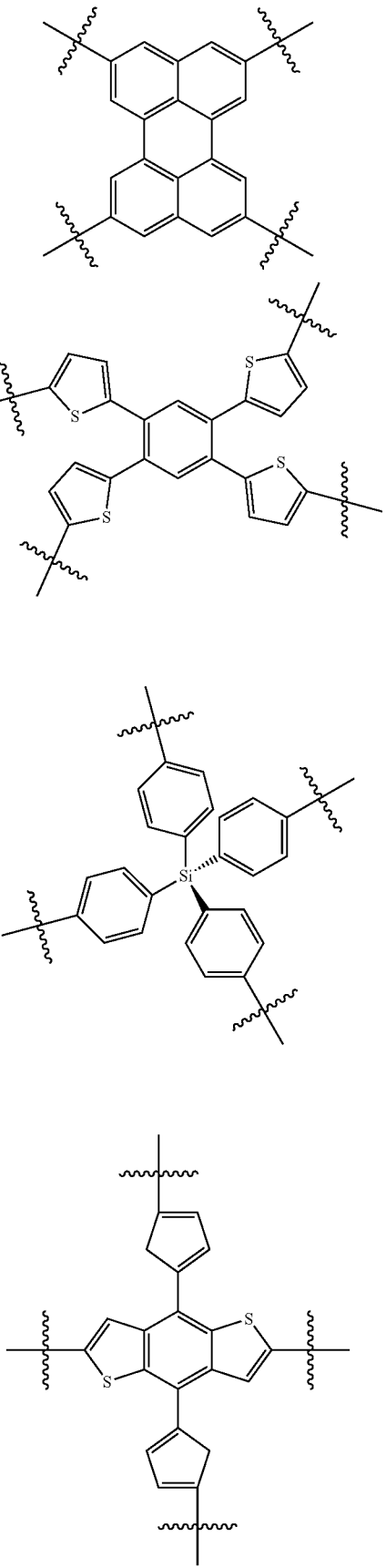

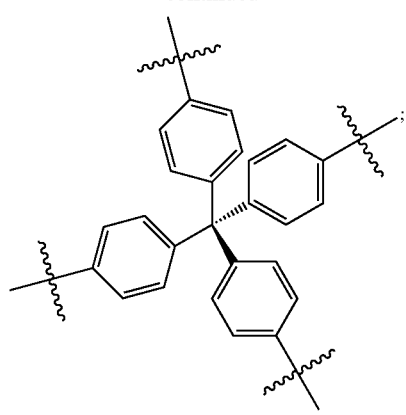
or when $Ar_a$ is bonded at 1, and x is 6, $Ar_a$ is selected from:
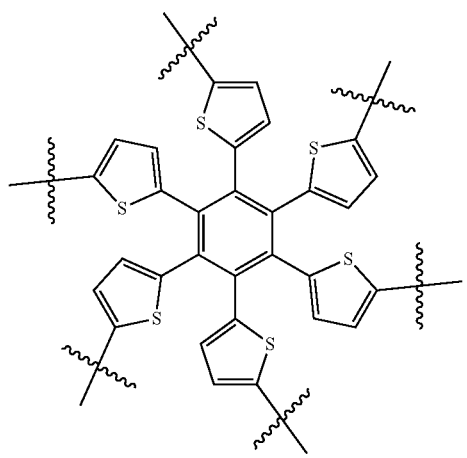
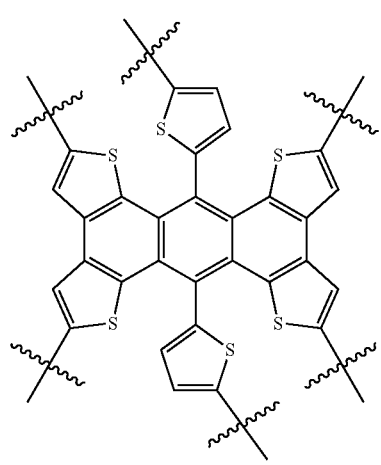
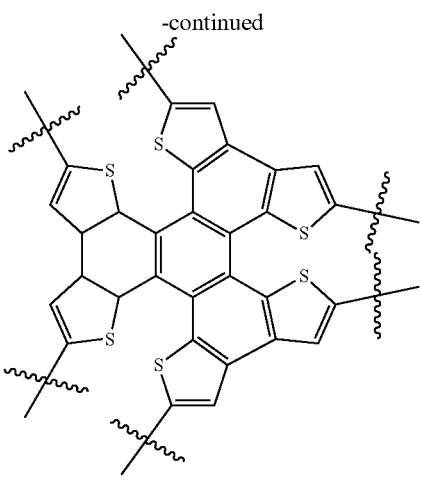
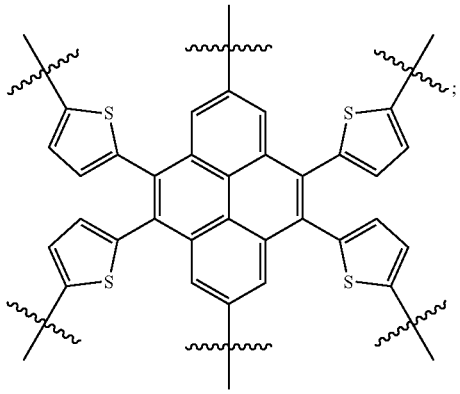
or when $Ar_a$ is bonded at 2 and 3 and x is 2, $Ar_a$ is selected from:
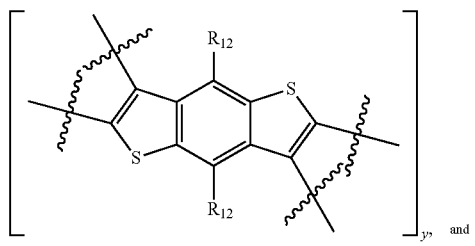
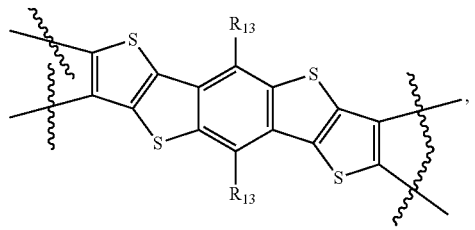
wherein $R^{12}$ and $R^{13}$, if present, are selected from: $C_1$-$C_{30}$ linear or branched chain alkyl; and
wherein y is an integer selected from 1 and 3;
or when $Ar_a$ is bonded at 2 and 3 and x is 4, $Ar_a$ is selected from:

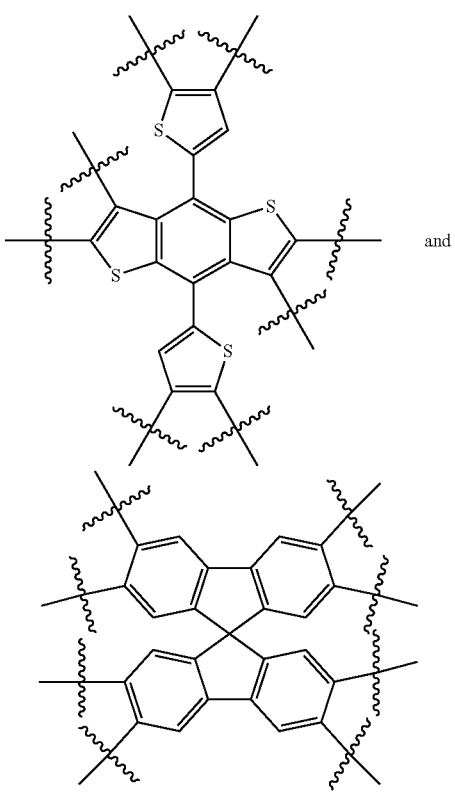

and

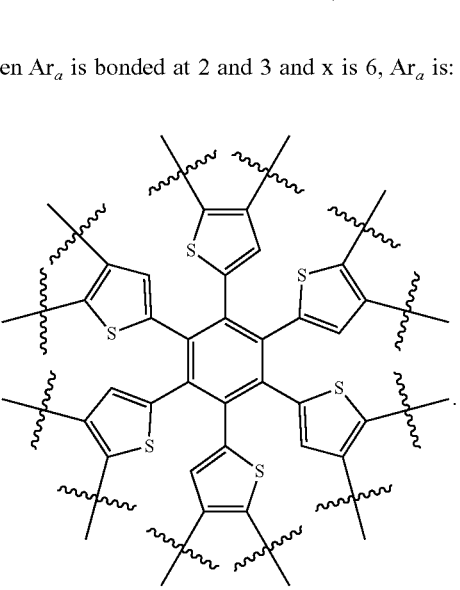

or when $Ar_a$ is bonded at 2 and 3 and x is 6, $Ar_a$ is:

In some embodiments, $R^1$ and at least one of $R^2$, $R^3$, $R^4$, $R^5$, $R^6$, $R^7$, $R^8$, $R^9$, $R^{10}$ and $R^{11}$ is the same. In some embodiments, $R^1$ and at least one of $R^2$, $R^3$, $R^4$, $R^5$, $R^6$, $R^7$, $R^8$, $R^9$, $R^{10}$ and $R^{11}$ is different. In some embodiments, $R^1$ and at least one of $R^2$, $R^3$, $R^4$, $R^5$, $R^6$, $R^7$, $R^8$, $R^9$, $R^{10}$ and $R^{11}$ is 2-ethylhexyl. In some embodiments, $R^1$ and at least one of $R^2$, $R^3$, $R^4$, $R^5$, $R^6$, $R^7$, $R^8$, $R^9$, $R^{10}$ and $R^{11}$ is 2-butyloctyl. In some embodiments, $R^1$ and at least one of $R^2$, $R^3$, $R^4$, $R^5$, $R^6$, $R^7$, $R^8$, $R^9$, $R^{10}$ and $R^{11}$ is 1-propylbutyl.

In some embodiments, the molecular acceptor is in a solar cell, an optical device, an electroluminescent device, a photovoltaic cell, a semiconducting cell, or photodiode.

DETAILED DESCRIPTION OF THE PREFERRED EMBODIMENTS

Figure 1:
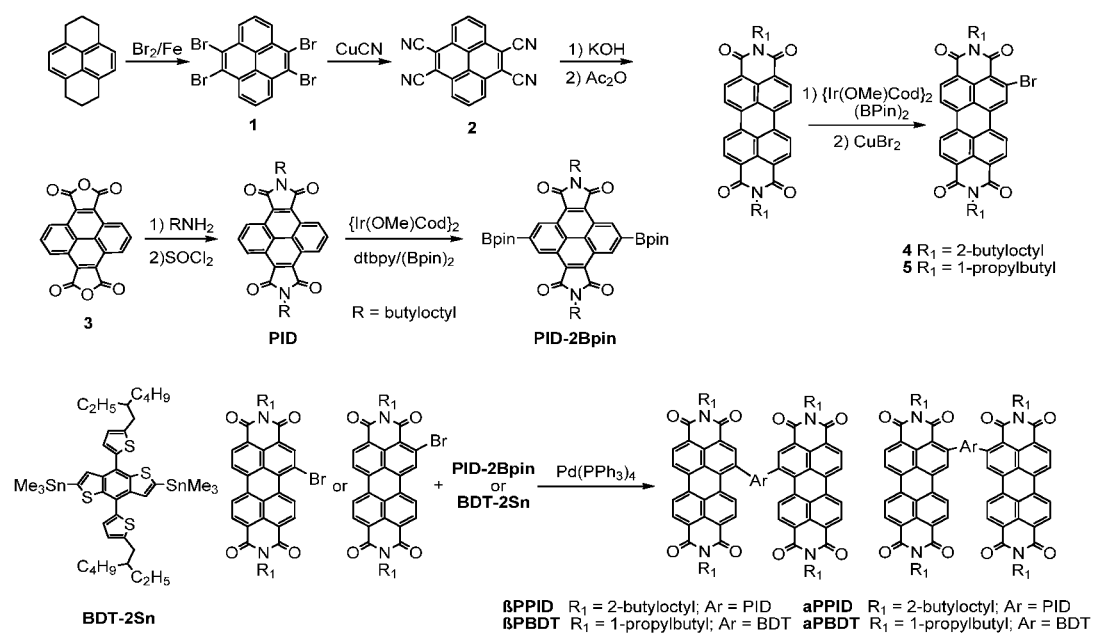
FIG. 1 depicts the synthetic procedure of PDI-2Bpin and synthesis of αPPID, βPPID, αPBDT and βPBDT.

Described herein are semiconducting small molecular electron acceptors, polymers, and their methods of synthesis and use. The acceptors and their polymers can be used in BHJ solar cells. The photovoltaic devices employing these electron deficient compounds as the acceptors and electron rich polymers as donors exhibit high solar conversion efficiency.

One embodiment described herein is a perylene diimide derivative functionalized at the ortho-position and used as an electron acceptor in non-fullerene organic photovoltaic cells. The semi-conducting small molecular electron acceptor may be conjugated or polymerized in photovoltaic cells. Photovoltaic devices employing these electron deficient compounds as the acceptors and electron rich polymers as donors exhibit high solar conversion efficiency.

In one embodiment, a molecular acceptor is represented by formula A:

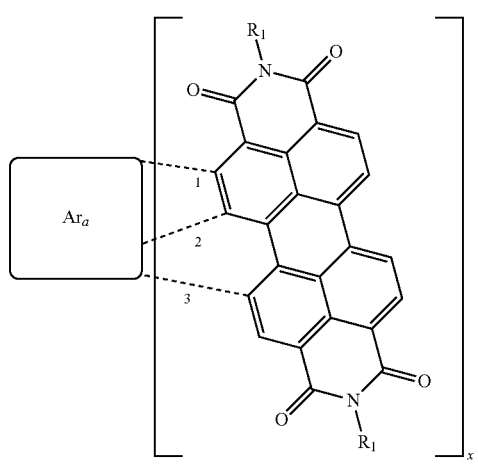

x is an integer selected from: 2, 4 and 6;

wherein when $Ar_a$ is bonded at 1, and x is 2, $Ar_a$ is selected from: a bond,

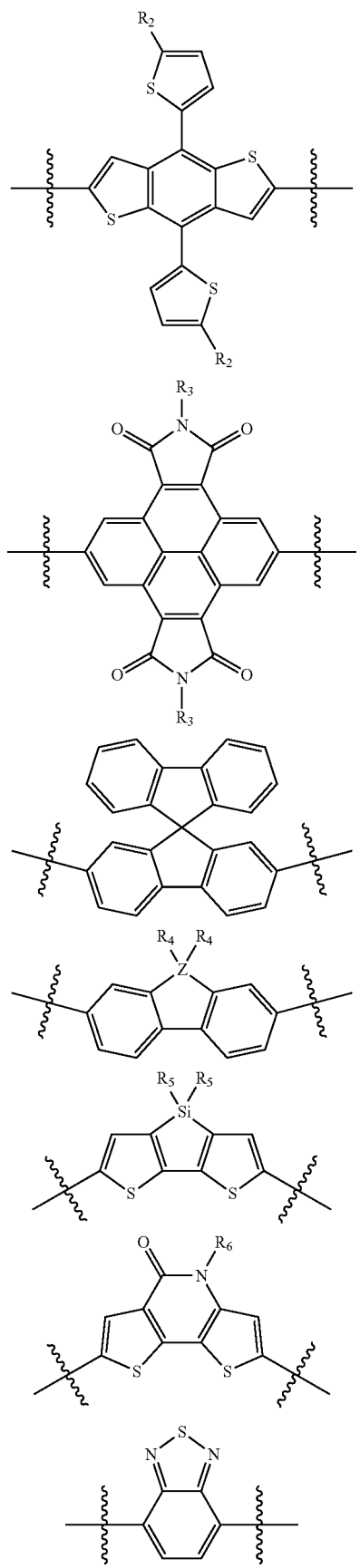

-continued
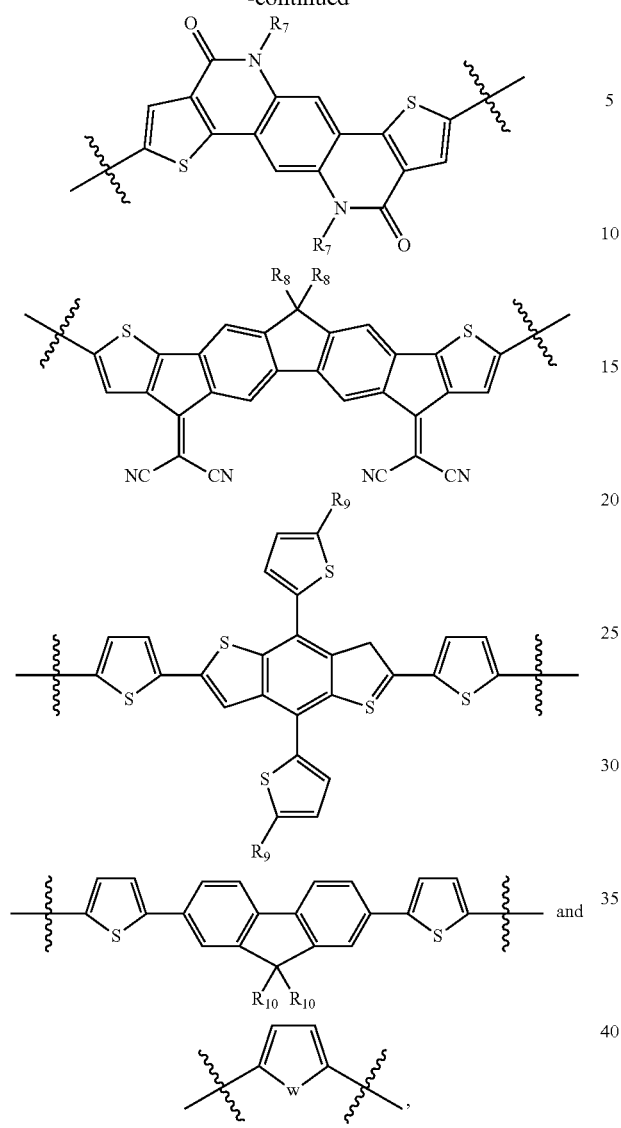
or when Ar$_a$ is bonded at 1, and x is 4, Ar$_a$ is selected from:
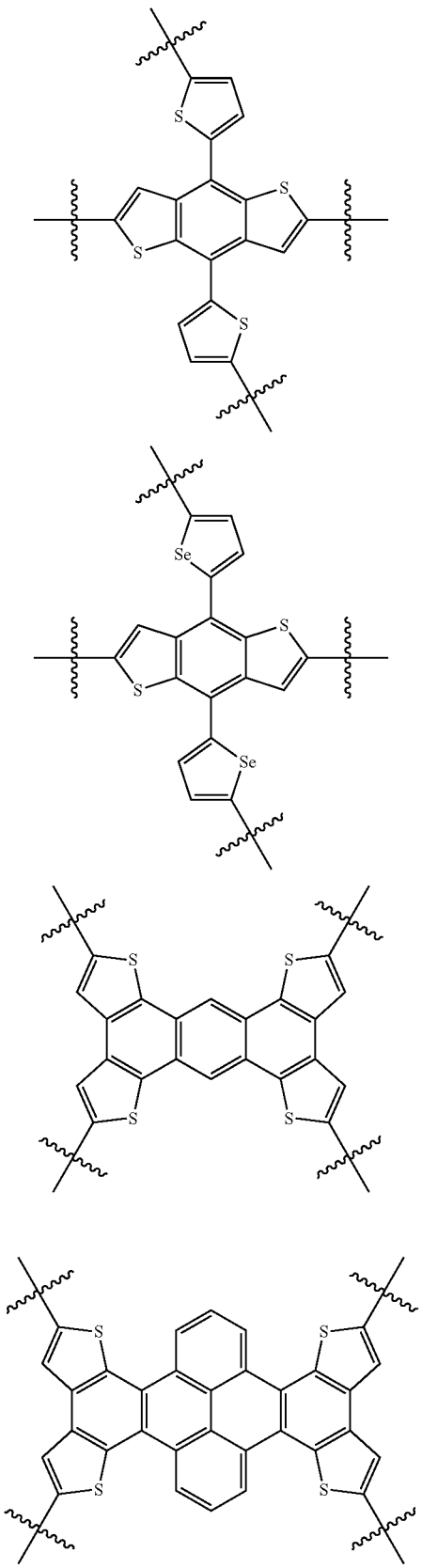
wherein R$^2$, R$^3$, R$^4$, R$^5$, R$^6$, R$^7$, R$^8$, R$^9$, and R$^{10}$, if present, are each independently selected from: C$_1$-C$_{30}$ linear or branched chain alkyl, and
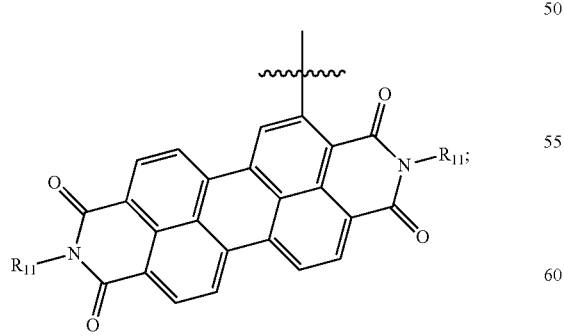
wherein R$^{11}$, if present, is C$_1$-C$_{30}$ linear or branched chain alkyl;
W is Se or S; Z is C or Si;

-continued
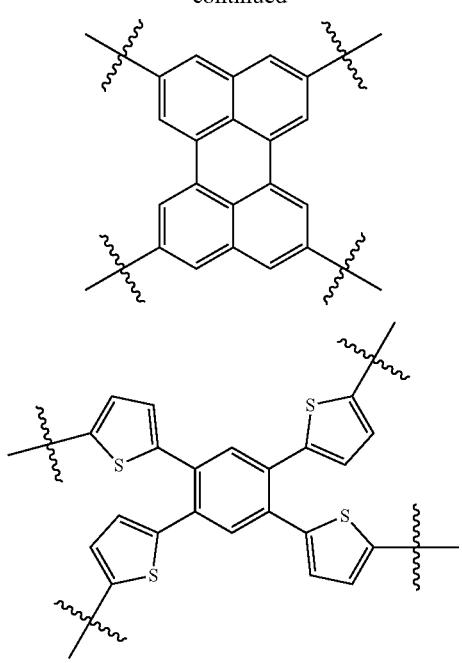
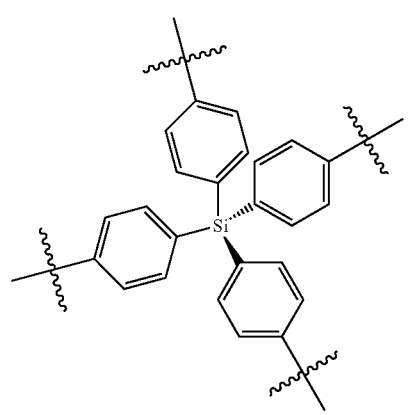
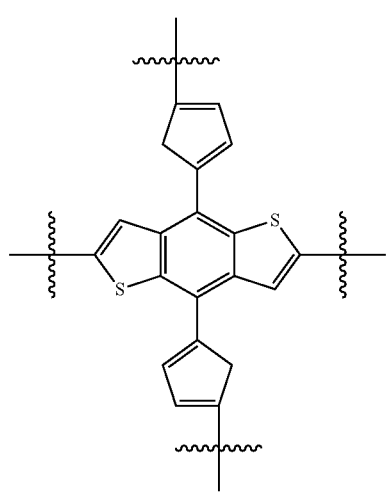
-continued
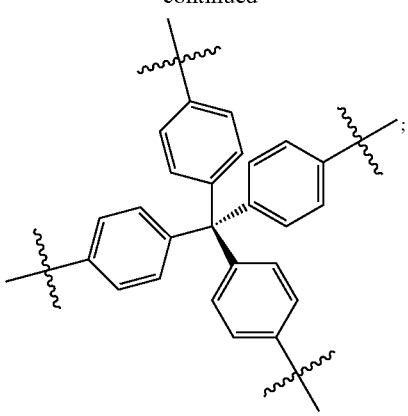
or when Ar$_a$ is bonded at 1, and x is 6, Ar$_a$ is selected from:
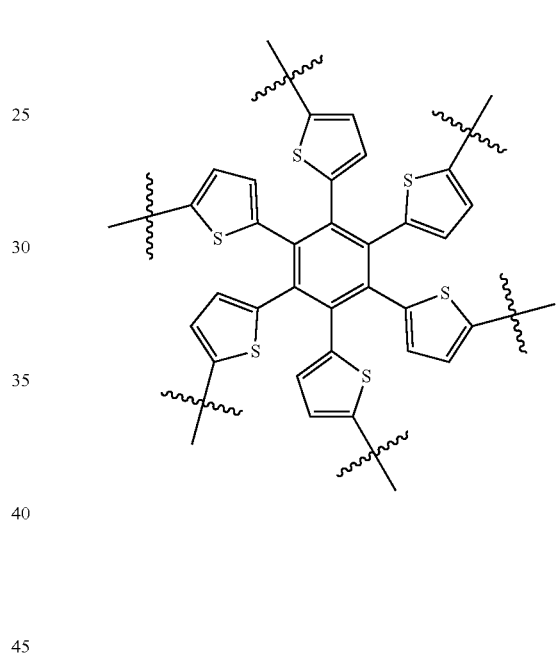
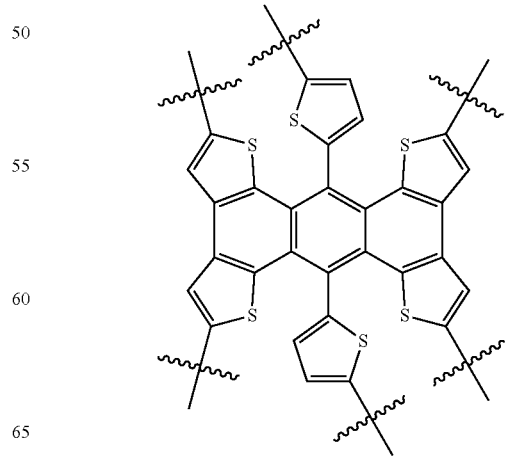

-continued
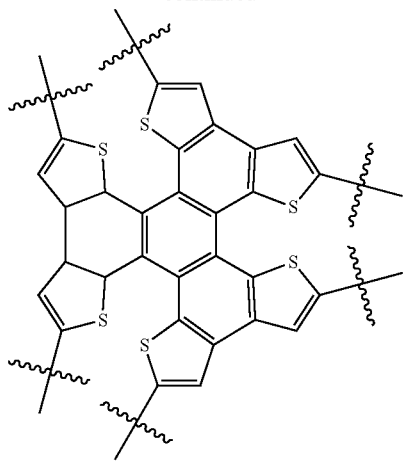
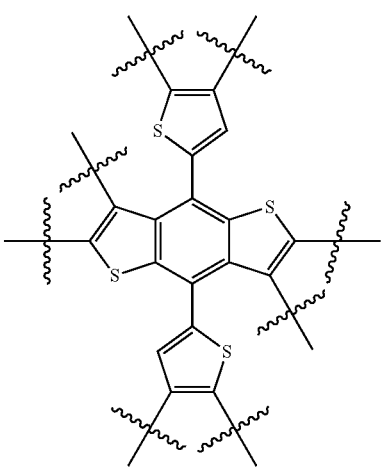
and
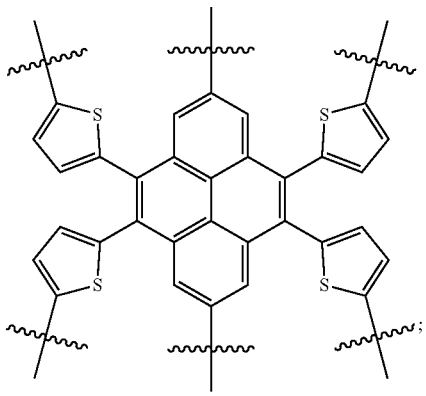
;
or when $Ar_a$ is bonded at 2 and 3 and x is 2, $Ar_a$ is selected from:
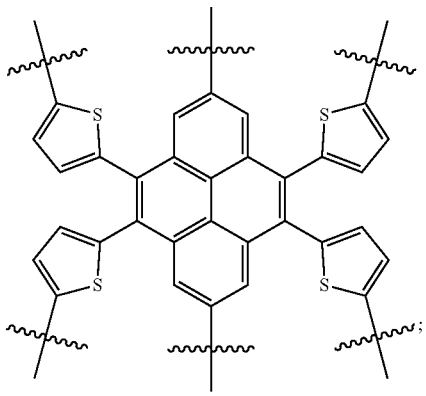
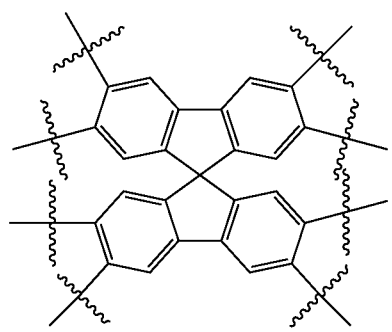
or when $Ar_a$ is bonded at 2 and 3 and x is 6, $Ar_a$ is selected from:
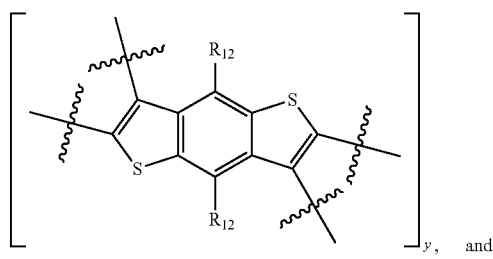
, and
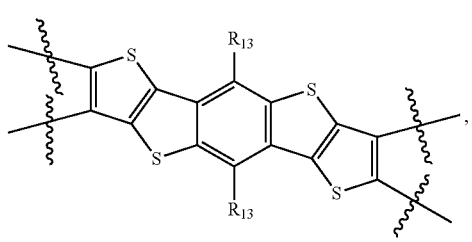
,
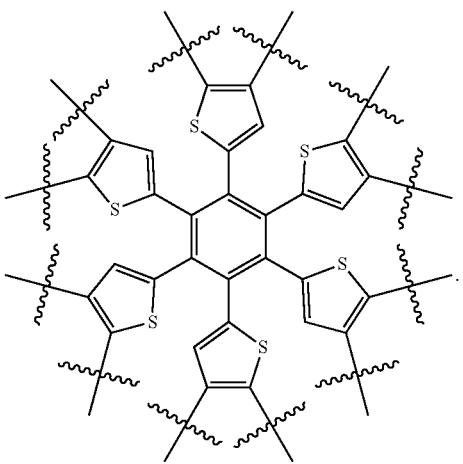 [SMILES: *c1cc(-c2c(-c3cc(*)c(*)s3)c(-c3cc(*)c(*)s3)c(-c3cc(*)c(*)s3)c(-c3cc(*)c(*)s3)c2-c2cc(*)c(*)s2)sc1*]
.
wherein $R^{12}$ and $R^{13}$, if present, are selected from: $C_1$-$C_{30}$ linear or branched chain alkyl; and
wherein y is an integer selected from 1 and 3;
or when $Ar_a$ is bonded at 2 and 3 and x is 4, $Ar_a$ is selected from:

In one embodiment, a molecular acceptor of formula I:
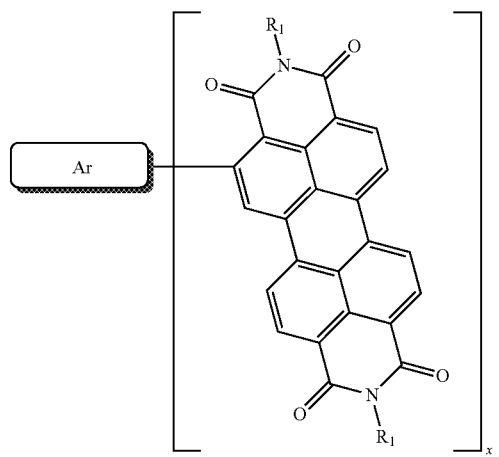
where $R^1$ is selected from: $C_1$-$C_{30}$ linear or branched chain alkyl;
x is an integer selected from: 2, 4 and 6;
wherein when x is 2, Ar is selected from: a bond,
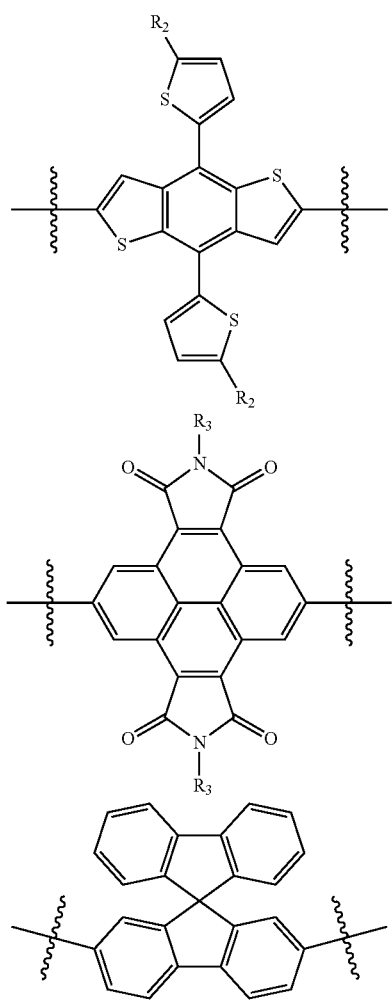
-continued
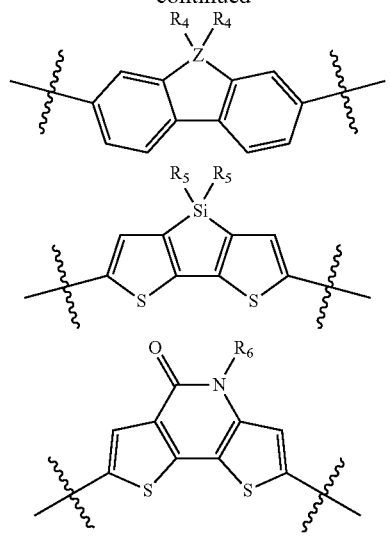
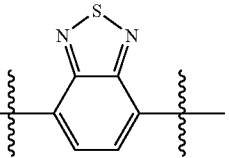
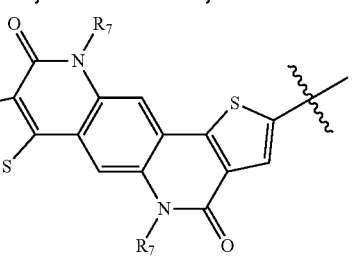
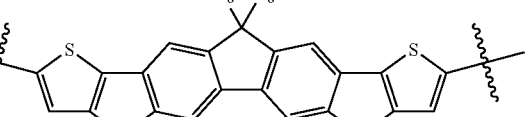
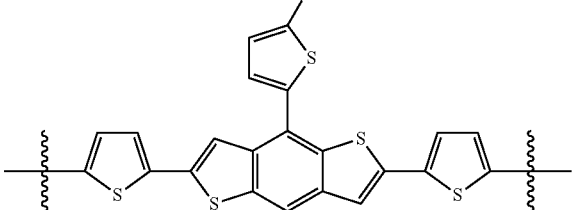
and -continued
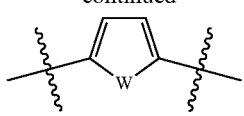
R², R³, R⁴, R⁵, R⁶, R⁷, R⁸, R⁹ and R¹⁰, if present, are each independently selected from: $C_1$-$C_{30}$ linear or branched chain alkyl, and
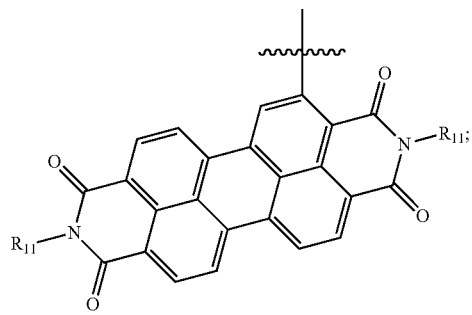
R¹¹, if present, is $C_1$-$C_{30}$ linear or branched chain alkyl;
W is Se or S; Z is C or Si;
or when x is 4, Ar is selected from:
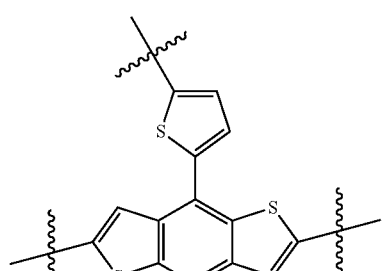
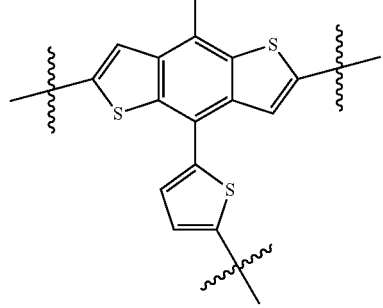
-continued
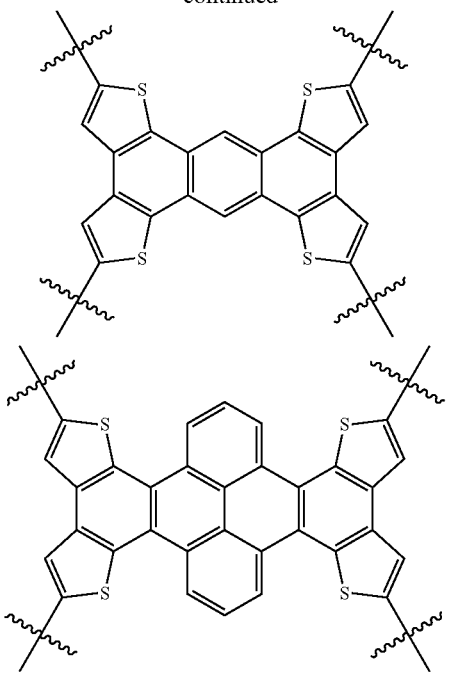
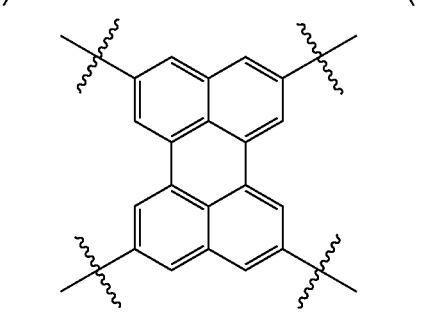
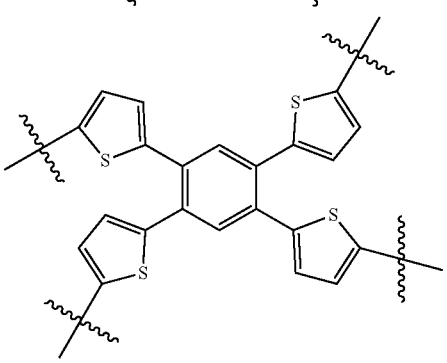
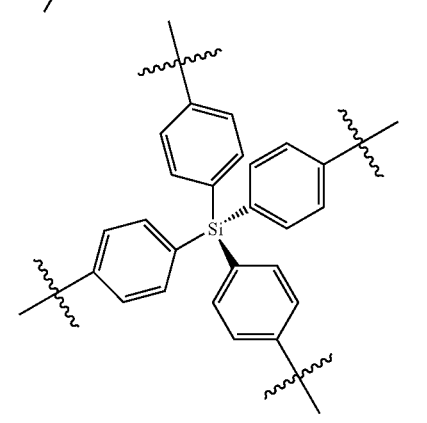

-continued
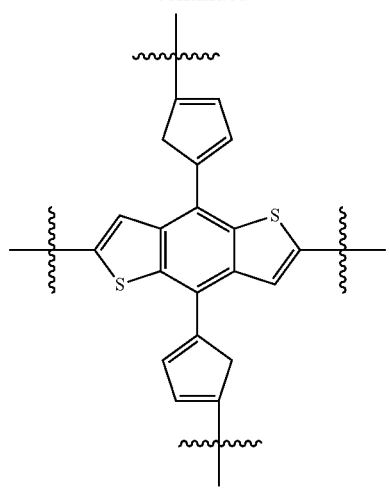
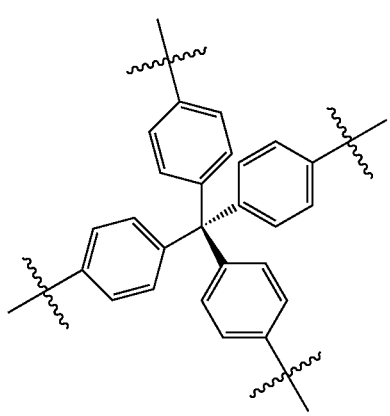
or when x is 6, Ar is selected from:
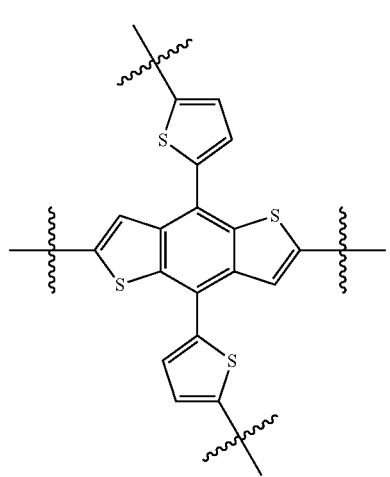
-continued
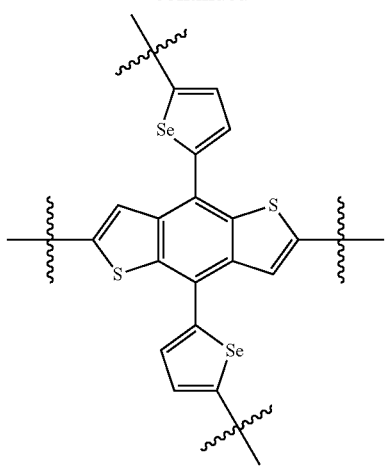
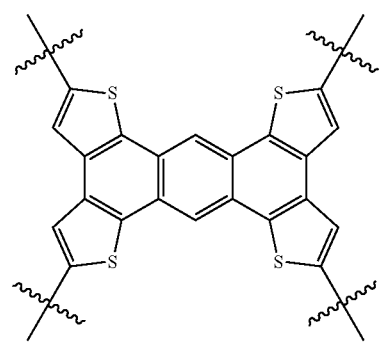
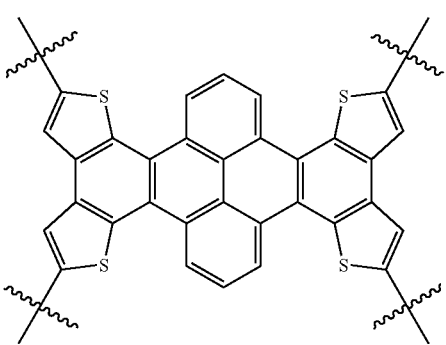
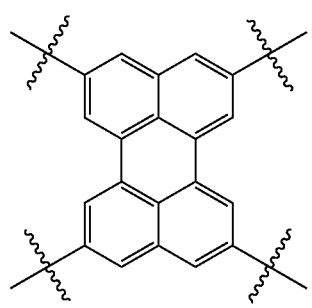

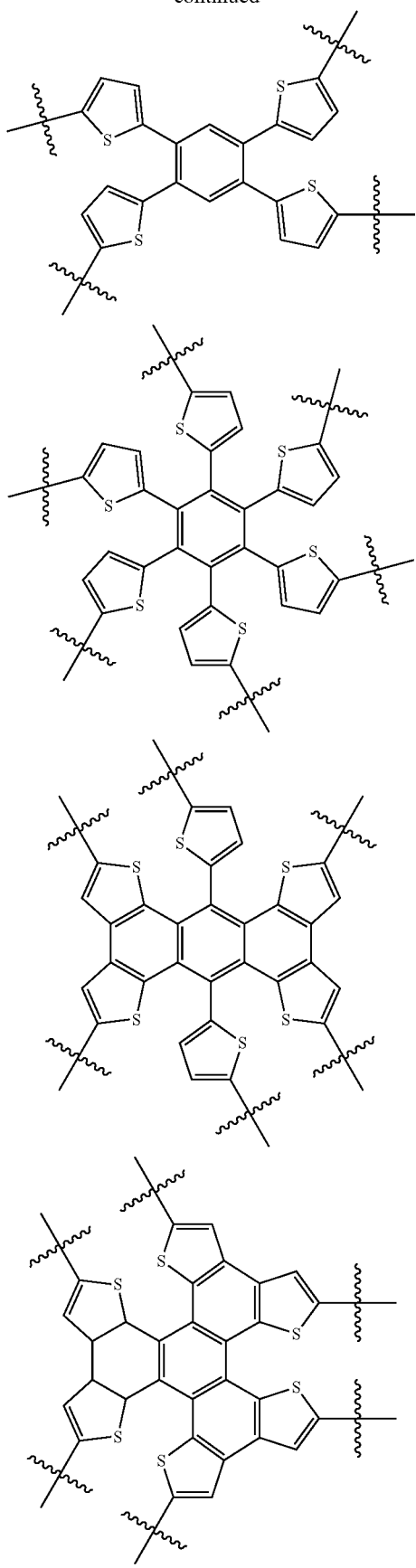
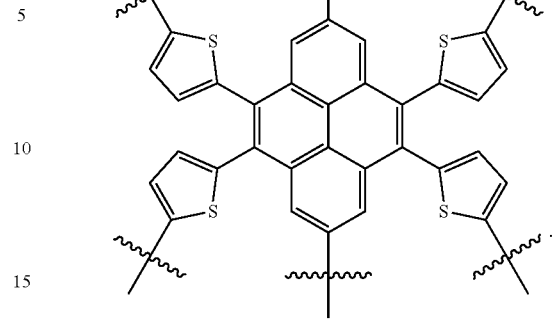
In one aspect, the molecular acceptor is further selected from an acceptor of formula VI:
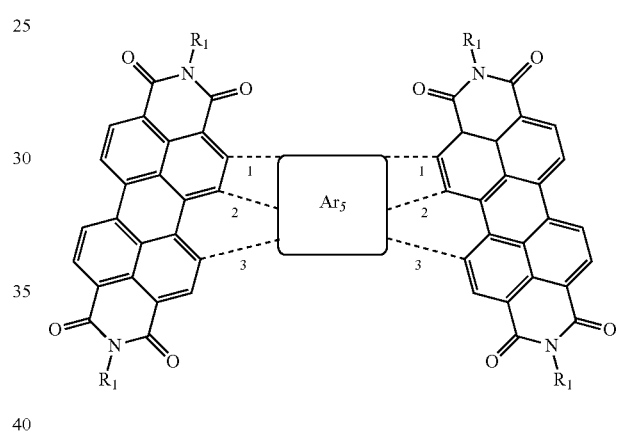
where $R_1$ is a selected from: $C_1$-$C_{30}$ linear or branched chain alkyl; and
when $Ar_5$ is bonded at 1, $Ar_5$ is selected from: a bond
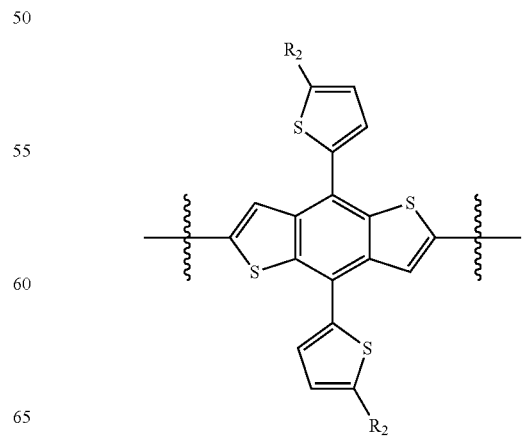

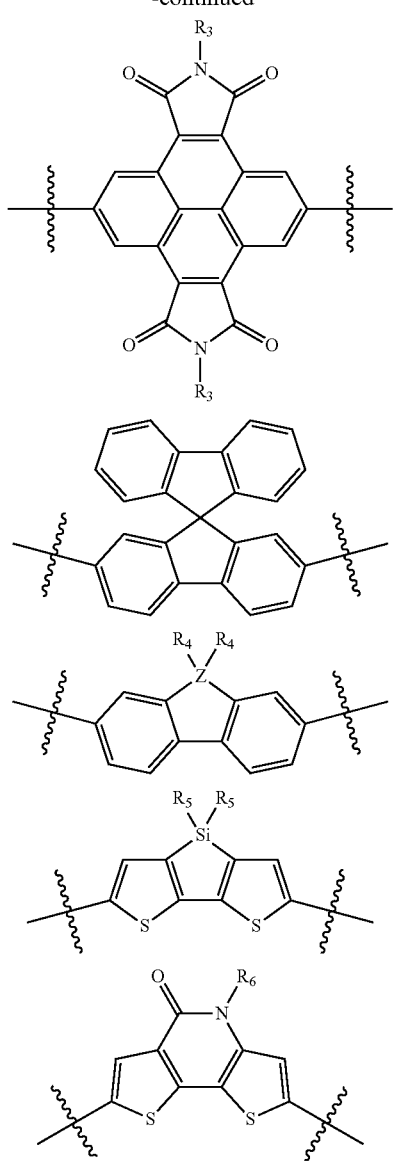
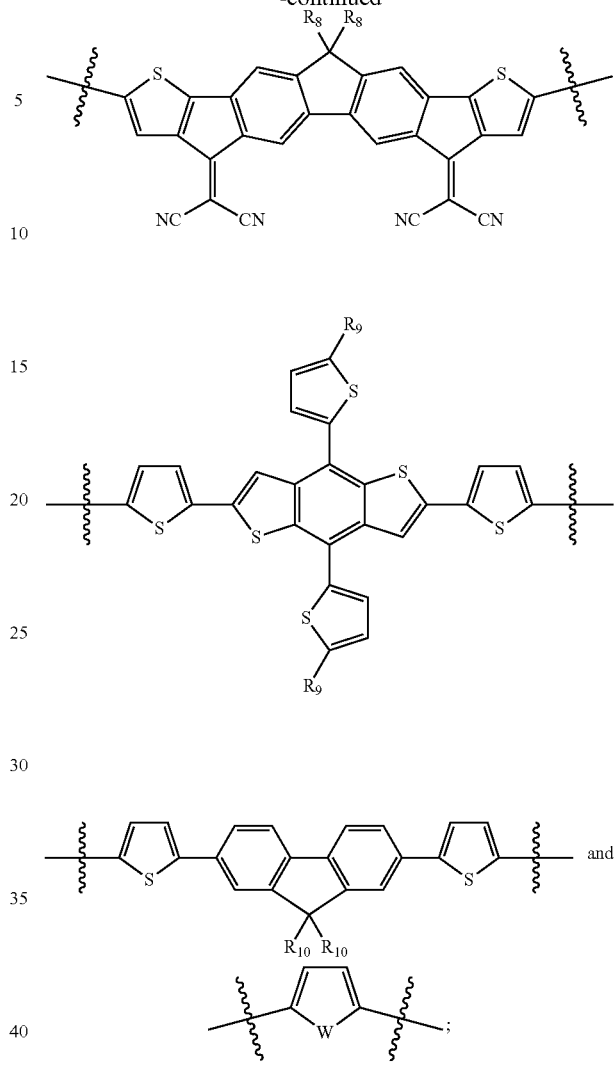
wherein $R^2$, $R^3$, $R^4$, $R^5$, $R^6$, $R^7$, $R^8$, $R^9$ and $R^{10}$, if present, are each independently selected from: $C_1$-$C_{30}$ linear or branched chain alkyl, and
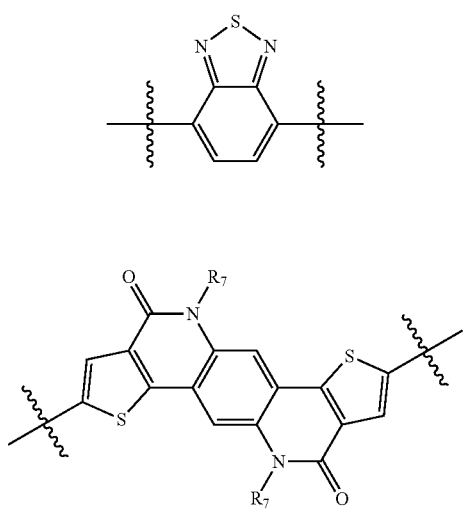
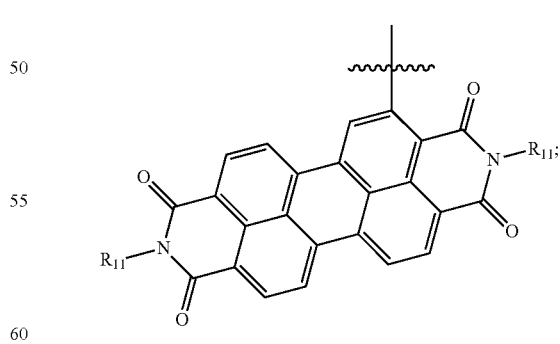
wherein $R^{11}$, if present, is $C_1$-$C_{30}$ linear or branched chain alkyl;
W is Se or S; Z is C or Si;
Or wherein when $Ar_5$ is bonded at 2 and 3, where $Ar_5$ is selected from:

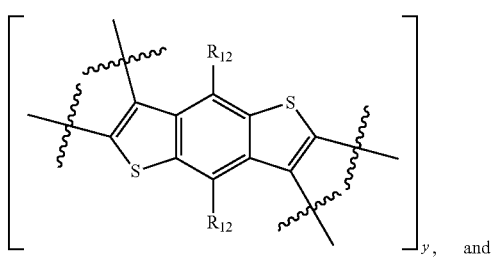
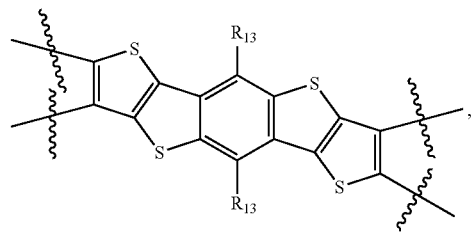
wherein $R^{12}$ and $R^{13}$, if present, are selected from: $C_1$-$C_{30}$ linear or branched chain alkyl; and
wherein y is an integer selected from 1 and 3.
In one aspect, the molecular acceptor is further selected from an acceptor of formula II:
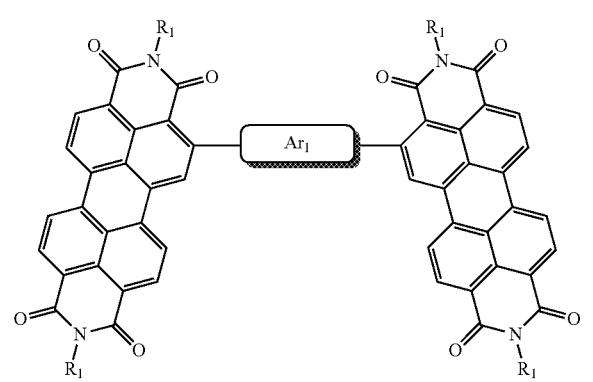
where $R_1$ is a selected from: $C_1$-$C_{30}$ linear or branched chain alkyl; and
$Ar_1$ is selected from: a bond,
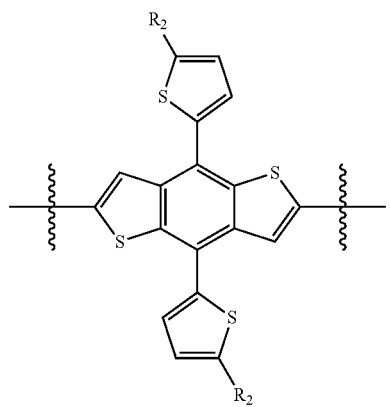
-continued
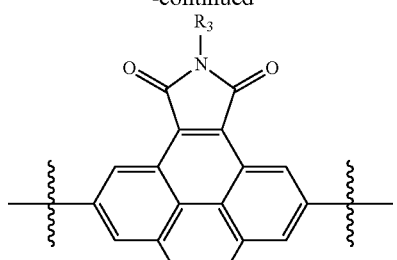
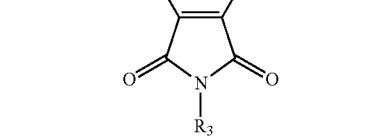
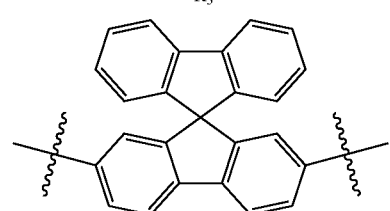
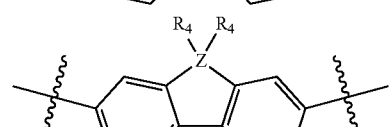
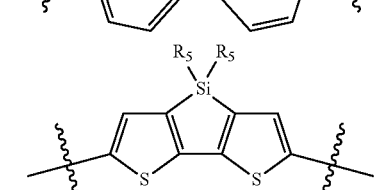
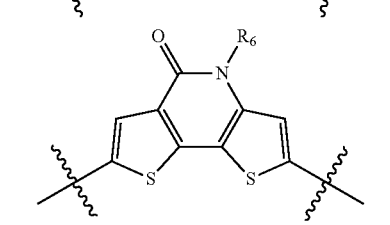
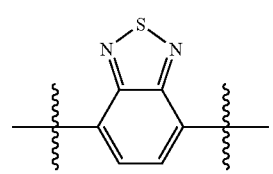
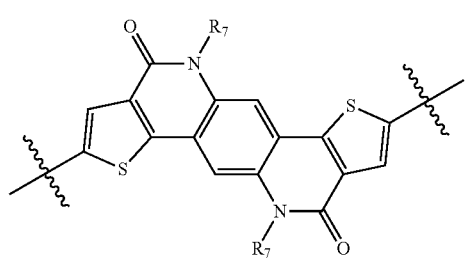

31
-continued
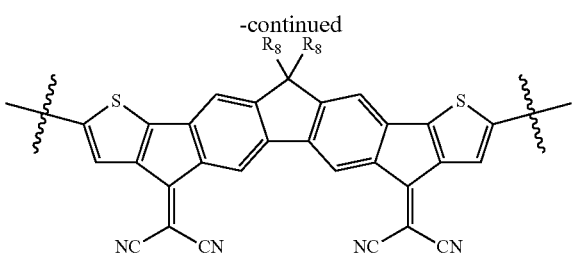
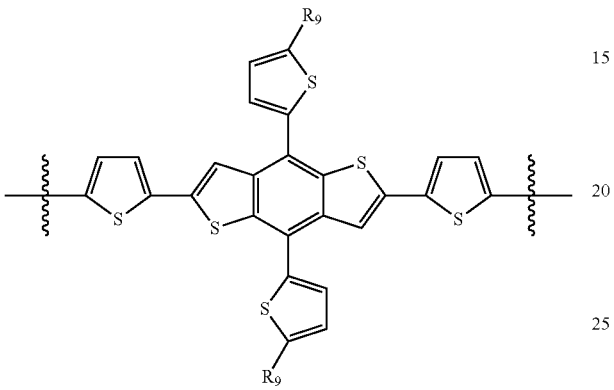
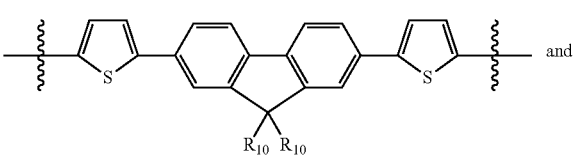
and
32
-continued
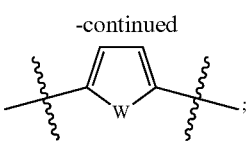
$R^2$, $R^3$, $R^4$, $R^5$, $R^6$, $R^7$, R, $R^9$ and $R^{10}$, if present, are each independently selected from a: $C_1$-$C_{30}$ linear or branched chain alkyl, and
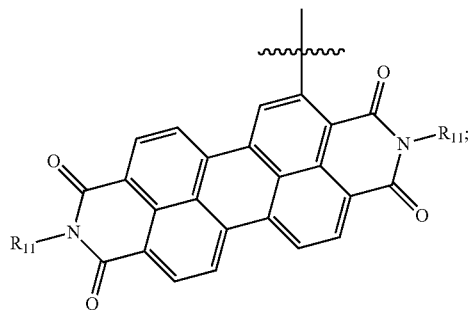
$R^{11}$, if present, is $C_1$-$C_{30}$ linear or branched chain alkyl;
W is Se or S; and Z is C or Si.
In one aspect, the molecular acceptor further selected from:
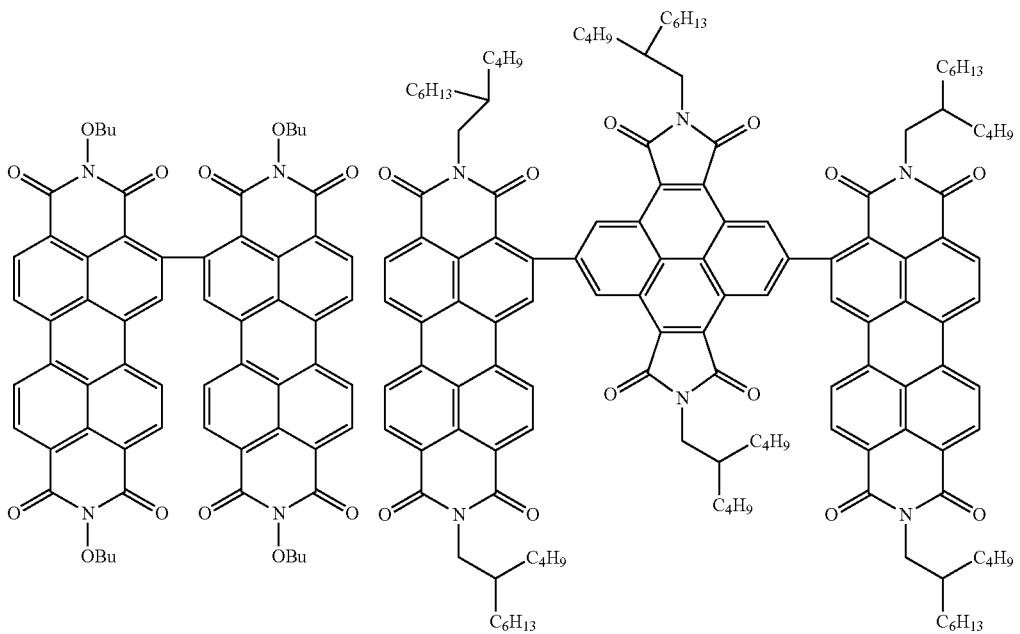

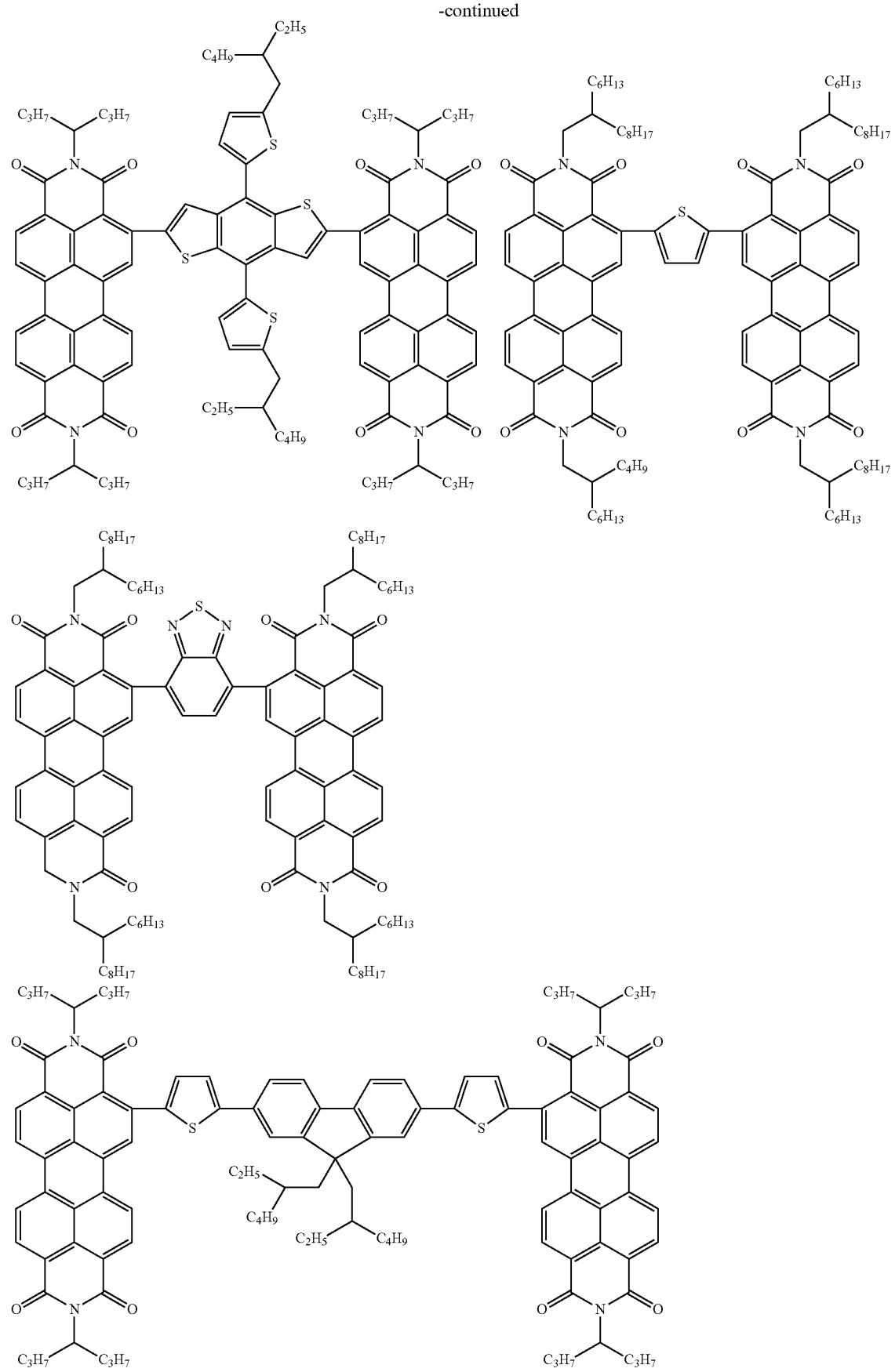

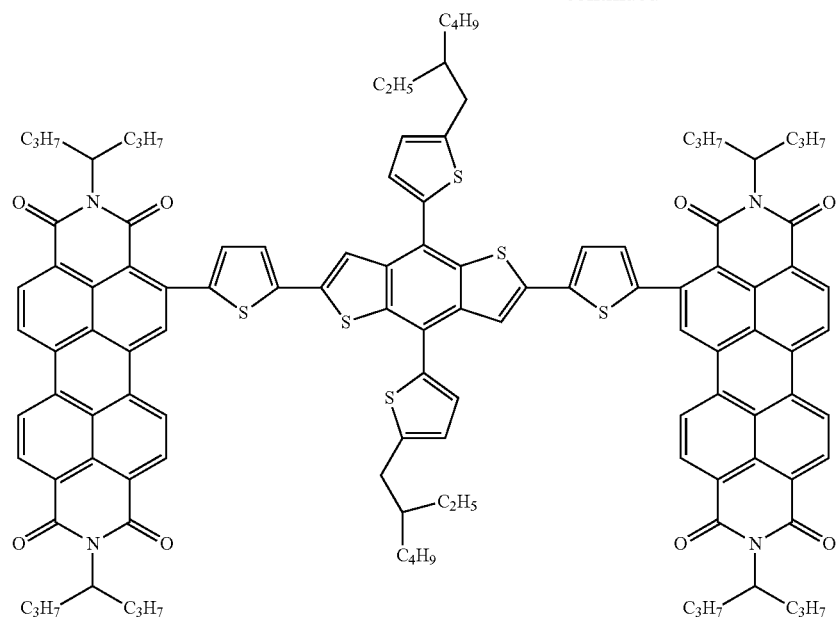
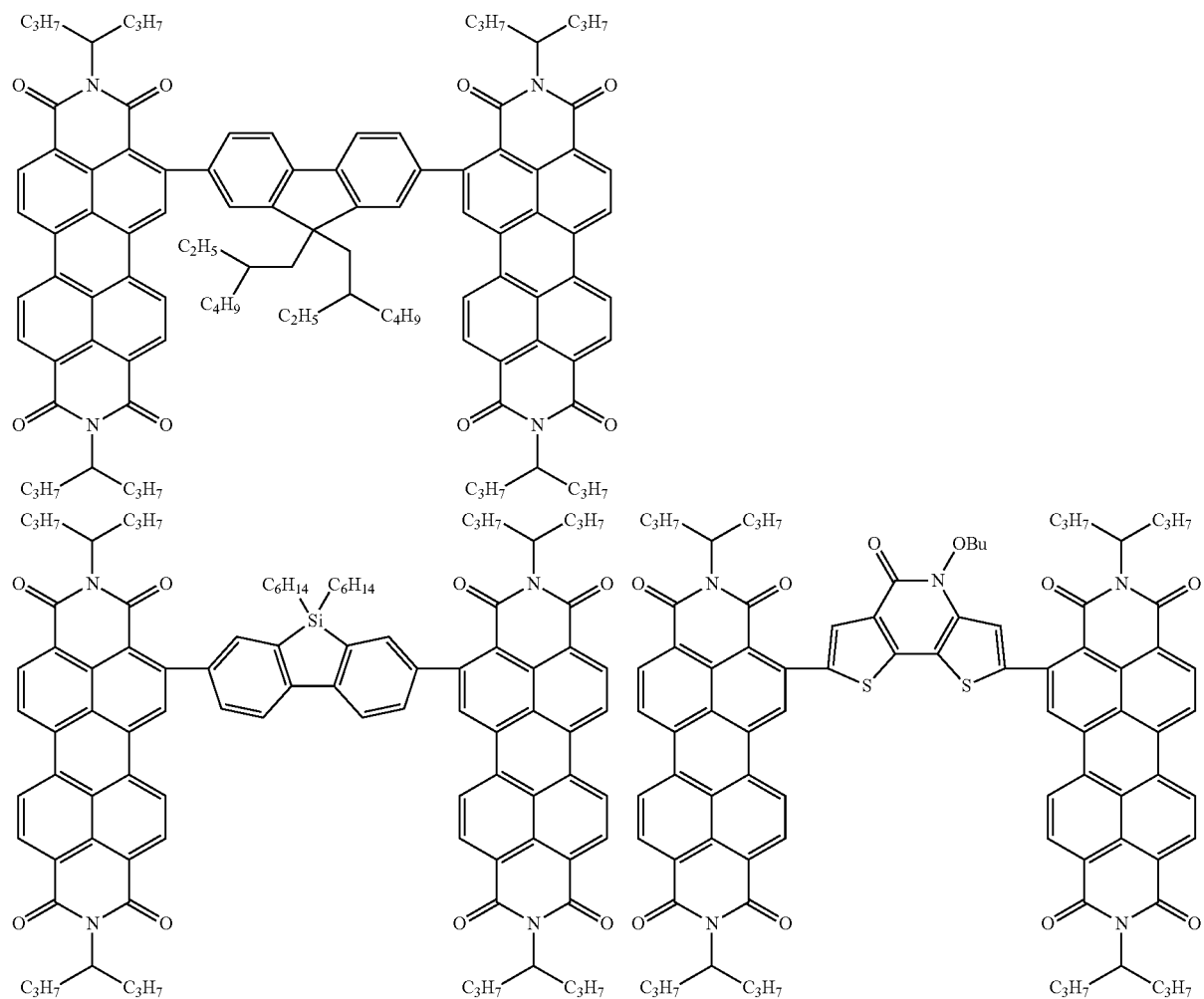

-continued
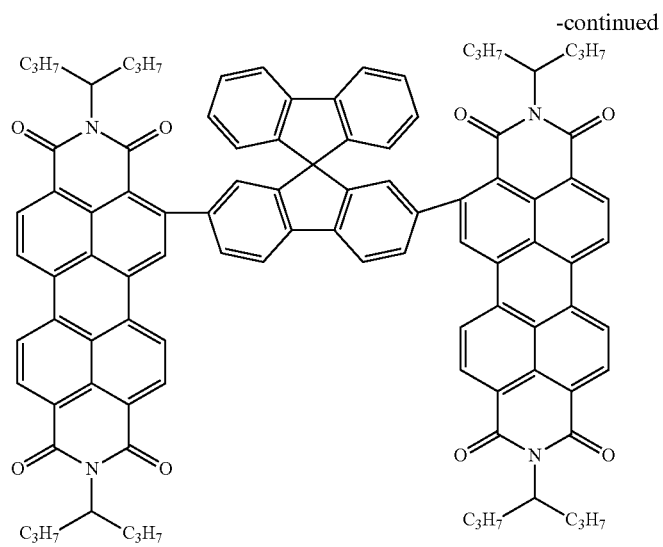
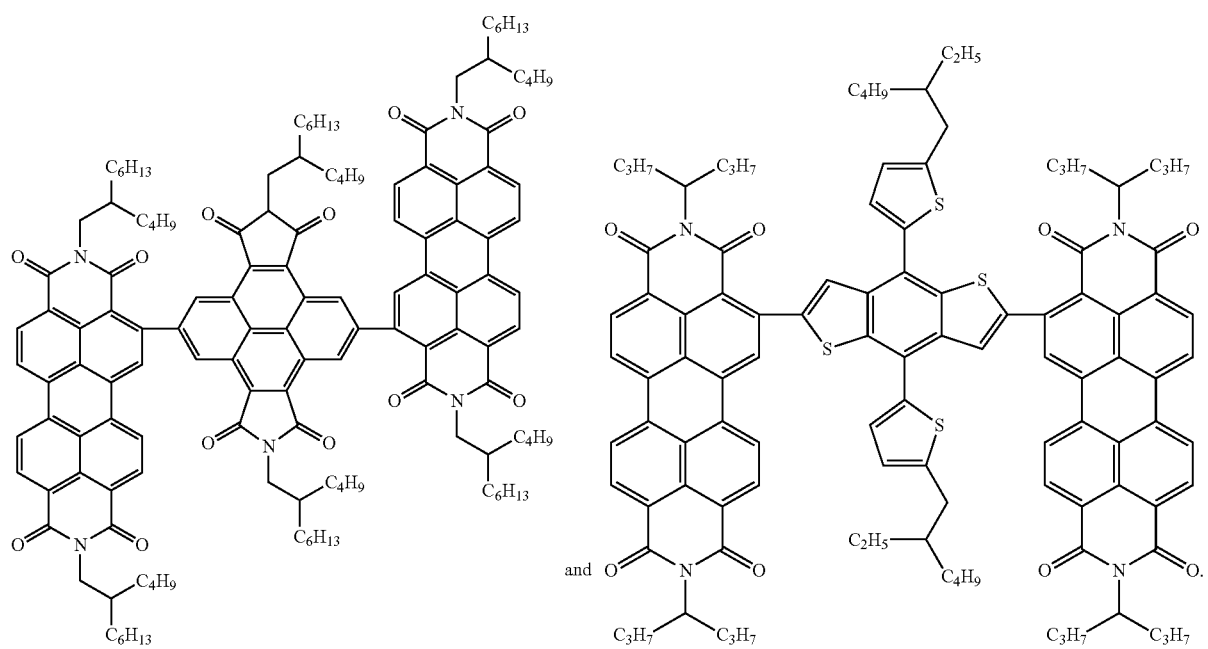

In one aspect, the molecular acceptor having a power conversion efficiency of greater than 4.92%.

In one aspect, the molecular acceptor further selected from an acceptor of formula VII:

where $R_1$ is a selected from: $C_1$-$C_{30}$ linear or branched chain alkyl; and wherein $Ar_6$ is selected from:

wherein $R^{12}$ and $R^{13}$, if present, are selected from: $C_1$-$C_{30}$ linear or branched chain alkyl; and
wherein y is an integer selected from 1 and 3.

In one aspect, the molecular acceptor further selected from:

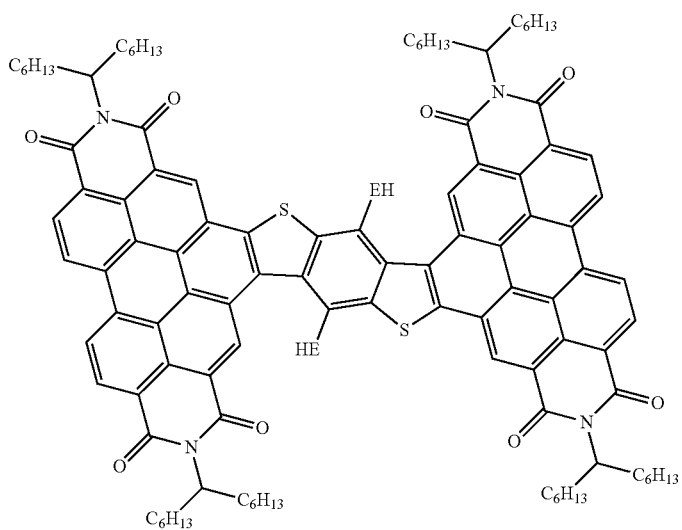

-continued
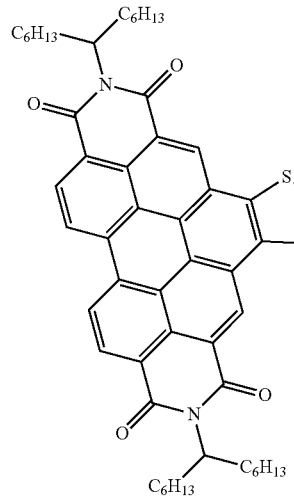
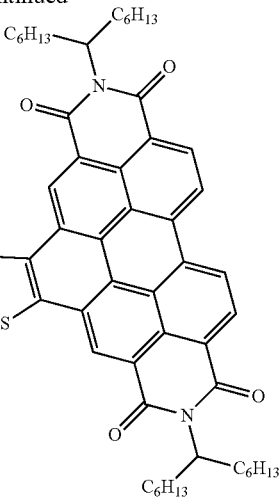
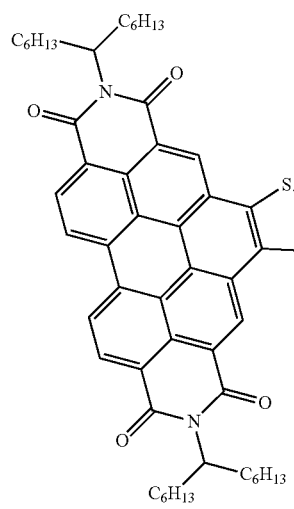
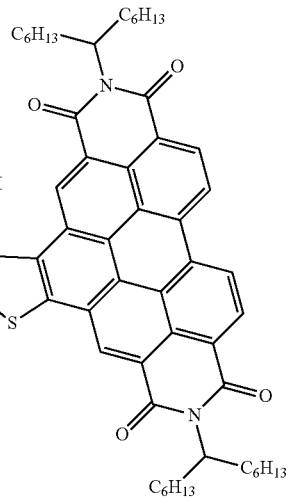
wherein EH is 2-ethyl hexyl.

In one aspect, the molecular acceptor having a power conversion efficiency of greater than 5.59%.
In one aspect, the molecular acceptor further selected from an acceptor of formula IX:
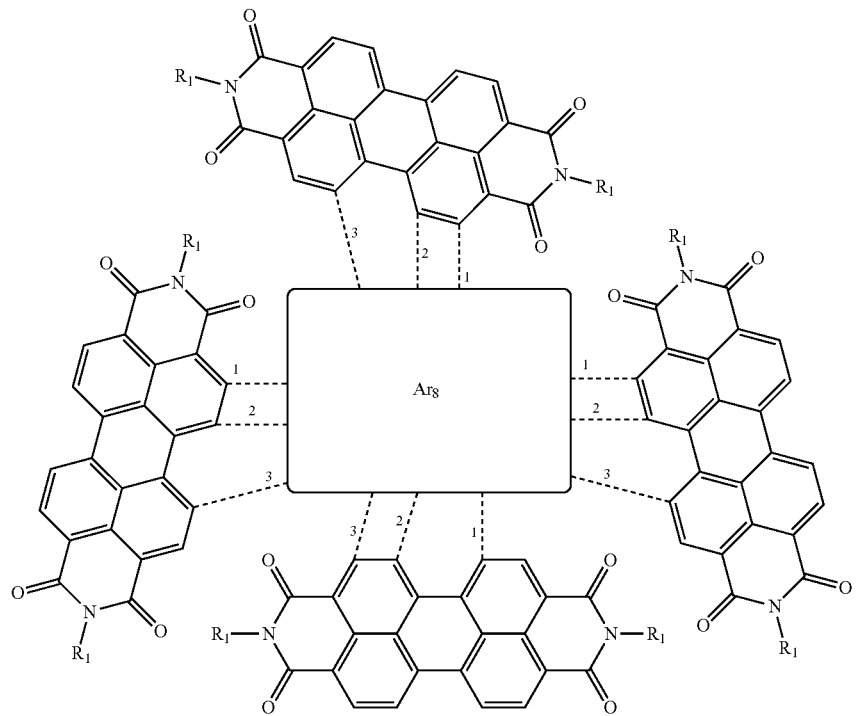
where $R^1$ is $C_1$-$C_{30}$ linear or branched chain alkyl; and
wherein when $Ar_8$ is bonded at 1 $Ar_8$ is selected from
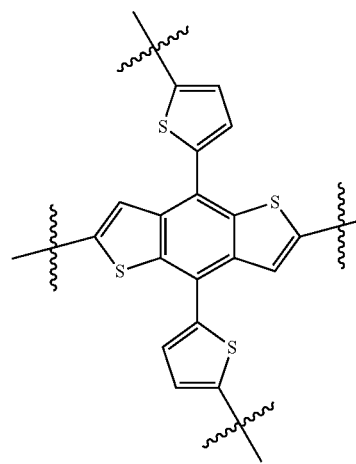
-continued
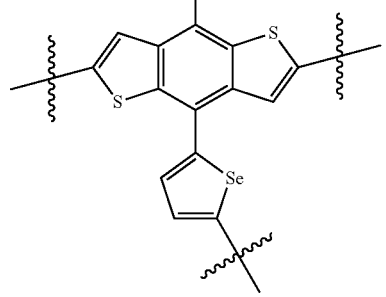
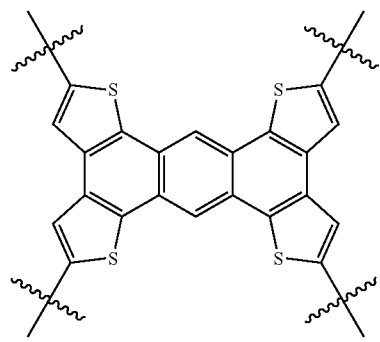

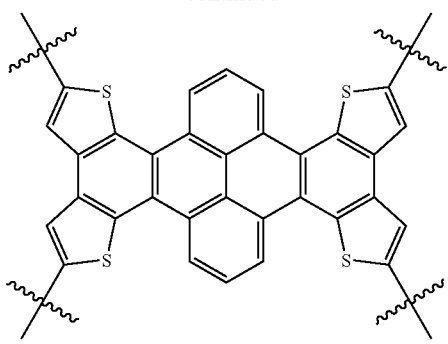
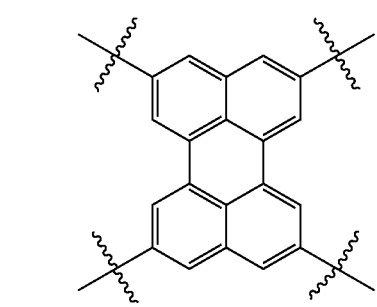
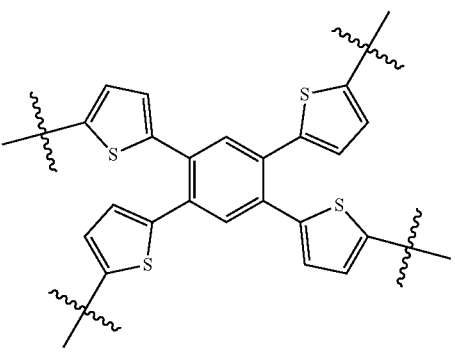
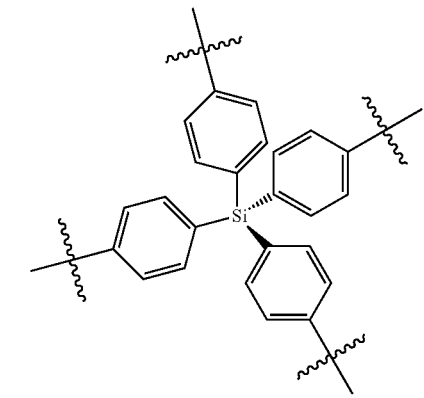
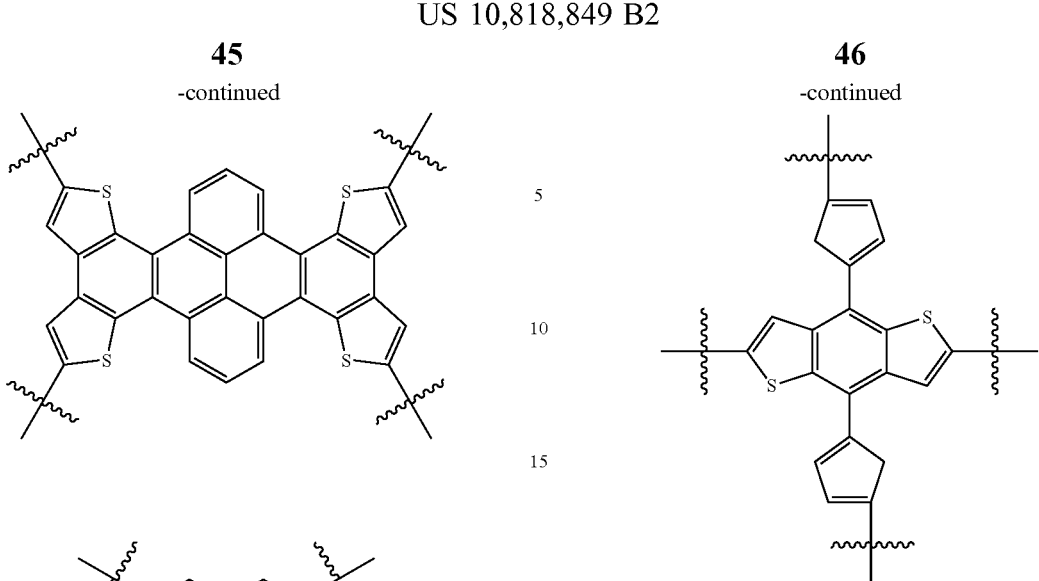
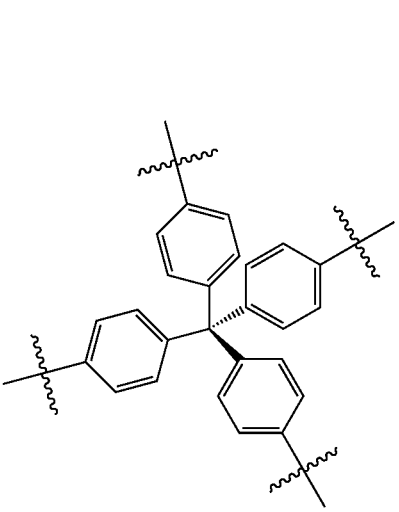
or when Ar₈ is bonded at 2 and 3, and Ar₈ is selected from:
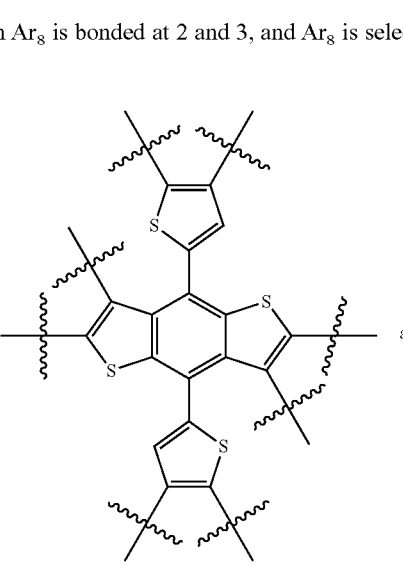
and

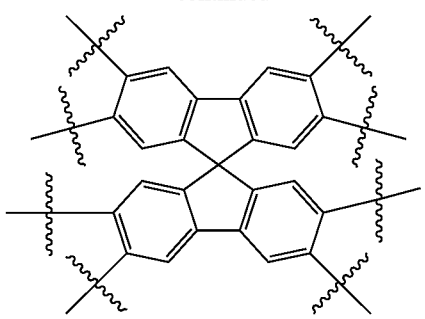
In one aspect, the molecular acceptor selected from an acceptor of formula III:
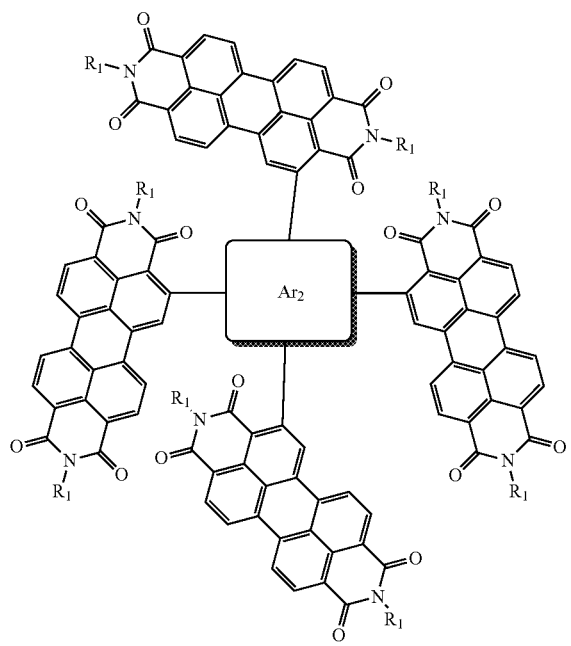
where $R^1$ is $C_1$-$C_{30}$ linear or branched chain alkyl; and $Ar_2$ is selected from the group consisting of:
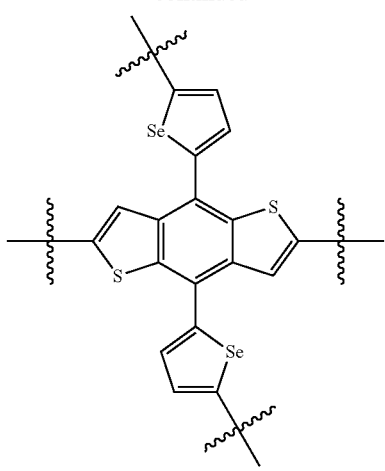
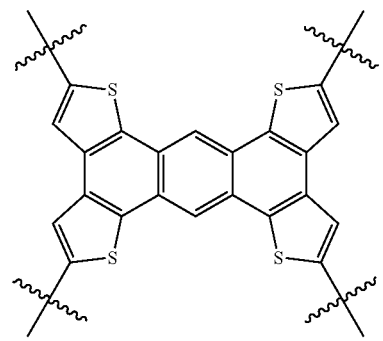
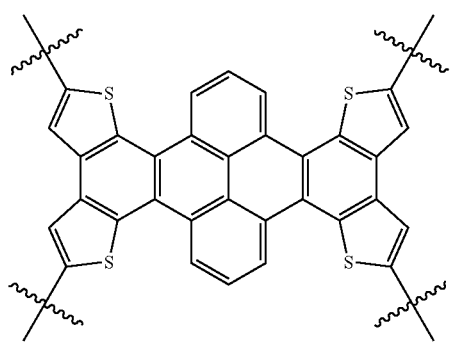
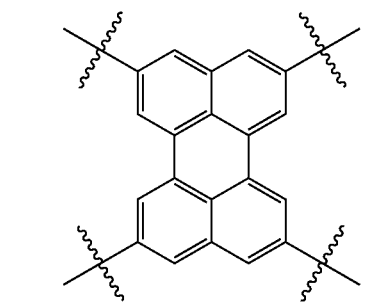

-continued
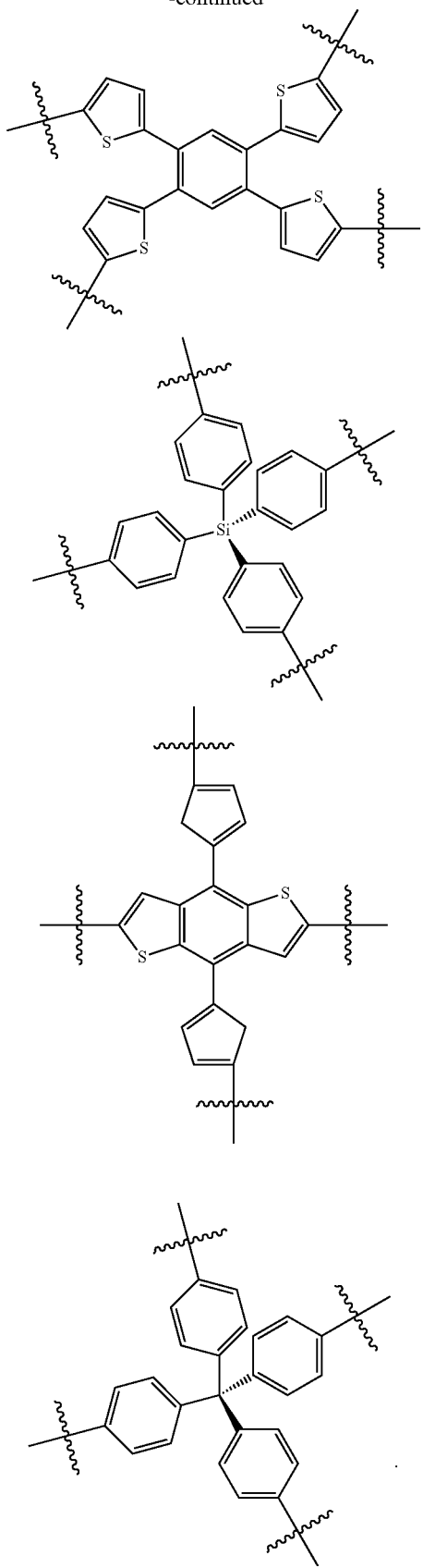
In one aspect, the molecular acceptor is selected from:
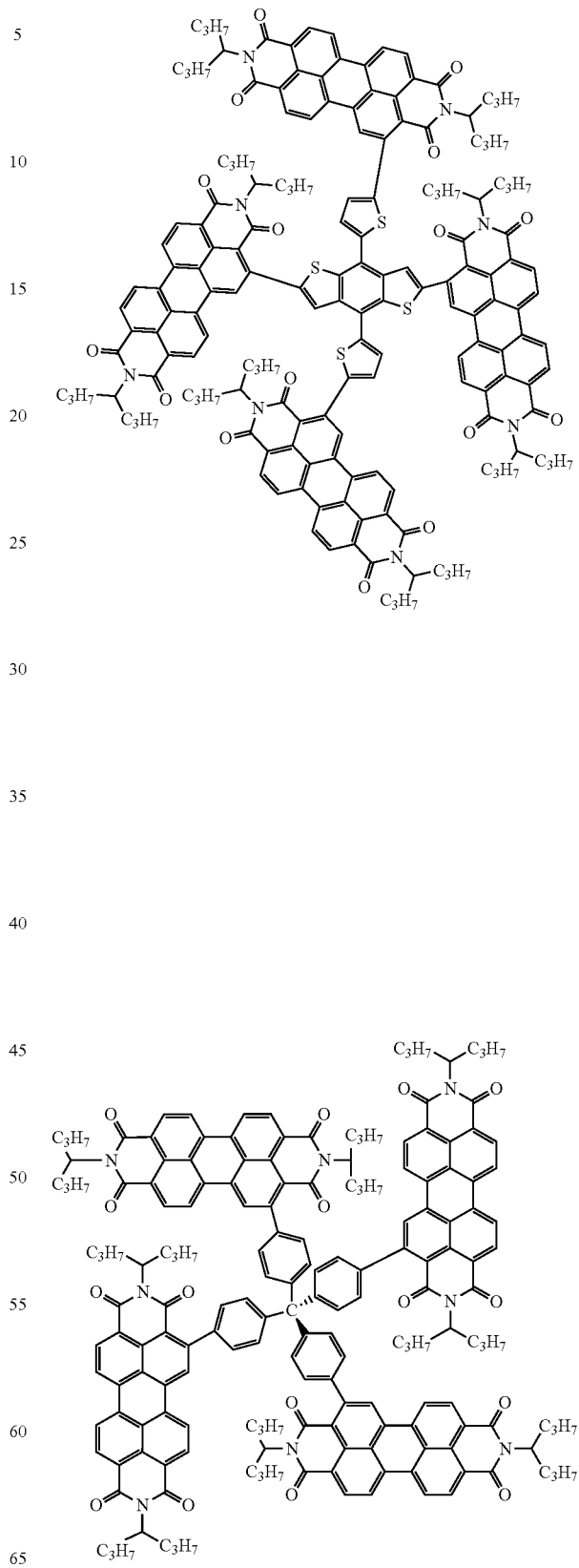

-continued
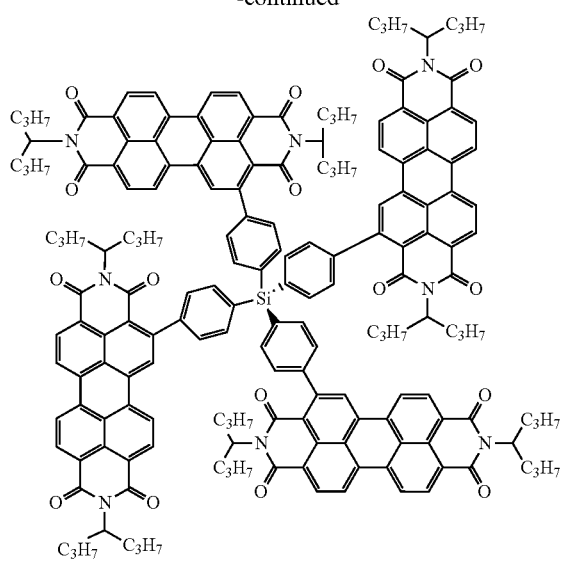
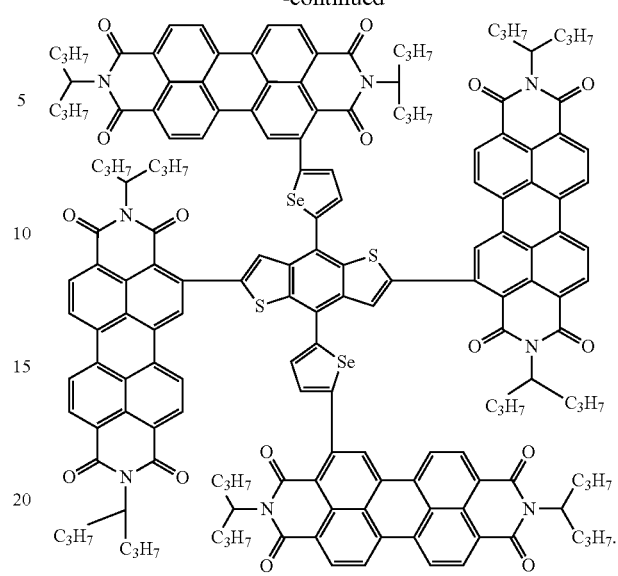
In one aspect, the molecular acceptor is further selected from an acceptor of formula X:
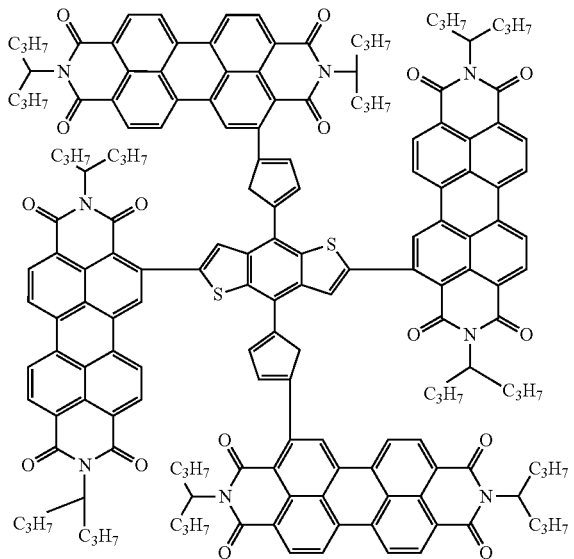
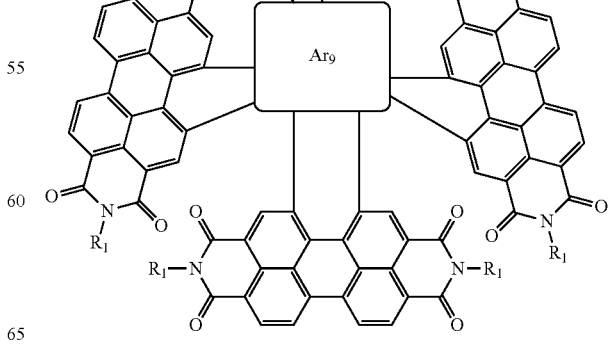

where $R^1$ is $C_1$-$C_{30}$ linear or branched chain alkyl; and $Ar_9$ is selected from:
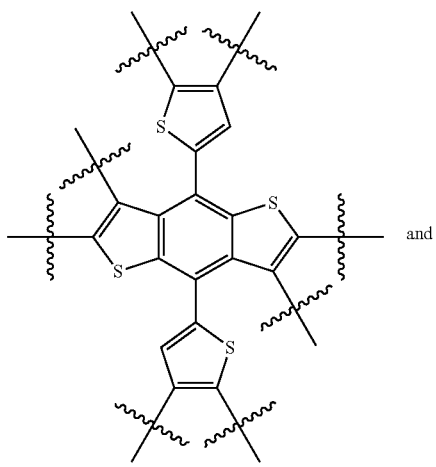
and
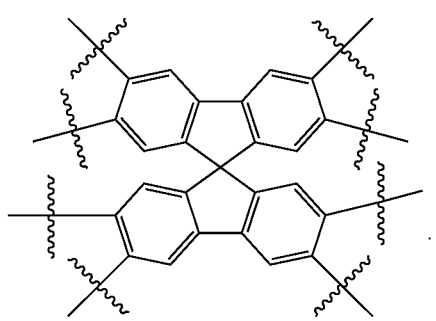
In one aspect, the molecular acceptor is further selected from:
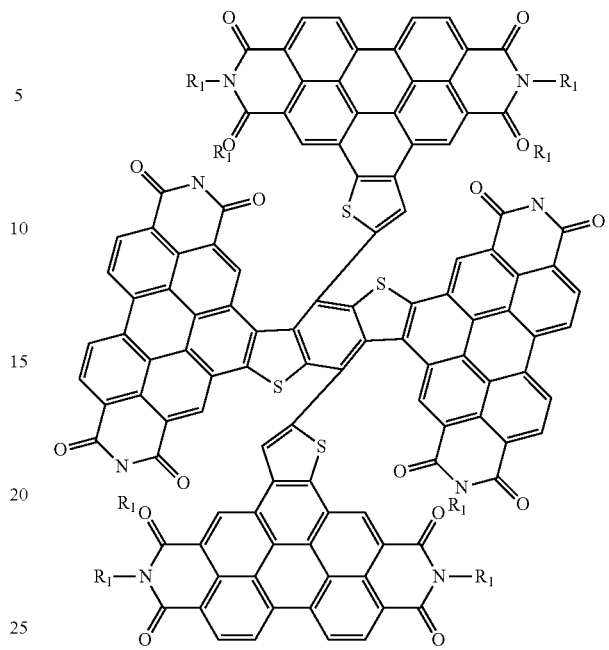
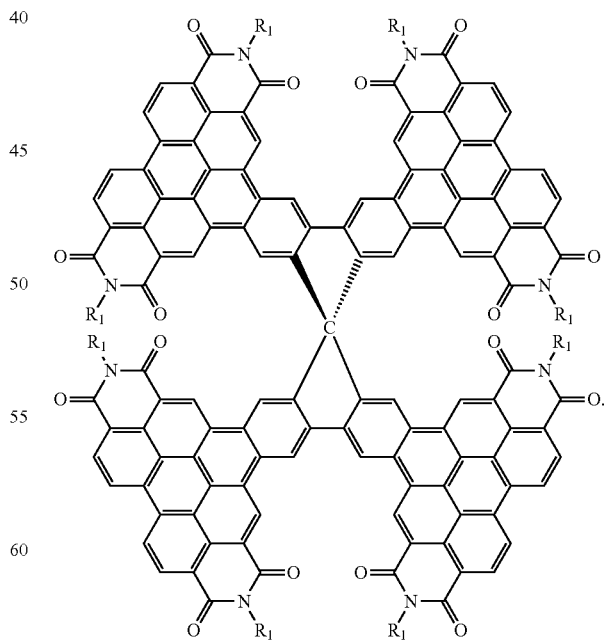
In one aspect, the molecular acceptor further selected from an acceptor of formula XI:

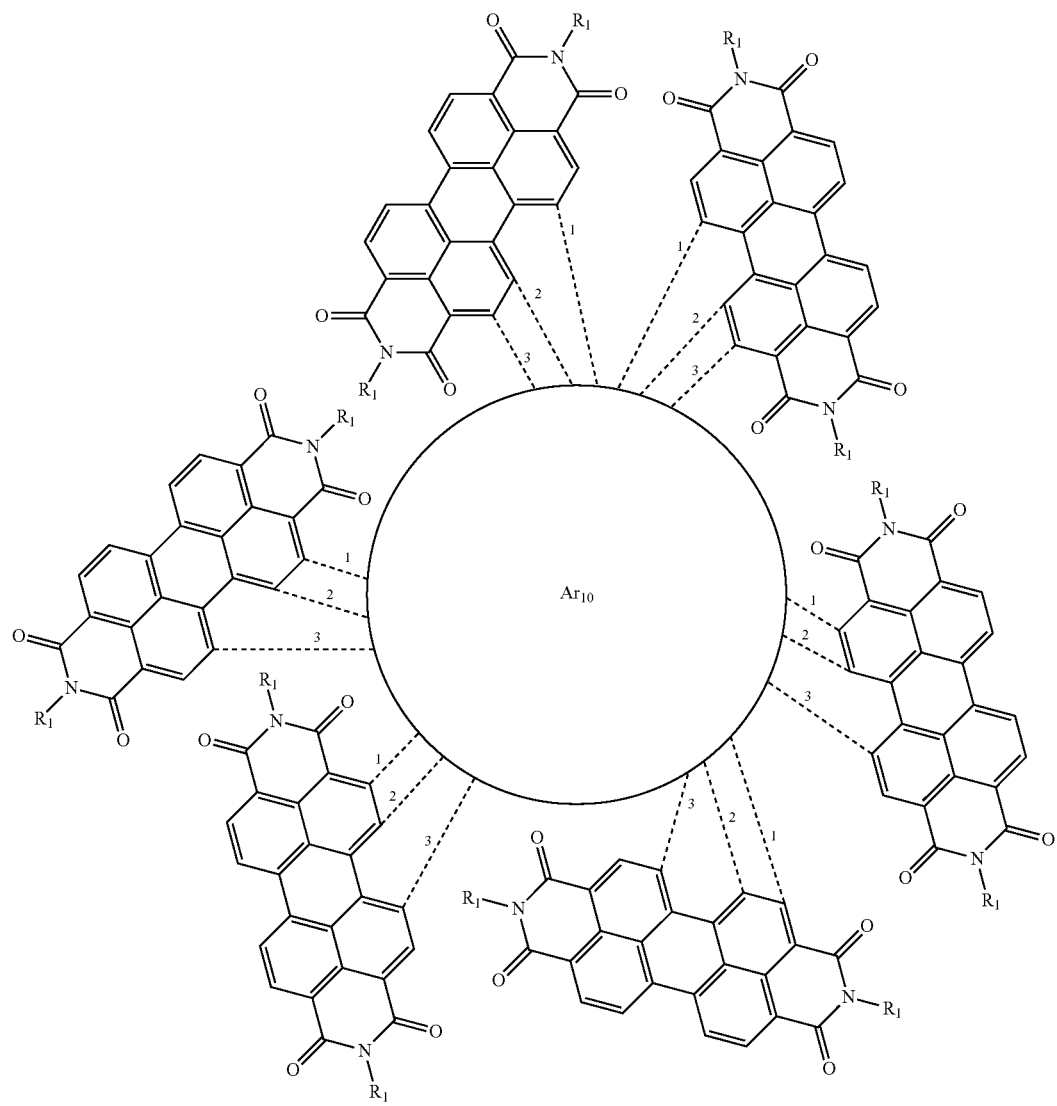
where R₁ is selected from: $C_1$-$C_{30}$ linear or branched chain alkyl; and
when $Ar_{10}$ is bonded at 1, $Ar_{10}$ is selected from:
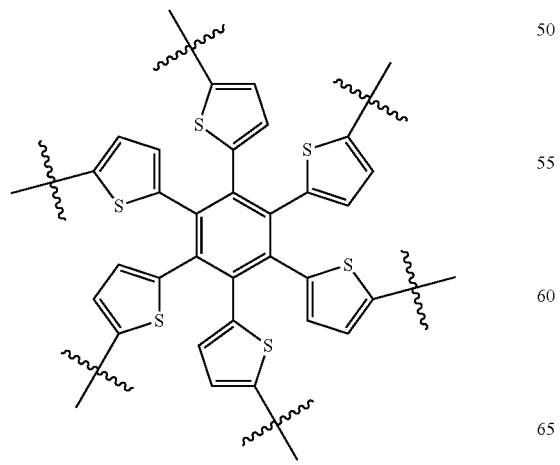

-continued
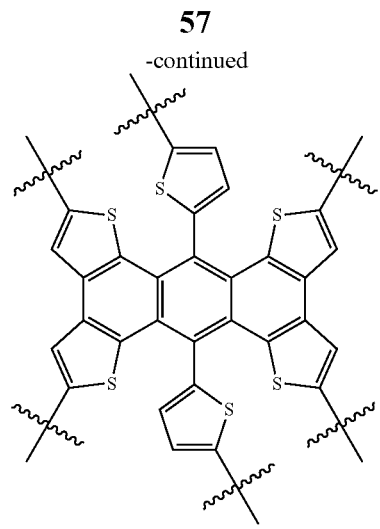
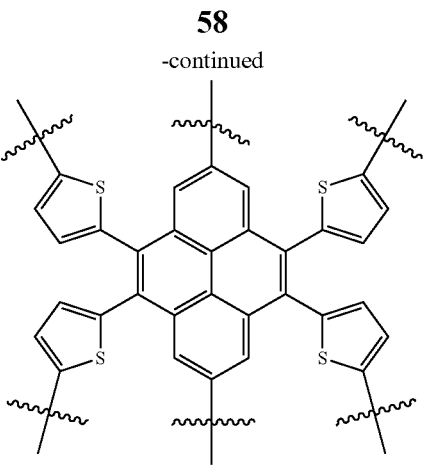
or when Ar$_{10}$ is bonded at 2 and 3, Ar$_{10}$ is:
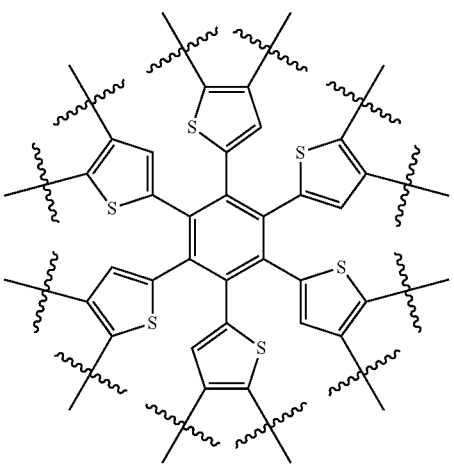
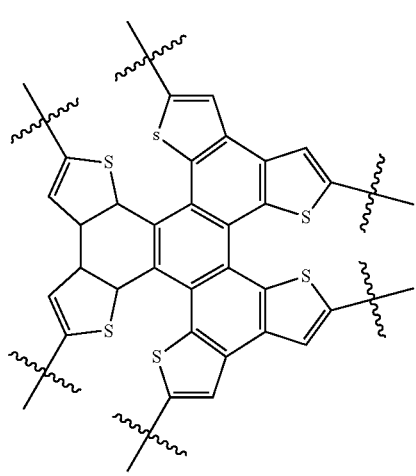
In one aspect, the molecular acceptor is further selected from an acceptor of formula IV:

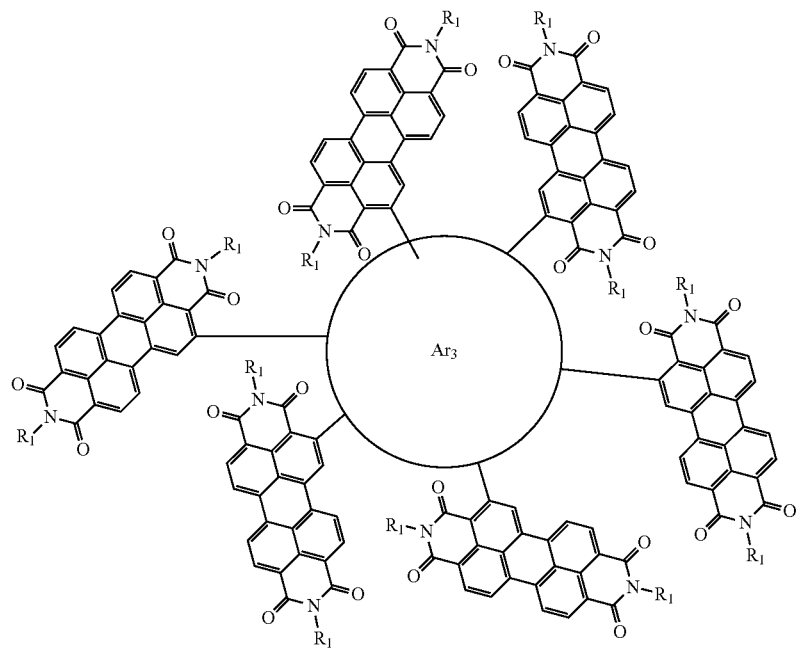
wherein $R^1$ is $C_1$-$C_{30}$ linear or branched chain alkyl; and $Ar^3$ is selected from the group consisting of:
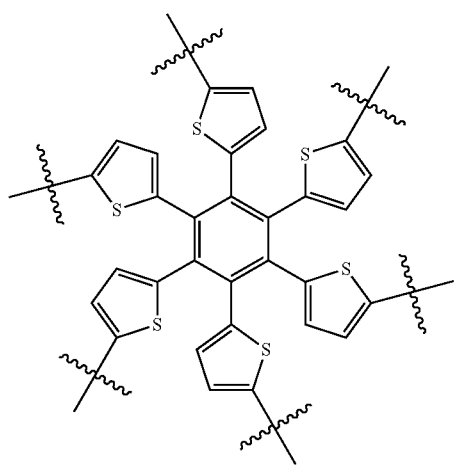
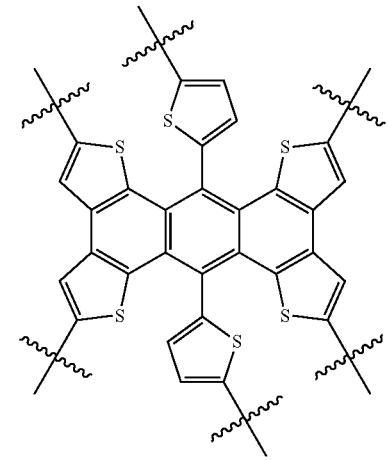
-continued
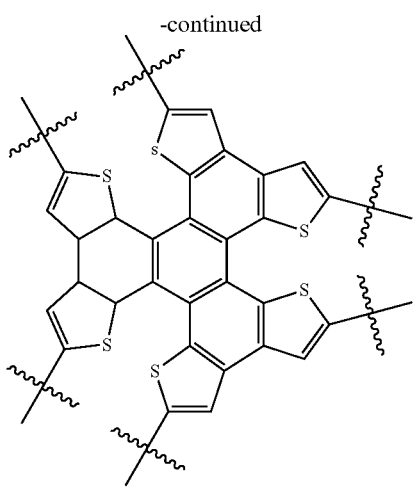
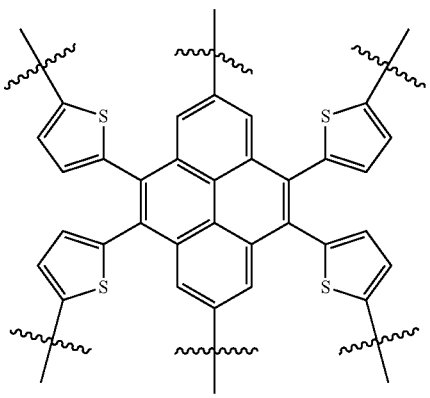
In one embodiment, a semiconducting polymer of formula VIII:

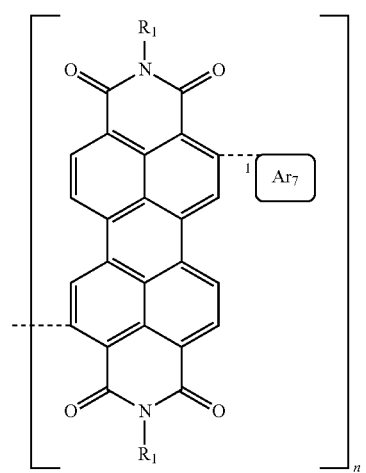
where R¹ is a selected from: $C_1$-$C_{30}$ linear or branched chain alkyl;
n is an integer greater than 1; and
$Ar_7$ is selected from:
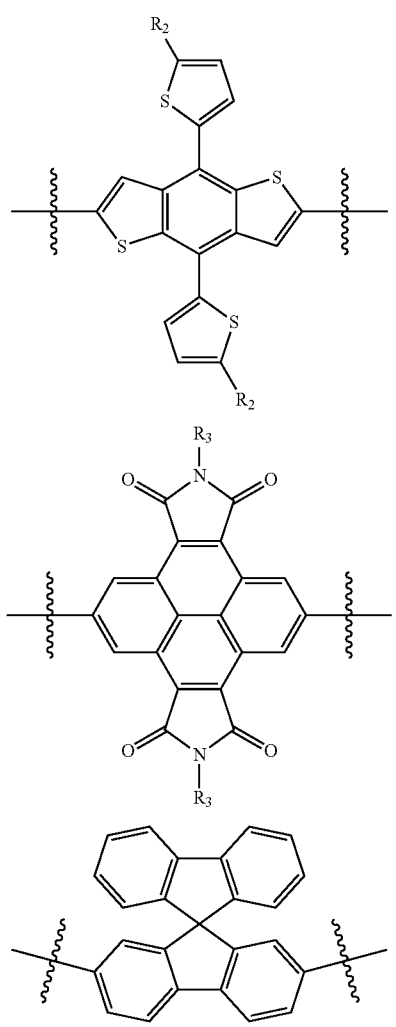
-continued
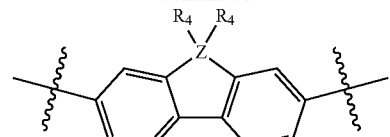
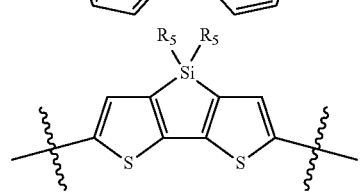
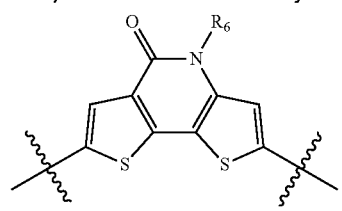
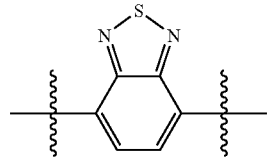
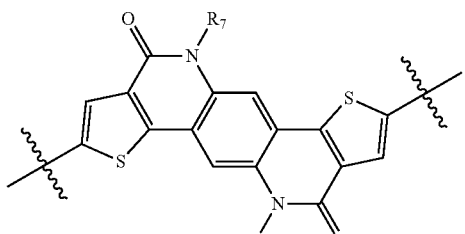
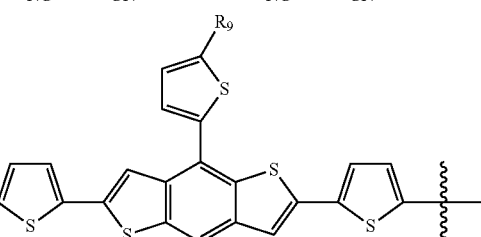
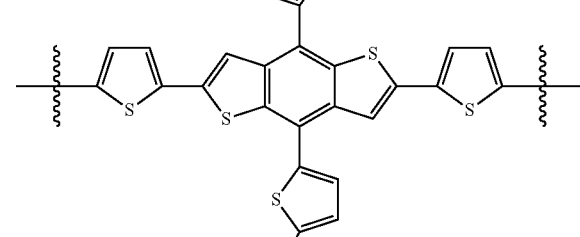
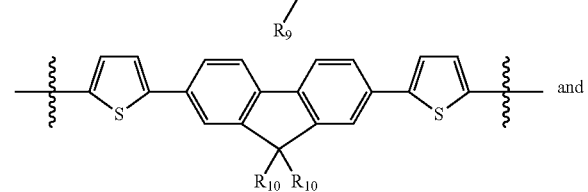 and

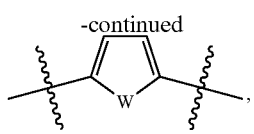

where $R^2$, $R^3$, $R^4$, $R^5$, $R^6$, $R^7$, $R^8$, $R^9$ and $R^{10}$, if present, are each independently selected from: $C_1$-$C_{30}$ linear or branched chain alkyl, and

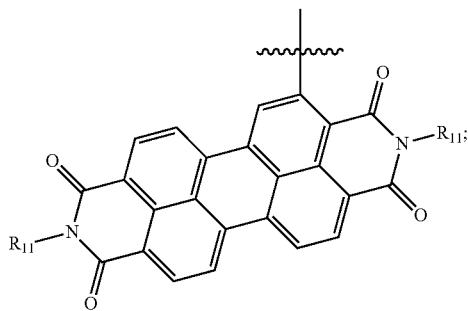

$R^{11}$, if present, is $C_1$-$C_{30}$ linear or branched chain alkyl; W is Se or S; and Z is C or Si.

In some embodiments, $R^1$ and at least one of $R^2$, $R^3$, $R^4$, $R^5$, $R^6$, $R^7$, $R^8$, $R^9$, $R^{10}$ and $R^{11}$ is the same. In some embodiments, $R^1$ and at least one of $R^2$, $R^3$, $R^4$, $R^5$, $R^6$, $R^7$, $R^8$, $R^9$, $R^{10}$ and $R^{11}$ is different. In some embodiments, $R^1$ and at least one of $R^2$, $R^3$, $R^4$, $R^5$, $R^6$, $R^7$, $R^8$, $R^9$, $R^{10}$ and $R^{11}$ is 2-ethylhexyl. In some embodiments, $R^1$ and at least one of $R^2$, $R^3$, $R^4$, $R^5$, $R^6$, $R^7$, $R^8$, $R^9$, $R^{10}$ and $R^{11}$ is 2-butyloctyl. In some embodiments, $R^1$ and at least one of $R^2$, $R^3$, $R^4$, $R^5$, $R^6$, $R^7$, $R^8$, $R^9$, $R^{10}$ and $R^{11}$ is 1-propylbutyl.

In one aspect, a use of a semiconducting acceptor or semiconducting polymer is disclosed and described in a solar cell, an optical device, an electroluminescent device, a photovoltaic cell, a semiconducting cell, or photodiode.

It will be readily apparent to one of ordinary skill in the relevant arts that suitable modifications and adaptations to the compositions, methods, and applications described herein can be made without departing from the scope of any embodiments or aspects thereof. The compounds and methods provided are exemplary and not intended to limit the scope of any of the specified embodiments. All of the various embodiments, aspects, and options disclosed herein can be combined in any and all variations or iterations. The scope of the compounds and methods described herein include all actual or potential combinations of embodiments, aspects, options, examples, and preferences herein described. All patents and publications cited herein are incorporated by reference herein for the specific teachings thereof.

EXAMPLES

Design and Synthesis of Compounds.

The selective functionalization of ortho-position (2,5,8, 11-positions) of PDI by introducing boron, alkyl and aryl substituent are known, by which the optical, electrical, packing and film forming properties of PDI derivatives can be tuned. Evidences exist to demonstrate the minimized perturbation of the planarity of the perylene core due to functionalization at ortho-position of PDI. Furthermore, functional groups in ortho-position exert limited steric hindrance with PDI. Structural analysis with single crystal of NDI-4TH showed that due to the strong interaction between oxygen (C=O in NDI) and proton (C—H in adjacent thiophene), the twisted angle between thiophene ring and NDI core is only 25° which is much smaller than simulated dihedral angle (55-60°) between adjacent thiophene ring and PDI when thiophene attached at bay-position of PDI. Considering the similarity between ortho-position of NDI and PDI, it is safe to assume that connecting aromatic units such as thiophenyl groups at the ortho-position of PDI can significantly increase the coplanarity of the desired compounds that will benefit the electron transporting. Based on these considerations, an a-monobrominated PDI was synthesized as the new building block to electron acceptors. Previously, it was demonstrated that polarity in acceptor polymers is also important to achieve high solar cell efficiency. To compare the effect of polarity, A-D-A and A-wA-A acceptors were developed. The BDT-Th is used as the donor. The pyrene diimide (PID) was successfully synthesized and used as the weak acceptor. This novel five ring diimide allows functionalization at 2,7-positions that are much less stereo-hindered than other diimides such as PDI and NDI.

The α-monobrominated PDI (compound 4, 5) was synthesized in a two-steps one-pot reaction as depicted in FIG. 1. The α-position of PDI was first functionalized with pinacolatoboron (Bpin) group in the modified Ir-catalyzed reaction, developed by Shinokubo and Osuka group. The reaction mixture was treated with $CuBr_2$ without separation. The synthesis of the weaker acceptor PID-2Bpin started from commercially available material 1,2,3,6,7,8-hexahydropyrene, which was brominated with bromine for 30 minutes, yielding 4,5,9,10-tetrabromo-1,2,3,6,7,8-hexahydropyrene. The excessive amount of bromine in the reaction medium can convert 4,5,9,10-tetrabromo-1,2,3,6,7,8-hexahydropyrene to 4,5,9,10-tetrabromopyrene (compound 1) under light. Compound 1 was then converted into compound 2, which is further hydrolyzed into compound 3. Since compounds 1, 2, 3 exhibit poor solubility in common solvent, the crude products were directly used for the next step reaction without further purification. Imidization with alkylamine led to the formation of PID. It was found that reaction of PID with bromine in a $CHCl_3$/$CF_3COOH$/$H_2SO_4$, leads to undesired bromination at 1, 3, 6, 8-positions. Selective functionalization of 2,7-positions of PID with Bpin was realized by a steric controlled Ir-catalyzed reaction. The target compounds, αPPID, βPPID, αPBDT and βPBDT, were synthesized via palladium mediated Stille or Suzuki coupling reaction. These compounds exhibit high solubility in common solvent such as chloroform, chlorobenzene. Their structures were characterized and confirmed with various spectroscopic techniques, which are shown in supporting information.

Electronic and Optical Properties.

Figure 2:
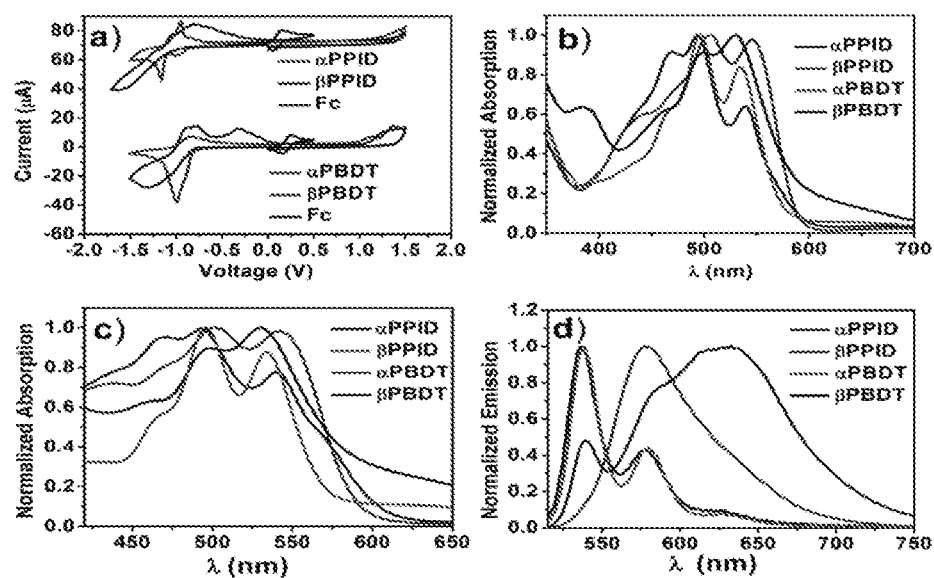
FIG. 2 depicts the cyclic voltammograms, absorption and emission spectra of αPPID, βPPID, αPBDT and βPBDT: a) the film CV; b) solution absorption, c) film absorption, d) solution emission.
Figure 3:
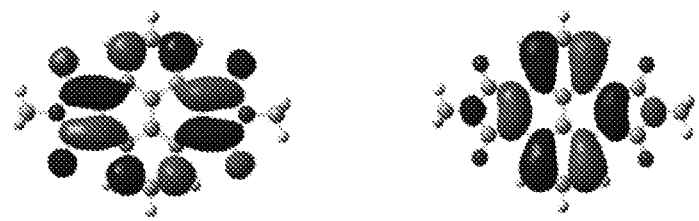
FIG. 3 depicts LUMO (left, −3.00 eV) and HOMO (right, −6.05 eV) orbitals of PID monomer which is simulated with Gaussian b3lyp/6-31gd.

The cyclic voltammetry (CV) is employed to investigate the electrochemical properties of these compounds and is shown in FIG. 2. FIG. 2 describes the cyclic voltammograms (CV), absorption and emission spectra of αPPID, βPPID, αPBDT and βPBDT: a) the film CV; b) solution absorption; c). film absorption; d) solution emission. The LUMO energy levels for different imide building motif were determined to be −3.16 eV for PID, −3.57 eV for NDI and −3.83 eV for PDI, the trend of which is in agreement with that obtained from theoretical calculation (See FIG. 3). FIG. 3 depicts the LUMO (left, −3.00 eV) and HOMO (right, −6.05 eV) orbitals of PID monomer which is simulated with Gaussian b3lyp/6-31gd. Thus, the PID is a weaker acceptor building unit and the electron-withdrawing ability of five-member diimide is weaker than that of six-member diimide. The LUMO and HOMO energy values of the four compounds, αPPID, βPPID, αPBDT and βPBDT, are listed in Table 1.

TABLE 1

Electrochemical and optical data and DFT calculation results of αPPID, βPPID, αPBDT and βPBDT.

| | LUMO (eV) | HOMO (eV) | LUMO (eV)$^{Cal}$ | HOMO (eV)$^{Cal}$ | Dihedral angle (°) | Bay angle (°) | $I^{00}/I^{01}$ sol | $I^{00}/I^{01}$ film | QY (%) |
|---|---|---|---|---|---|---|---|---|---|
| αPPID | −3.84 | −5.86$^a$ | −3.51 | −6.04 | 61.4 | 3.2 | 0.80 | 0.77 | 14 |
| βPPID | −3.79 | −5.87$^a$ | −3.51 | −5.96 | 57.6 | 17.7 | 1.38 | 0.98 | 43 |
| αPBDT | −3.78 | −5.60 | −3.47 | −5.97 | 58.6 | 4.2 | 1.52 | 0.88 | 0.25 |
| βPBDT | −3.76 | −5.64 | −3.46 | −5.53 | 54.4 | 16.8 | 1.33 | 1.11 | 0.01 |

Figure 4:
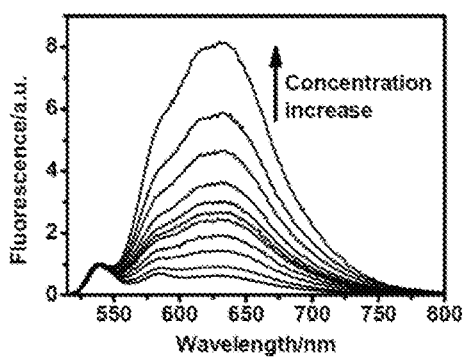
FIG. 4 depicts the concentration dependence fluorescence study of αPPID dissolved in chlorobenzene. Spectra were normalized at 0-0 transition emission peak (535 nm). Concentration was gradually increased from 2.1×10-9 M to 1.0×10-6 M. (Concentration from low to high: $2.1 \times 10^{-9}$ M, $6.3 \times 10^{-9}$ M, $1.9 \times 10^{-8}$ M, $5.6 \times 10^{-8}$ M, $1.1 \times 10^{-7}$ M, $1.7 \times 10^{-7}$ M, $2.5 \times 10^{-7}$ M, $3.8 \times 10^{-7}$ M, $5.7 \times 10^{-7}$ M, $8.0 \times 10^{-7}$ M, $1.0 \times 10^{-6}$ M.)

$^a$The HOMO energy level was calculated by the equation of $E_{HOMO} = E_{LUMO} - E_g^{opt}$ The four compounds show nearly identical LUMO energy levels and the HOMO energy levels of compounds containing PID is slightly lower than those of αPBDT and βPBDT because of the electron-withdrawing nature of PID and electron-donating nature of BDT. The HOMO/LUMO energy levels for the four compounds all matches that of PTB7-Th with enough energy offset for both electron and hole transfer to each other. UV-Vis absorption spectra of the four compounds are recorded both in solution and in solid film (FIGS. 2B, 2C). They all exhibit the three vibronic peaks, resembling to PDI monomer. The β-isomers showed red-shifted band edges, likely due to more extended electron delocalization or more twisted PDI units. However, the absorption peaks for αPPID at 495 nm in solution are stronger than other three compounds and resemble to its film absorption, which suggest a strong tendency of αPPID to form aggregate in the dilute solution. In absorption spectra of films, both α-substituted compounds exhibit stronger 0-1 ($I^{01}$) absorption peak than 0-0 ($I^{00}$) transition, while β-substituted compounds show similar or weaker intensity for 0-1 in solid state than 0-0 transition. The decrease in the ratio of 0-0 to 0-1 transition intensity from solution to solid state for four compounds (blue-shift in absorption maxima) indicates the formation of H-aggregate. The largest decrease of αPBDT implies the strong intermolecular π-π interaction and high packing order of αPBDT, which is beneficial for charge transporting. The quantum yield (QY) for the emission is shown in Table 1. The αPBDT and βPBDT have similar, but weak emission spectra (low QY) which resemble PDI monomer, which may indicate quenching caused by intramolecular charge transfer. The intramolecular charge transfer property also explains the lack of excimer formation in βPBDT and βPBDT. The αPPID and βPPID show the large red shift emission peak. The αPPID also shows a concentration-dependent emission spectrum (See FIG. 4), indicating the formation of excimers, as evidenced by the broad peak at 600-700 nm that coincide with reported PDI excimer. FIG. 4 depicts the concentration dependence fluorescence study of αPPID dissolved in chlorobenzene. Spectra were normalized at 0-0 transition emission peak (535 nm). Concentration was gradually increased from $2.1 \times 10^{-9}$ M to $1.0 \times 10^{-6}$ M. (Concentration from low to high: $2.1 \times 10^{-9}$ M, $6.3 \times 10^{-9}$ M, $1.9 \times 10^{-8}$ M, $5.6 \times 10^{-8}$ M, $1.1 \times 10^{-7}$ M, $1.7 \times 10^{-7}$ M, $2.5 \times 10^{-7}$ M, $3.8 \times 10^{-7}$ M, $5.7 \times 10^{-7}$ M, $8.0 \times 10^{-7}$ M, $1.0 \times 10^{-6}$ M.)

The results indicate that the π-system in αPPID is closed packed due to its good planarity. The excimer emission in αPPID is overlapped with the weak emission from monomeric αPPID. The emission spectrum of βPPID only has one peak at 579 nm which corresponds to 1-0 transition of PDI, which may be due to special electronic features of the twisted PDI core.

DFT Calculation.

In order to gain more insight into the structural and electronic difference between α-substituted and β-substituted PDIs, density functional theory calculations by using the Gaussian package b3lyp/6-31 g(d) were carried out to evaluate the frontier molecular orbitals and structures of the four compounds. To facilitate the calculation, the long alkyl chains are replaced with methyl group. The pictorial presentation of LUMO and HOMO orbitals of the four compounds are shown in the FIG. 1 and the energy levels and torsional angles are summarized in the Table 1. The calculated LUMO and HOMO energy levels of the four compounds are in the same trend with that observed in the CV. For the compounds αPBDT and βPBDT, the LUMO orbitals localize at PDI cores while the HOMO electron density localize at BDT-Th cores, which indicate a significant polarization in the excited state, consistent with the observed low emission quantum efficiency caused by intramolecular charge transfer. However, for the compounds αPPID and βPPID, both LUMO and HOMO electron density are localized at PDI cores, suggesting that PID core has limited contribution to the frontier orbitals. The DFT calculation of PID core (FIG. 3) shows that the frontier orbitals do not spread over 2,7-positions of PID. This may be the reason why the PID core is not involved in the LUMO and HOMO orbitals, merely plays the role of structural linker and electron withdrawing via inductive effect. The torsion angle of PDI backbone at the bay-area is 3.2° for αPPDI and 4.2° for αPBDT, which is much smaller than 17.7° for βPPDI and 16.80 for βPBDT. The dihedral angle between the linker and PDI for a-PDI derivatives is only slightly higher than that for β-isomers according to the calculation. Thus, the good planarity of α-position functionalized PDI could facilitate close packing and enhance electron transporting.

OPV Properties and Active Layer Characterization.

Figure 5:
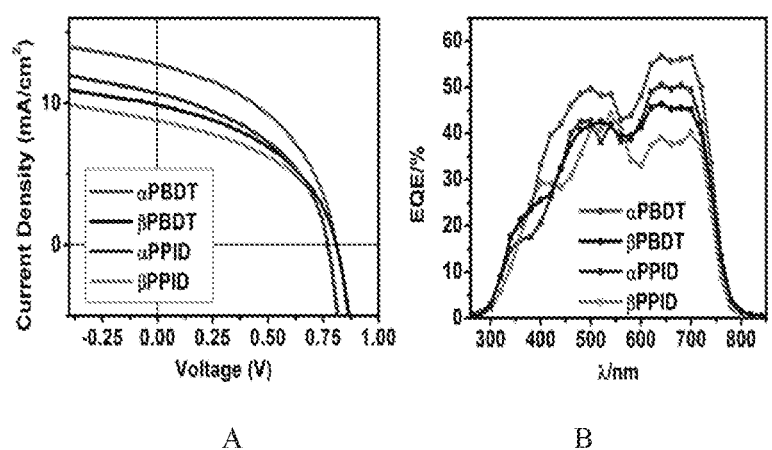
FIG. 5 depicts a) J-V characteristics of solar cell devices using αPPID(red), βPPID(orange), αPBDT(green) and βPBDT(blue) as acceptors and PTB7-Th as donor. b) External quantum efficiency spectra of PTB7-Th with αPPID (red), βPPID(orange), αPBDT(green) and βPBDT(blue).

From the CV studies, the energy levels of these compounds as acceptors match with those of PTB7-Th as donor. The inverted solar cells were prepared with configuration of ITO/ZnO/Active Layer/MoO₃/Al to evaluate the photovoltaic properties of these small molecules. Donor/acceptor ratio of 1:1.5 was spin-casted from hot chlorobenzene with 5% 1-chloronaphthalene as additive and the active layer with the thickness of ~100 nm are formed. FIG. 5 depicts the a) J-V characteristics of solar cell devices using αPPID(red), βPPID(orange), αPBDT(green) and βPBDT(blue) as acceptors and PTB7-Th as donor; and b) External quantum efficiency spectra of PTB7-Th with αPPID(red), βPPID (orange), αPBDT(green) and βPBDT(blue). The above condition to make active layer gives the best OPV performance for all four PDI-based molecules. The J-V characteristics of these OPV cells are shown in Table 2 and J-V curves are plotted in FIG. 5A.

TABLE 2

The parameters summary of solar cell devices with αPPID, βPPID, αPBDT and βPBDT as acceptors and PTB7-Th as donor.

| Acceptor | $J_{sc}$ (mAcm$^{-2}$) | $V_{oc}$ (V) | FF | Eff (%) (best device) | $\mu_e$ (cm$^2$V$^{-1}$ s$^{-1}$) | RMS (pm) |
|---|---|---|---|---|---|---|
| αPPID | 10.15 ± 0.5 | 0.77 ± 0.01 | 0.44 ± 0.01 | 3.49 ± 0.12 (3.61) | 4.46 × 10$^{-4}$ | 738.736 |
| βPPID | 9.14 ± 0.4 | 0.78 ± 0.01 | 0.45 ± 0.01 | 3.20 ± 0.27 (3.47) | 3.48 × 10$^{-4}$ | 732.453 |
| αPBDT | 12.74 ± 0.4 | 0.81 ± 0.01 | 0.46 ± 0.01 | 4.76 ± 0.16 (4.92) | 8.00 × 10$^{-4}$ | 988.090 |
| βPBDT | 9.80 ± 0.3 | 0.81 ± 0.01 | 0.44 ± 0.01 | 3.49 ± 0.04 (3.53) | 4.81 × 10$^{-4}$ | 872.371 |

The device results demonstrate that αPDI based acceptors show very similar Voc with that of βPDI based acceptors if they are connected by the same liker, which is anticipated due to the similarity between their LUMO energy levels. For the BDT linked acceptors, the average PCE of 4.76% for αPBDT is achieved with $J_{sc}$ of 12.74 mA/cm$^2$, $V_{oc}$ of 0.81 V and FF of 0.46, which is 36% higher than that for βPBDT. The PCE enhancement is largely due to much higher $J_{sc}$ (12.74 mA/cm$^2$) values for αPBDT than that (9.80 mA/cm$^2$) for βPBDT. The slightly higher PCE of 3.49% for αPPID than that of 3.20% for βPPID can be attributed to a better intermolecular packing in αPPID than in βPPID. This is consistent with the smaller twisted angle in the αPDI moiety in DFT calculation and the excimer formation in αPPID solution shown by the emission spectrum, which led to a better $J_{sc}$ value of 10.15 mA/cm$^2$ than that (9.14 mA/cm$^2$) for βPPID. These results indicated that acceptors based on αPDI exhibit superior photovoltaic performance over that of βPDI based acceptors. The bottleneck for these devices is the low fill factor value of 0.45±0.01, which is far behind polymer/fullerene devices' values (>0.6). Further device optimization is underway to explore the potential of αPDI-based acceptors.

Figure 7:
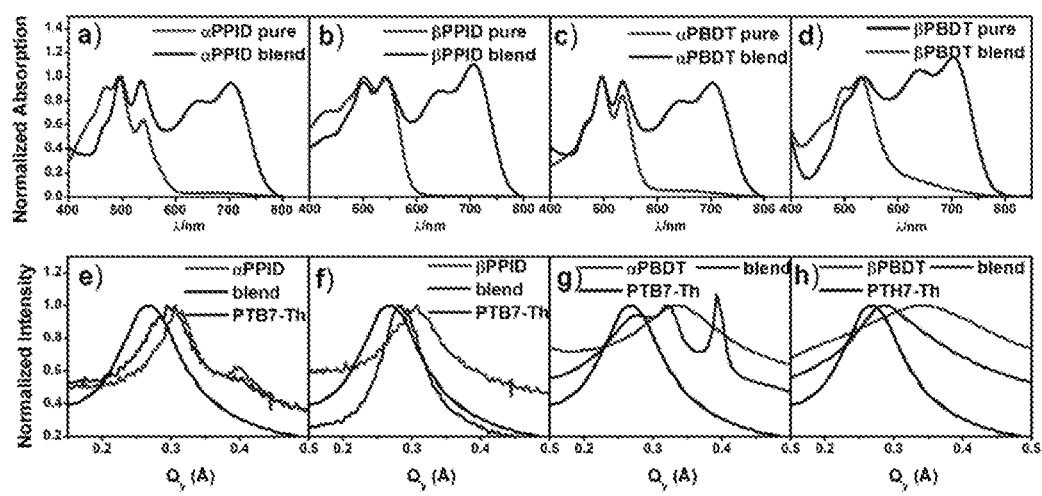
FIG. 7 depicts the absorption spectrum of a) neat αPPID and αPPID/PTB7-Th blend film; b) neat βPPID and βPPID/PTB7-Th blend film; c) neat αPBDT and αPBDT/PTB7-Th blend film; d) neat βPBDT and βPBDT/PTB7-Th blend film. The in-plane 2D GIWAXS patterns of: e) neat PTB7-Th, αPPID and their blend film; f) neat PTB7-Th, βPPID and their blend film; g) neat PTB7-Th, αPBDT and their blend film; h) neat PTB7-Th, βPBDT and their blend film.

The external quantum efficiency (EQE) of the optimal αPPID/βPPID/αPBDT/βPBDT:PTB7-Th devices were measured and are shown in FIG. 5b. The $J_{sc}$ values calculated from EQE all have less than 10% deviation from $J_{sc}$ measured in solar cell device. The results shed some lights on PCE performance of these OPV cells. It can be seen that all of the four devices showed broad EQE spectra from 300 nm to 800 nm. The photon absorption for donor polymer PTB7-Th is between 550 nm to 800 nm. In this region, the quantum efficiency for PTB7-Th blended with α isomers is higher than PTB7-Th blends with related β isomers, indicating more efficient charge separation with α isomers. The quantum efficiency for αPBDT is obviously higher than all others in the whole spectrum. The absorption spectrum of the active layer blends were further measured and recorded in FIG. 7. FIG. 7 depicts the absorption spectrum of a) neat αPPID and αPPID/PTB7-Th blend film; b) neat βPPID and βPPID/PTB7-Th blend film; c) neat αPBDT and αPBDT/PTB7-Th blend film; d) neat βPBDT and βPBDT/PTB7-Th blend film. The in-plane 2D GIWAXS patterns of: e) neat PTB7-Th, αPPID and their blend film; f) neat PTB7-Th, βPPID and their blend film; g) neat PTB7-Th, αPBDT and their blend film; h) neat PTB7-Th, βPBDT and their blend film.

It was found that the absorption spectrum of αPPID and αPBDT in the blend film is very similar with that in pure film. The αPPID and αPBDT not only maintain the two sharp and distinctive perylene diimide's 0-0 and 0-1 vibrational peaks at 540 nm and 495 nm, but also have a shoulder of 0-2 transition at 450 nm. However, in βPPID and βPBDT's blend films, 0-0 and 0-1 transitions are broadened and almost merged with each other, and 0-2 transition totally disappeared, which is different with their pure film absorption spectrum. A possible explanation for this phenomenon is that the αPPID and αPBDT blend films maintain the same packing order as in the pure αPPID and αPBDT domains.

Figure 6:
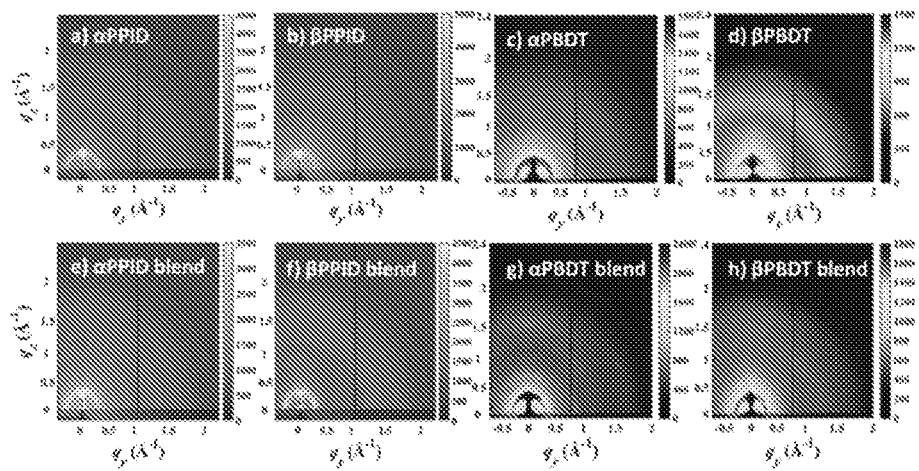
FIG. 6 depicts 2D GIWAXS patterns of films on PEDOT:PSS-modified Si substrates. a-h, 2D GIWAXS patterns of pristine αPPID (a), pristine βPPID (b), pristine αPBDT (c), pristine βPBDT (d), PTB7-TH: αPPID (1:1.5) (e), PTB7-TH: βPPID (1:1.5) (f), PTB7-TH: αPBDT (1:1.5) (g) and PTB7_TH: βPBDT (1:1.5) (h).

The grazing-incidence wide-angle X-ray scattering (GI-WAXS) measurement was employed to investigate the crystallinity of the neat and blend films (FIG. 6). FIG. 6 depicts the 2D GIWAXS patterns of films on PEDOT:PSS-modified Si substrates. a-h, 2D GIWAXS patterns of pristine αPPID (a), pristine βPPID (b), pristine αPBDT (c), pristine βPBDT (d), PTB7-TH: αPPID (1:1.5) (e), PTB7-TH: βPPID (1:1.5) (f), PTB7-TH: αPBDT (1:1.5) (g) and PTB7_TH: βPBDT (1:1.5) (h). The in-plane GIWAXS patterns of neat PTB7-Th, αPPID, βPPID, αPBDT, βPBDT films and their blend films were shown in FIG. 7. The neat films of PTB7-Th, αPPID, βPPID, αPBDT and βPBDT shows the Bragg reflections at qy≈0.27, 0.31, 0.305, 0.34 and 0.34 Å$^{-1}$ corresponding to d-spacing of 23.3, 20.3, 20.6, 18.5 and 18.5 Å, respectively. This peak can be assigned to lateral spacing along the side chains. The βPPID/PTB7-Th and βPBDT/PTB7-Th blend films both exhibit the Bragg reflections at qy≈0.28 Å$^{-1}$ (22.4 Å) that are very close to 0.27 Å$^{-1}$ for the neat donor polymer PTB7-Th. Three diffraction peaks at 0.275 Å$^{-1}$ (22.8 Å), 0.33 Å$^{-1}$ (19.0 Å) and 0.40 Å$^{-1}$ (15.7 Å) was observed for αPBDT/PTB7-Th blend film. The peaks at 0.275 Å$^{-1}$ and 0.33 Å$^{-1}$ are from the diffraction of PTB7-Th and αPBDT, respectively, which implies both pure donor and acceptor domains exist in the blend film. This result is in good agreement with the observation in the absorption spectrum of αPBDT/PTB7-Th blend film. The αPPID/PTB7-Th blend film demonstrates two diffraction peaks at 0.305 Å$^{-1}$ (18.0 Å) and 0.40 Å$^{-1}$ (15.7 Å). The peaks at 0.305 Å$^{-1}$ are most likely from the diffraction of αPPID. However, it is surprising to observe the enhanced sharp peak at qy value of 0.40 Å$^{-1}$. It seems that the polymer/acceptor interaction directed αPBDT to self-assemble in more ordered structures, which may be the reason for observed high electron mobility. The blend film absorption and GIWAXS data both confirm that a isomers of these acceptors (αPPID, αPBDT) maintain the pure domains and the same packing order in the blend films, which may be due to their strong intermolecular interaction resulting from good planarity of a substituted PDI derivative.

The electron mobility of these four devices also help to understand the structure/property relationship, which was measured by space-charge-limited current method with the device structure is ITO/ZnO/PDIs:PTB7-Th/Ca/Al. The electron mobility was calculated to be $4.46 \times 10^{-4}$, $3.48 \times 10^{-4}$, $8.00 \times 10^{-4}$ and $4.81 \times 10^{-4}$ cm$^2$V$^{-1}$ s$^{-1}$ for αPPID, βPPID, αPBDT and βPBDT, respectively, (Summarized in Table 2). It is clear that the αPDI based ones exhibited relatively higher electron mobility than the βPDI based compounds, which is likely the consequence of better planarity of α substituted PDI moieties and stronger intermolecular interaction of αPPID and αPBDT as showed in film absorption spectrum.

Figure 8:
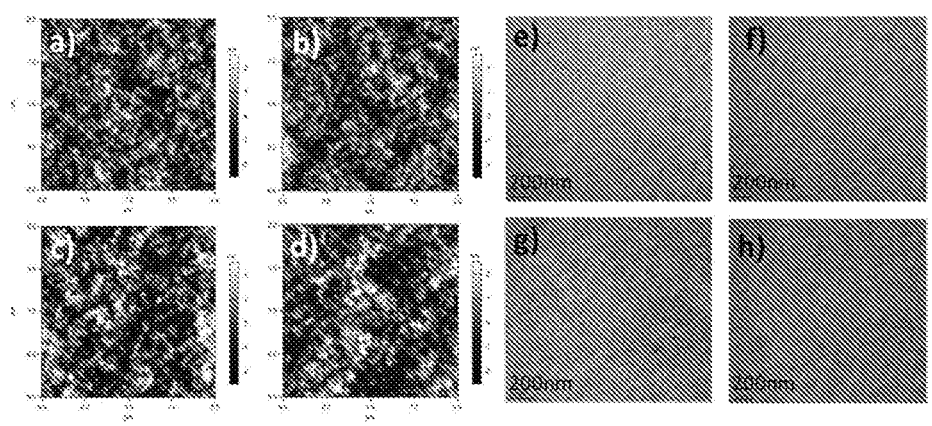
FIG. 8 depicts The atomic force microscopy (AFM) of films of: a) αPPID/PTB7-Th; b) βPPID/PTB7-Th; c) αPBDT/PTB7-Th; d) βPBDT/PTB7-Th. The transmission electron microscopy (TEM) images of the films of: e) αPPID/PTB7-Th; f) βPPID/PTB7-Th; e) αPBDT/PTB7-Th; e) βPBDT/PTB7-Th.

The active blend films of these devices exhibited similar morphology as characterized by atomic force microscopy (AFM) and transmission electron microscopy (TEM) (FIG. 8). AFM height images in FIG. 5 (2 μm×2 μm dimension) show device blends have similar feature and comparatively smooth. Root mean square (RMS) roughness values of αPPID and βPPID blend films are 739 and 732 μm. while the surface for blend films of BDT linked compounds are rougher with RMS value of 872 pm, 988 pm for αPBDT and βPBDT, respectively (Table 2). TEM images of the four blends are also similar, this is probably due to the weak contrast between donor polymer and non-fullerene acceptor. The AFM and TEM studies suggest the solar cell efficiency difference between the four compounds is not resulted from the blend film morphology.

Charge Separation and Recombination Dynamics.

Figure 9:
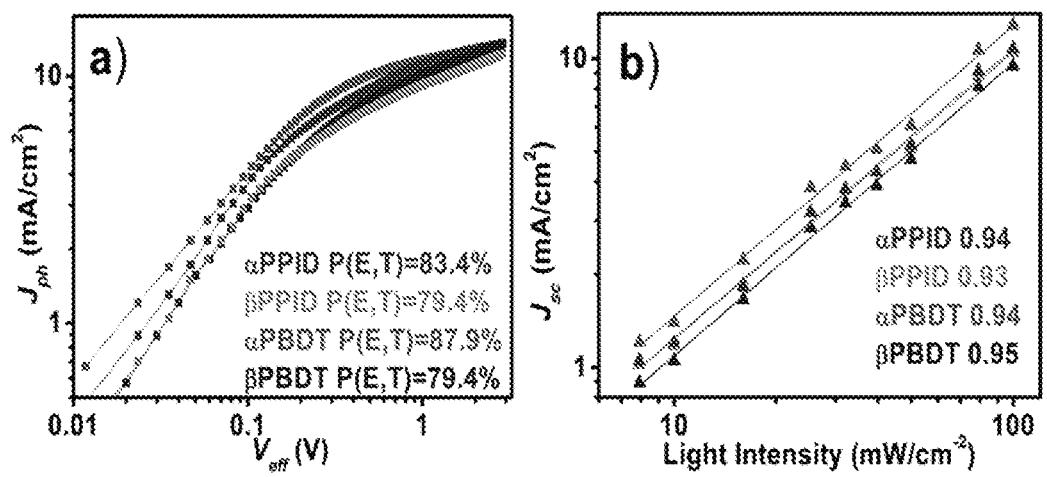
FIG. 9 (a) photocurrent density (Jph) versus effective voltage (Veff) characteristics of the four devices; (b) short current density (Jsc) versus the light density of the four devices.

To better understand the OPV performance, the exciton dissociation and carrier collection process, the charge dissociation probability P(E, T) were investigated according to the reported method. As shown in FIG. 9a, photo current density $J_{ph}$ (defined by $J_L$–$J_D$, $J_L$ and $J_D$ are light and dark current densities) is plotted against effective voltage $V_{eff}$ (defined by $V_0$–V, $V_0$ is voltage where $J_{ph}$=0) in logarithmic scale. Assuming that the $J_{ph}$ reaches its saturation ($J_{sat}$) at high reverse voltage which means all the photogenerated exitons are dissociated to free charge carriers and collected by the electrodes. The P(E, T) is defined as $J_{ph}/J_{sat}$. The calculated P(E, T) under Jsc condition for βPPID and βPBDT are both 79%, while αPPID and αPBDT devices have higher dissociation probabilities of 83% and 88%. The higher P(E,T) values of αPPID and αPBDT indicate the more efficient exciton dissociation at interfaces between αPDI based compounds and PTB7-Th which is in good agreement with higher $J_{sc}$ values of αPPID and αPBDT based devices. In order to gain more insight into the recombination kinetics, the measurement of the $J_{sc}$ as a function of illumination intensity were carried out according to literature. In FIG. 9b, the linear scaling of photocurrent to light intensity was observed for all four devices and the exponential factors for αP-PID:PTB7-Th, βPPID:PTB7-Th, αPBDT:PTB7-Th, βPBDT:PTB7-Th devices are 0.95, 0.94, 0.93 and 0.95, respectively. The high and similar values mean that the bimolecular recombination in the four devices is all comparatively weak, which is consistent with their high electron mobility.

In summary, four electron deficient compounds were synthesized and investigated as electron acceptor in BHJ OPV cells. Detailed studies revealed that the αPPID and αPBDT exhibit planarity in the PDI core which benefits the close π-π stacking. The absorption spectra αPPID and αPBDT showed the strong tendency to form aggregate due to the strong intermolecular π-π interaction, which persists in blended films, leading to relatively high electron mobility. The inverted BHJ devices employing PBT7-Th as the donor and αPDI-based compounds as acceptor demonstrate superior photovoltaic performance than that using βPDI derivative as acceptor; an enhancement of 39% was observed. The higher PCE of αPPID and αPBDT are mainly ascribed to their higher SCLC mobility and the more efficient charge separation at interfaces with PBT7-Th. The results suggest that α-substituted PDI derivatives are indeed promising electron acceptors and further exploration is underway to fulfill the potential of αPDI-based acceptors.

Synthesis and Properties of Example Compounds

Compound 1

Figure 10:
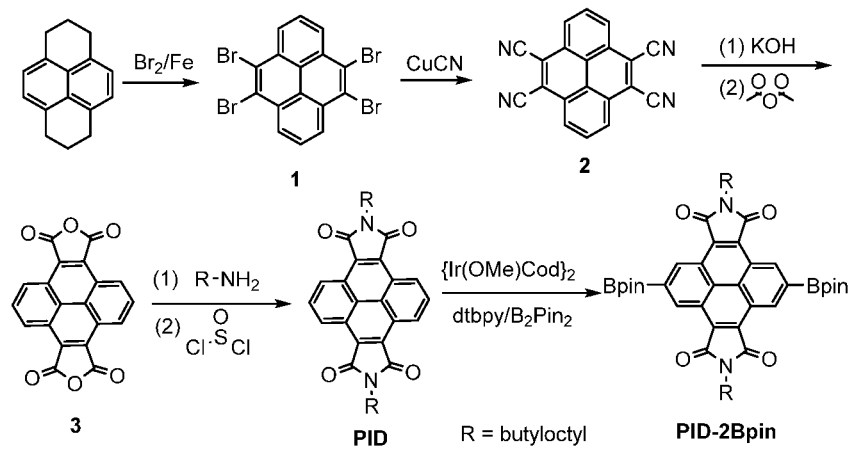
FIG. 10 depicts the synthesis procedure for compounds 1, 2, 3, PID and PID-2Bpin.

FIG. 10 describes synthesis of compound 1. 1,2,3,6,7,8-hexahydropyrene (3.12 g), Bromine (27.17 g), iron powder (0.59 g) and 100 ml dichloromethane were added to a 250 mL round bottom flask and refluxed overnight. The precipitate was filtered and washed with acetone (3×200 ml) and boiling chloroform (3×200 ml). 6.52 g 4,5,9,10-tetrabromopyrene was obtained in the yield of 84%. MS (MALDI-TOF) m/z: 518.15 (M+H)$^+$.

Compounds 2 and 3

FIG. 10 describes synthesis of compounds 2 and 3. 4,5,9,10-tetrabromopyrene (6.20 g), CuCN (8.60 g) and anhydrous NMP were added to a 250 mL round bottom flask under nitrogen atmosphere and reacted at 200° C. for 2 hours. After cooling down, the solution was poured into saturated ammonium. The precipitate was filtered and washed with ammonium, acetone and boiling chloroform. Without further purification, the insoluble solid was added to the KOH (13.5 g) solution in HOCH$_2$CH$_2$OH (60 mL) and water (15 mL) and heated to 160 for 48 hours. After cooling down to 0, concentrated hydrochloric acid were added dropwise to pH=1. The precipitate was filtered and washed with water and acetone. The obtained crude product was refluxed in acetic anhydrate (60 ml) overnight. 0.65 g yellow product was obtained by filtration. The yield for three-step reactions is 15.8%. The compound 2 sparingly dissolve in the common solvent.

Compound PID

FIG. 10 describes synthesis of compound PID. 0.34 g compound 2 and 0.56 g 2-butyloctylamine in 20 ml anhydrous toluene was heated to reflux for 5 hours. After removing the solvent under reduced pressure, the reaction mixture was added thionyl chloride (5 ml) and refluxed for 2 hours. The thionyl chloride was removed under reduced pressure. The crude product was purified by column chromatography, using dichloromethane as the eluent. 0.51 g compound 3 was obtained (yield: 76%). $^1$H NMR (400 MHz, CDCl$_3$) (ppm): 9.49 (d, J=80 Hz, 4H), 8.28 (T, J=80 Hz, 2H), 3.74 (d, J=72 Hz, 4H), 2.0 (m, 2H), 1.35 (br, 32H), 0.90 (br, 12H). $^{13}$C NMR (500 MHz, CDCl$_3$) 14.096, 14.127, 22.663, 23.072, 26.391, 28.607, 29.707, 31.276, 31.618, 31.861, 37.328, 42.367, 124.484, 126.721, 128.244, 128.715, 128.810, 169.792. MS (MALDI-TOF) m/z: 677.13 (M+H)$^+$.

Compound PID-2Bpin

FIG. 10 describes synthesis of compound PID-2Bpin. {Ir(OMe)Cod}(33 mg), 4,4'-di-tert-butyl-2,2'-dipyridyl (66 mg) and (BPin)$_2$ (64 mg) were mixed in 20 ml anhydrous hexane under N$_2$ atmosphere. Then the mixture were transfer to sealed tube which contains compound 3 (0.338 g) and (BPin)$_2$ (0.254 g). After reacting at 120° C. for 24 hours, the solvent was removed under reduced pressure. 0.288 g of pure compound 4 (62%) was obtained by column chromatography, using dichloromethane as the eluent. $^1$H NMR (400 MHz, CDCl$_3$) (ppm): 9.86 (s, 4H), 3.76 (d, J=72 Hz, 4H), 2.0 (m, 2H), 1.50 (s, 24H) 1.35 (br, 32H), 0.88 (br, 12H). $^{13}$C NMR (500 MHz, CDCl$_3$) 14.102, 14.179, 22.660, 23.122, 25.133, 26.605, 28.872, 29.776, 31.420, 31.756, 31.918, 37.388, 42.662, 84.636, 123.678, 128.034, 129.296, 132.428, 169.447. MS (MALDI-TOF) m/z: 929.97 (M+H)$^+$.

Compound QH0267

Figure 11:
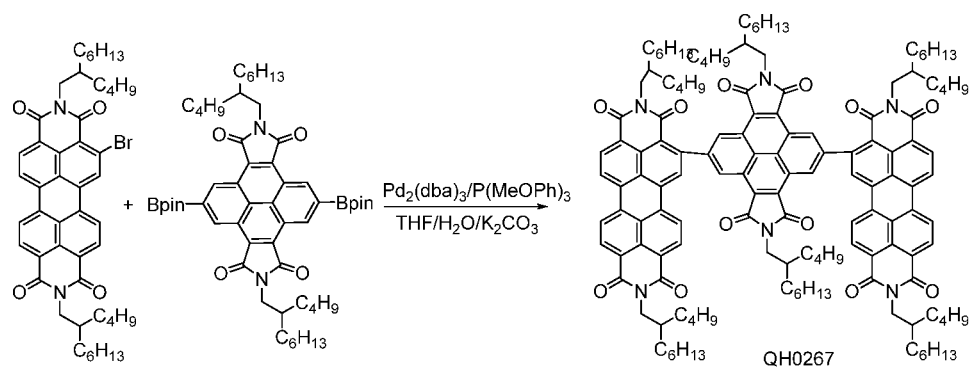
FIG. 11 depicts the synthesis procedure for compound QH0267.

FIG. 11 describes synthesis of compound QH0267. Pd$_2$(dba)$_3$ (9 mg) and P(MeOPh)$_3$ was added to the mixture of 2-BrPDI (104 mg), compound PID-2Bpin (60 mg), THF (8 mL) and 2M K$_2$CO$_3$ aqueous solution (2 mL) under nitrogen. After refluxing overnight, the mixture was poured into methanol. The red precipitate was filtered and purified by column chromatography, using chloroform as the eluent. 104 mg of pure PBDT (76%) was obtained. $^1$H NMR (400 MHz, CDCl$_2$CDCl$_2$) (ppm): 9.37-9.72 (br, 4H), 8.98-7.73 (br, 14H), 4.36-3.71 (br, 12H), 2.20-1.98 (br, 6H), 1.33 (br, 96H), 0.90 (br, 36H). MS (MALDI-TOF) m/z: 2125.82 (M$^+$) Anal. Calcd for C$_{140}$H$_{168}$N$_6$O$_{12}$: C, 79.06; H, 7.96; N, 3.95. Found: C, 79.49; H, 8.14; N, 4.05.

Compound QH0290

Figure 12:
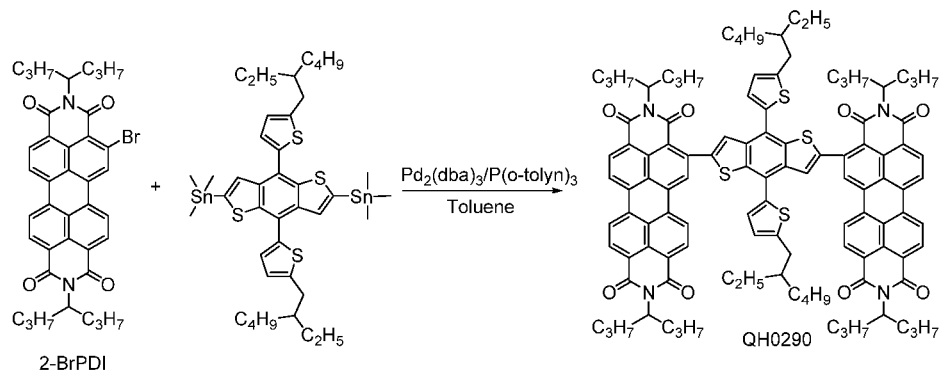
FIG. 12 depicts the synthesis procedure for compound QH0290.

FIG. 12 describes synthesis of compound QH0290. Pd$_2$(dba)$_3$ (9 mg) and P(o-tolyn)$_3$ (24 mg) was added to the mixture of compound 2-BrPDI (133 mg), BDT-2Sn (90.5 mg) and dry toluene (6 mL) under nitrogen. After refluxing overnight, the mixture was poured into methanol. The dark red precipitate was filtered and purified by column chromatography, using chloroform as the eluent. 139 mg of pure □-PPBDT (80%) was obtained. $^1$H NMR (400 MHz, CDCl$_2$CDCl$_2$) (ppm): 8.74-8.69 (br, 14H), 7.86 (s, 2H), 7.51 (br, 2H), 6.91 (br, 2H), 5.21-5.11 (br, 4H), 2.83 (br, 4H), 2.24 (br, 16H), 1.85 (br, 16), 1.65 (br, 2), 1.35 (br, 32H), 0.90 (br, 36H). MS (MALDI-TOF) m/z: 1746.58 (M$^+$) Anal. Calcd for C$_{110}$H$_{114}$N$_4$O$_8$S$_4$: C, 75.57; H, 6.57; N, 3.20. Found: C, 75.86; H, 6.54; N, 3.34.

Compound QH0311

Figure 13:
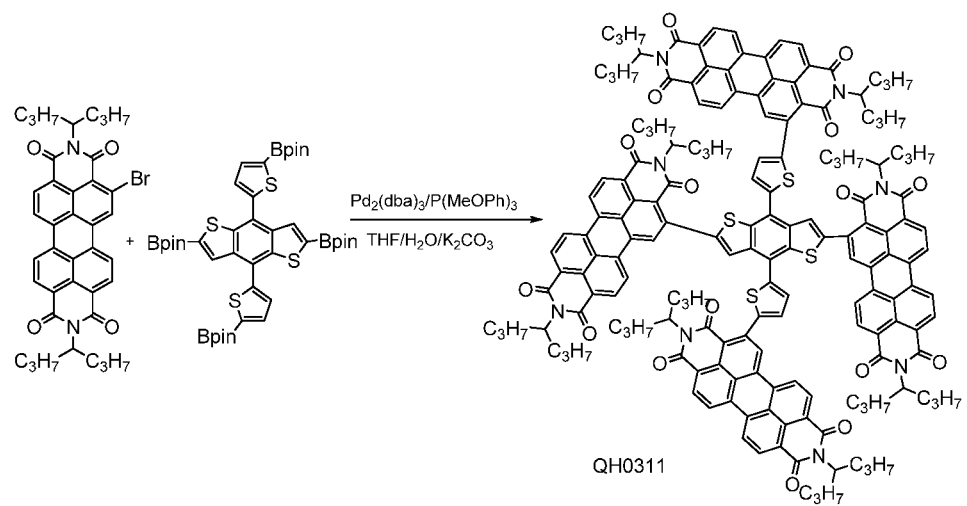
FIG. 13 depicts the synthesis procedure for compound AH0311.

FIG. 13 describes synthesis of compound QH0311. Pd$_2$(dba)$_3$ (9 mg) and P(MeOPh)$_3$ was added to the mixture of 2-BrPDI (419.3 mg), compound BDT-4Bpin (128.7 mg), THF (12 mL) and 2M K$_2$CO$_3$ aqueous solution (3 mL) under nitrogen. After refluxing overnight, the mixture was poured into methanol. The red precipitate was filtered and purified by column chromatography, using chloroform as the eluent. 152 mg of pure TPBDT (39%) was obtained. $^1$H NMR (400 MHz, CDCl$_2$CDCl$_2$) (ppm): 8.63-9.75 (br, 28H), 8.10 (br, 2H), 7.96 (br, 2H), 7.59 (br, 2H), 5.03-5.22 (br, 8H), 2.25 (br, 16H), 1.80 (br, 16H), 1.30 (br, 32H), 0.89 (br, 48H). MS (MALDI-TOF) m/z: 2691.506 (M$^+$).

Polymer QH0327

Figure 14:
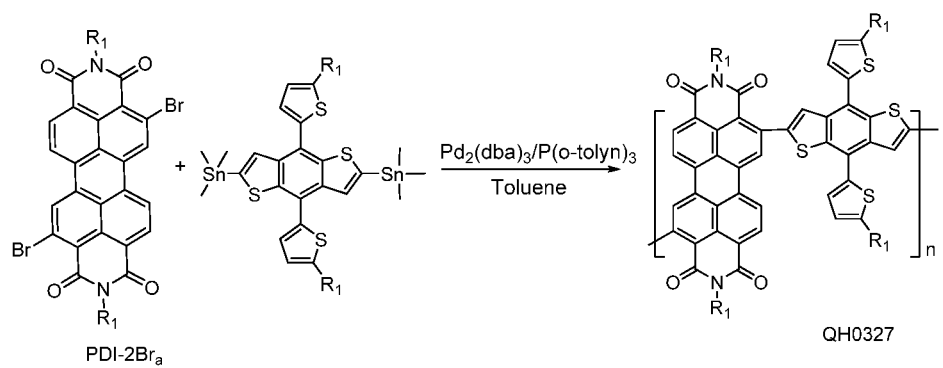
FIG. 14 depicts the synthesis procedure for polymer QH0327.

FIG. 14 describes synthesis of compound QH03271. Pd(PPh$_3$)$_4$ (3.5 mg) and was added to the mixture of compound PDI-2Br$_\alpha$ (77.65 mg), BDT-2Sn (63.32 mg) 0.75 mL DMF and dry toluene (3 mL) under nitrogen. After refluxing overnight, the mixture was poured into methanol. The dark red precipitate was filtered. The resulting solid was subjected to Soxhlet extraction successively with methanol, acetone, and hexane. The remaining polymer was extracted with chloroform and precipitated again from methanol, filtered, washed with methanol, and dried under vacuum. 72 mg dark-red (67.3%) PPBDT was obtained. Number-average molecular weight (Mn): 37.4 kDa; Weight-average molecular weight (Mw): 67.9 kDa; Polydispersity index (PDI): 1.82.

Compounds TPSE, TPC and TPSI.

Figure 25:
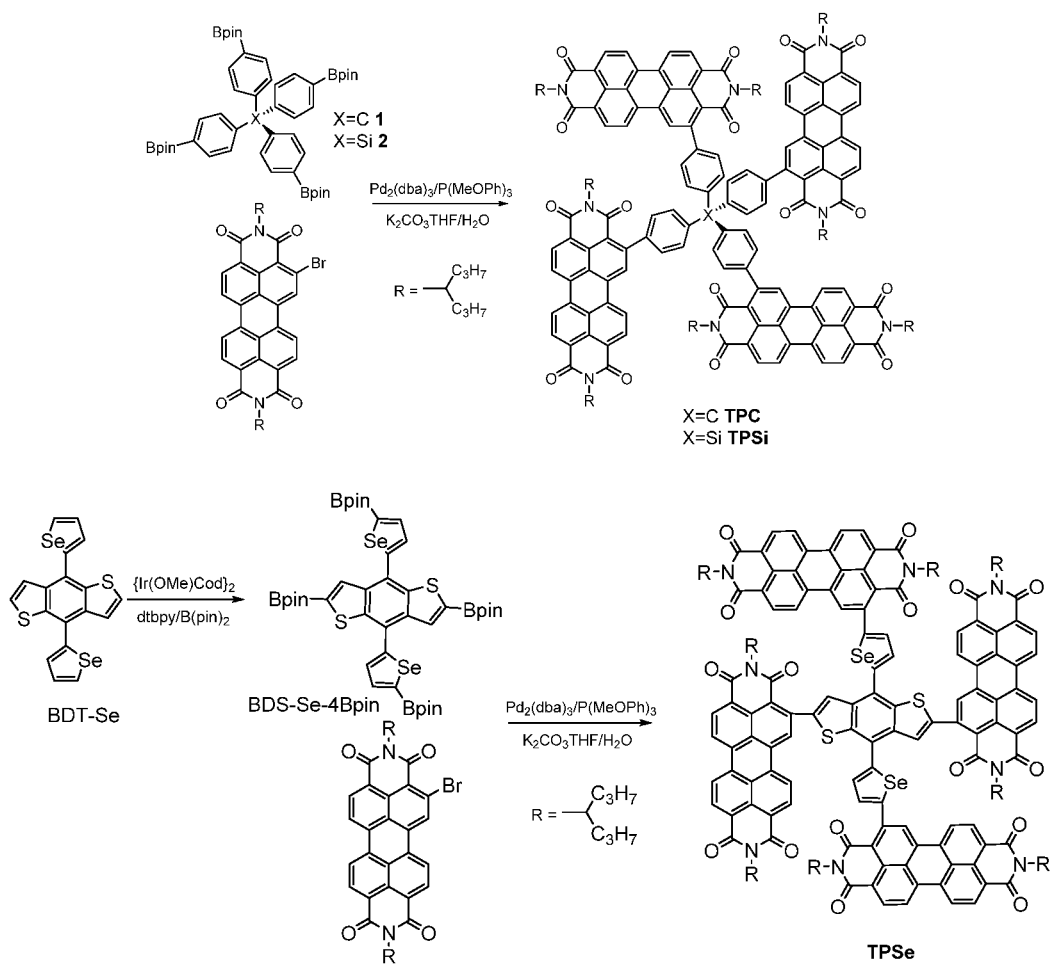
FIG. 25 depicts the general synthetic procedure for TPC, TPSi and TPSe

FIG. 25 describes the synthesis of compounds TPSE, TPC and TPSI. Compound BDT-Se-4Bpin. 25 ml anhydrous hexane were added to a mixture of BDT-Se (0.448 g, 1.0 mmol), (BPin)$_2$ (1.52 g, 6.0 mmol), {Ir(OMe)Cod} (40 mg, 0.06 mmol) and 4,4'-di-tert-butyl-2,2'-dipyridyl (81 mg, 0.3 mmol) in 100 mL sealed tube. After reacting at 120° C. for 48 hours under N$_2$ atmosphere, the solvent was removed under reduced pressure. 0.71 g of pure compound BDT-Se-4Bpin (74.6%) was obtained by recyrstalization in hexane and methanol. $^1$H NMR (400 MHz, CDCl$_3$) δ (ppm): 8.09 (s, 2H), 8.02 (d, J=36 Hz, 2H), 7.71 (d, J=36 Hz, 2H), 1.39 (s, 24H), 1.33 (s, 24H). $^{13}$C NMR (500 MHz, CDCl$_3$) δ 24.78, 24.83, 84.26, 84.56, 126.93, 132.41, 133.41, 137.87, 139.88, 142.28, 151.91; MS (MALDI-TOF) m/z=982.18 (M$^+$); HRMS (ESI) m/z calcd for [C$_{42}$H$_{54}$B$_4$O$_8$S$_4^+$] 592.2298, found 592.2221.

General synthetic procedure for TPC, TPSi and TPSe. Pd$_2$(dba)$_3$ (0.01 mmol) and P(MeOPh)$_3$ (0.08 mmol) was added to the mixture of compound 1, 2 or BDT-Se-4Bpin (0.1 mmol), compound PDI-Br$^\alpha$ (0.42 mmol), THF (10 mL) and 2M K$_2$CO$_3$ aqueous solution (2.5 mL) under nitrogen. After refluxing 16 hours, the mixture was poured into methanol. The red precipitate was filtered and purified by column chromatography, using chloroform/dichloromethane=⅓ as the eluent.

Compound TPC. TPC was obtained in yield of 71.3%. $^1$H NMR (400 MHz, CDCl$_3$) δ (ppm): 8.77-8.55 (m, 28H), 7.74 (d, J=84 Hz, 8H), 7.57 (d, J=84 Hz, 8H), 5.12-5.22 (Br, 8H), 2.24 (Br, 16H), 1.78 (Br, 16H), 1.31-1.36 (Br, 32H), 0.90 (Br, 48H). MS (MALDI-TOF) C$_{177}$H$_{164}$N$_8$O$_{16}$ m/z: 2659.30; Found: 2659.05 (M)$^+$ HRMS (ESI) m/z calcd for [C$_{177}$H$_{164}$N$_8$O$_{16}^+$] 2659.2337, found 2659.2398.

Compound TPSi. TPSi was obtained in yield of 78.2%. $^1$H NMR (400 MHz, CDCl$_3$) δ (ppm): 8.78-8.52 (m, 28H), 8.06 (d, J=80 Hz, 8H), 7.63 (d, J=80 Hz, 8H), 5.12-5.22 (Br, 8H), 2.23 (Br, 16H), 1.81 (Br, 16H), 1.32 (Br, 32H), 0.90 (Br, 48H). MS (MALDI-TOF) C$_{176}$H$_{164}$N$_8$O$_{16}$Si m/z: 2675.37; Found: 2675.01 (M)$^+$ HRMS (ESI) m/z calcd for [C$_{176}$H$_{164}$N$_8$O$_{16}$Si+H]$^+$ 2676.2107, found 2676.2161.

Compound TPSe. TPSe was obtained in yield of 76.5%. $^1$H NMR (400 MHz, CDCl$_3$) δ (ppm): 8.75-8.63 (m, 28H), 8.10 (Br, 2H), 7.96 (Br, 2H), 7.59 (Br, 2H), 5.02-5.22 (Br, 8H), 2.25 (Br, 16H), 1.81 (Br, 16H), 1.32-0.86 (Br, 80H). MS (MALDI-TOF) C$_{170}$H$_{154}$N$_8$O$_{16}$S$_2$Se$_2$ m/z: 2786.93; Found: 2787.77 (M+H)$^+$ HRMS (ESI) m/z calcd for [C$_{170}$H$_{154}$N$_8$O$_{16}$S$_2$Se$_2$+H]$^+$ 2787.9446, found 2787.9376.

Compounds βTPB6 and βTPB6-C.

Figure 26:
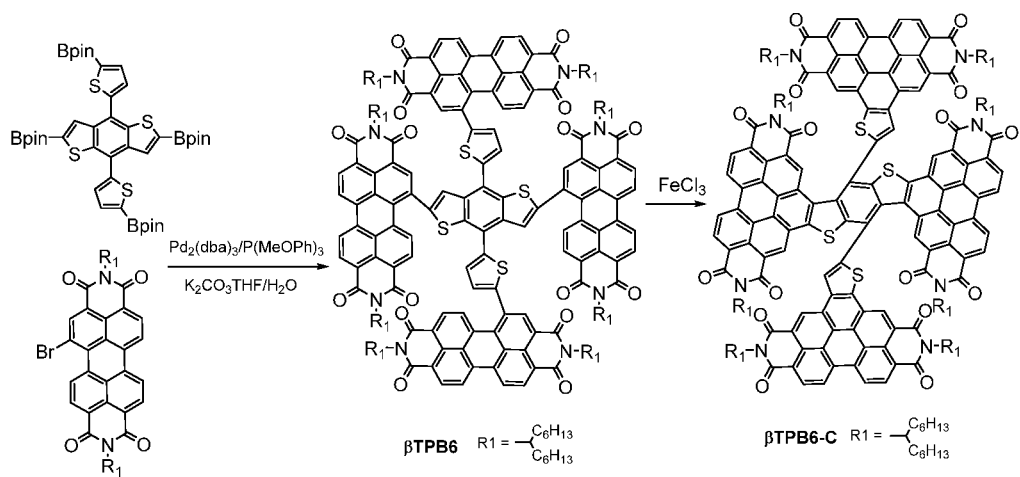
FIG. 26 depicts the general synthetic procedure for βTPB6-C.

FIG. 26 describes the synthesis of compounds βTPB6 and βTPB6-C.

Compound βTPB6. Pd2(dba)3 (25 mg) and P(MeOPh)3 (75 mg) was added to the mixture of compound BDT-Th-4Bpin (107.3 mg), compound PDI-Br$^\beta$ (437.8 mg), THF (12 mL) and 2M K2CO3 aqueous solution (3 mL) under nitrogen. After refluxing overnight, the mixture was poured into methanol. The red precipitate was filtered and purified by column chromatography, using dichloromethane/hexane=1:1 as the eluent. 256 mg of pure βTPB6 (73.8%)

was obtained. $^1$H NMR (500 MHz, CDCl$_3$) δ (ppm): 8.86-8.68 (Br, 33H), 8.57 (Br, 4H), 8.06-8.12 (Br, 4H), 7.61 (Br, 2H), 7.28 (Br, 2H), 5.19-4.71 (Br, 8H), 2.12 (Br, 16H), 1.86 (Br, 16H), 1.18-0.75 (Br, 176H). MS (MALDI-TOF) C$_{218}$H$_{250}$N$_8$O$_{16}$S$_4$ m/z: 3363.79; Found: 3364.22 (M+H)+ Anal. Calcd for C218H250N8O16S4: C, 77.77%; H, 7.49%; N, 3.33%. Found: C, 77.54%; H, 7.43%; N, 3.19%.

Compound βTPB6-C. FeCl$_3$ (1 g) in 3 mL CH$_3$NO$_2$ was added to 6 mL CH$_2$Cl$_2$ solution of βTPB6 (100 mg) at 0° C. After one hour stirring at room temperature, 10 mL 1 M hydrochloride was added. The organic part was separated and the solvent was removed under reduced pressure. The product was purified by column chromatography, using dichloromethane/hexane=1:1 as the eluent. 61 mg of pure βTPB6 (61.1%) was obtained $^1$H NMR (500 MHz, CDCl$_2$CDCl$_2$) δ (ppm): 11.78 (Br, 2H), 10.18 (Br, 2H), 9.51-9.07 (Br, 18H), 8.76 (Br, 4H), 5.43-4.61 (Br, 8H), 2.06-0.73 (Br, 176H). MS (MALDI-TOF) C$_{218}$H$_{242}$N$_8$O$_{16}$S$_4$ m/z: 3355.73; Found: 3355.43 (M)+Anal. Calcd for C218H242N8O16S4: C, 77.96%; H, 7.26%; N, 3.34%. Found: C, 77.65%; H, 7.03%; N, 3.35%.

Electronic and Optical Properties.

Figure 15:
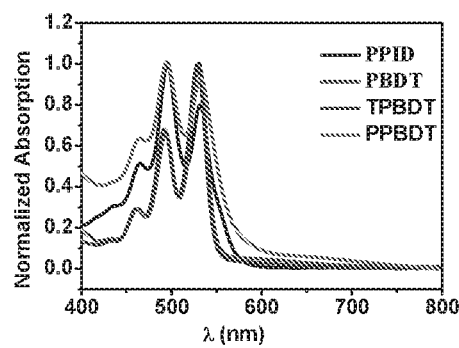
FIG. 15 depicts the solution absorption spectra of PPID, PBDT, TPBDT and PPBDT.

The LUMO energy levels were calculated from the cyclic voltammetry (CV). The LUMO energy levels of PPID (QH0267), PBDT (QH0290), TPBDT (QH0311) and PPBDT (QH0327) are −3.84, −3.78, −3.89 and −3.88 eV respectively. The HOMO energy levels of PPID, PBDT, TPBDT and PPBDT are −5.86, −5.60, −5.71 and −5.60 eV respectively. The HOMO/LUMO energy levels for the four compounds all matches that of PTB7-Th with enough energy offset for both electron and hole transfer to each other. The solution absorption spectra of PPID, PBDT, TPBDT and PPBDT are shown in FIG. 15. The photon absorption for these compounds are between 450 nm to 580 nm while the absorption of the donor polymer PTB7-Th is between 550 nm to 780 nm. The well matched absorption in the sun light spectrum can make more photon be harvested and translate to electricity.

Solar Cell Device Characterization

Figure 16:
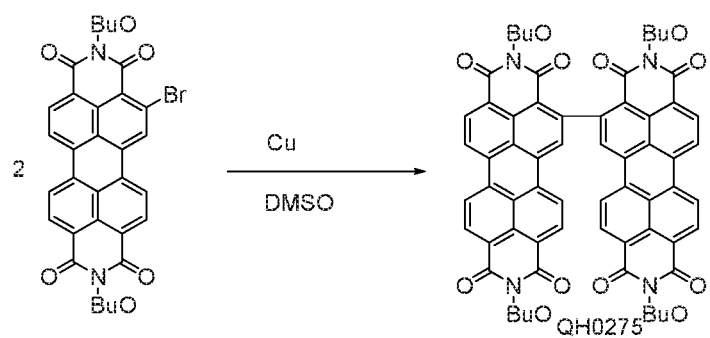
FIG. 16 depicts the synthesis procedure for compound QH0275.
Figure 17:
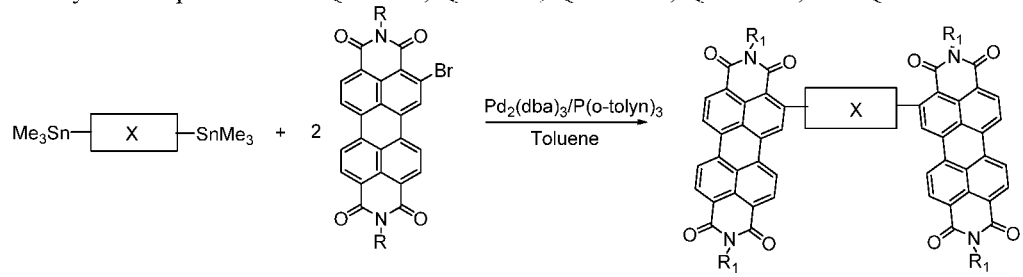
FIG. 17 depicts the synthesis protocol for QH0289, QH0290, QH2106, QH02111, and QH02136.
Figure 18:
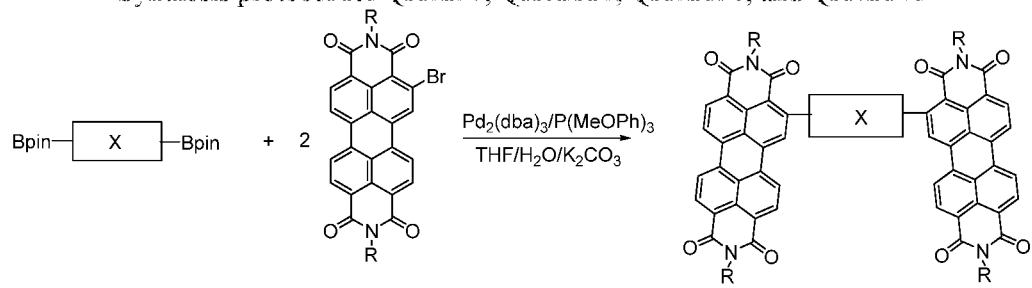
FIG. 18 depicts the synthesis protocol for QH0297, QH02120, QH02138, QH02141.

Part 1. Small molecules, PDI-X-PDI, X can be a linker or nothing. Syntheses of the compounds described in FIGS. 11, 16-17.

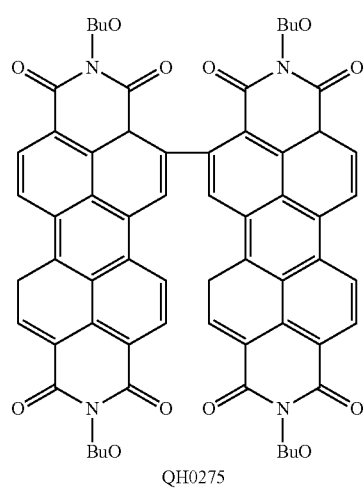

QH0275

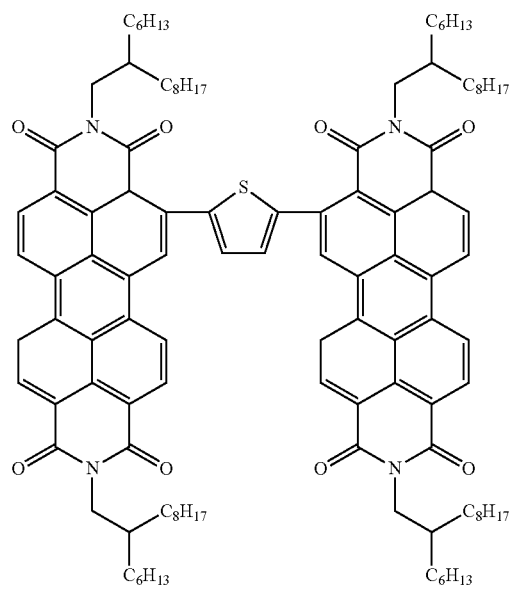

Properties of Compounds of Part 1.

|  | Jsc (mA/cm$^{-2}$) | Voc (V) | FF | PCE (%) |
| --- | --- | --- | --- | --- |
| QH0267 | 10.20 | 0.78 | 0.45 | 3.61 |
| QH0275 | 1.82 | 0.17 | 0.27 | 0.08 |
| QH0289 | 4.90 | 0.54 | 0.32 | 0.85 |
| QH0290 | 12.99 | 0.81 | 0.47 | 4.95 |
| QH0297 | 4.27 | 0.63 | 0.25 | 0.67 |
| QH02106 | 8.25 | 0.79 | 0.37 | 2.44 |
| QH02111 | 5.64 | 0.73 | 0.33 | 1.36 |
| QH02120 | 11.85 | 0.85 | 0.47 | 4.69 |
| QH02136 | 8.96 | 0.80 | 0.48 | 3.43 |
| QH02138 | 5.65 | 0.73 | 0.40 | 1.66 |
| QH02141 | 7.78 | 0.77 | 0.37 | 2.24 |

Figure 19:
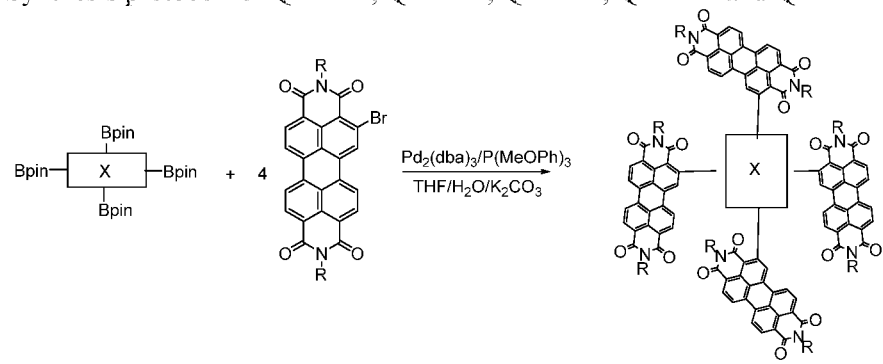
FIG. 19 depicts the synthesis protocol for QH0311, QH0306, QH0318, QH0315.

Part 2. Small molecules, (PDI)$_4$X. Syntheses of the compounds is described in FIG. 19.

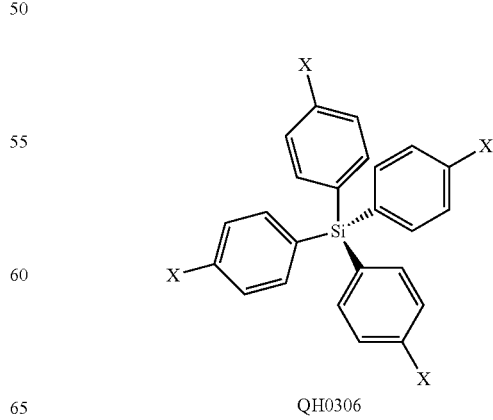

QH0306

-continued
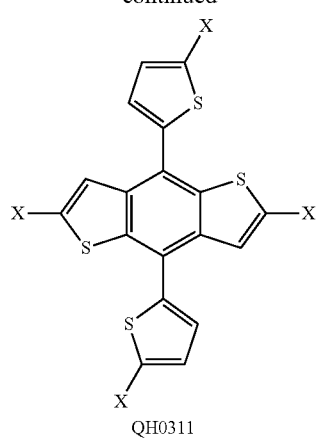
QH0311
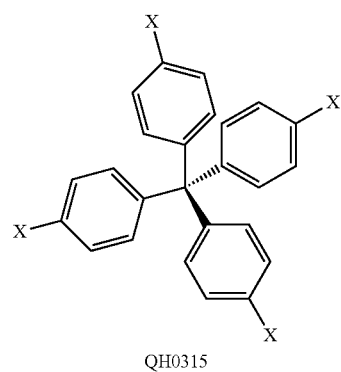
QH0315
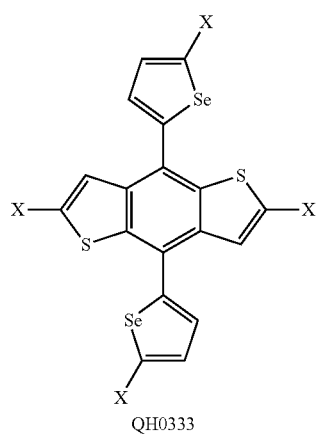
QH0333
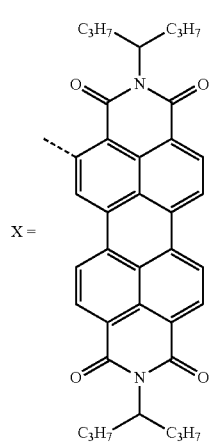
X =
Properties of compounds of Part 2.
|  | Jsc (mA/cm$^{-2}$) | Voc (V) | FF | PCE (%) |
|---|---|---|---|---|
| QH0306 | 11.85 | 0.83 | 0.47 | 4.64 |
| QH0311 | 16.33 | 0.79 | 0.50 | 6.44 |
| QH0315 | 12.59 | 0.82 | 0.45 | 4.69 |
| QH0318 | 7.90 | 0.81 | 0.37 | 2.40 |
| QH0333 | 14.84 | 0.78 | 0.47 | 5.37 |
Part 3. Polymers. Synthesis of which is described in FIG. 14
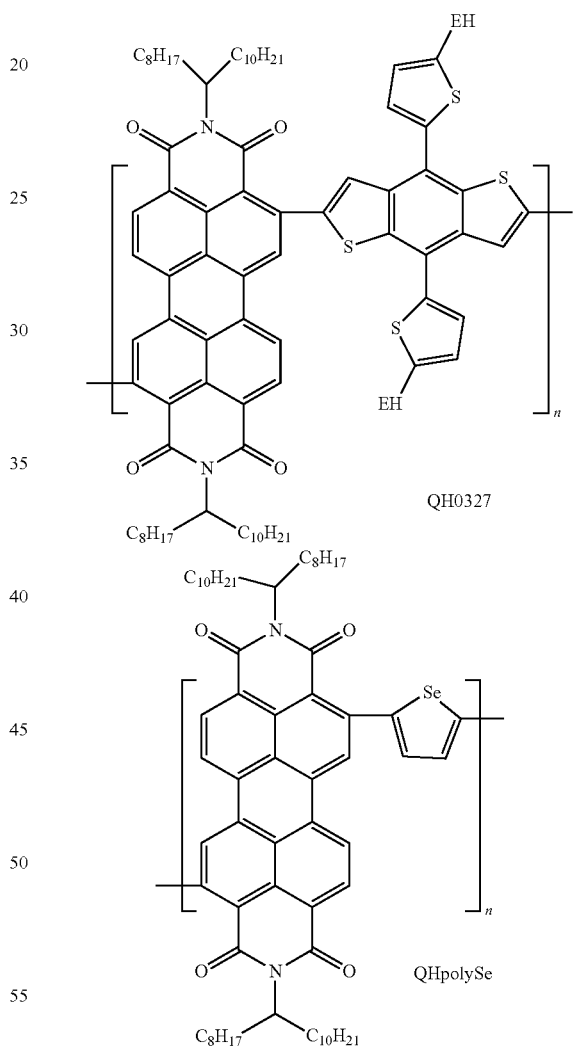
Properties of Polymers of Part 3.
|  | Jsc (mA/cm$^{-2}$) | Voc (V) | FF | PCE (%) |
|---|---|---|---|---|
| QH0327 | 5.57 | 0.65 | 0.34 | 1.23 |
| QHpolySe | 9.70 | 0.68 | 0.43 | 2.87 |

General Device Fabrication.

Zinc Oxide Sol-Gel stock solution was prepared by stirring 0.46 g $ZnAc_2 \cdot 2H_2O$ in 5 ml 2-methoxyethanol and 0.15 ml ethanol amine at 60° C. under ambient condition. Then the solution was cooled to room temperature and subsequently filtered from 0.45 μm PTFE film before use. The PTB7-Th and small molecule acceptors were co-dissolved in chlorobenzene and chloronaphthalene (95:5 vol/vol). The overall material concentration was 15 mg ml$^{-1}$ and the solution was stirred at 110° C. for 12 h under a $N_2$ atmosphere. ITO glass substrate (Thin Film Devices) was cleaned in water, acetone and isopropylalcohol for 15 min under sonication. Glasses were then exposed to ultraviolet ozone irradiation for 30 min. A thin layer (~40 nm) of ZnO sol-gel was spin-coated at 4,000 rpm for 40 sec onto ITO glasses and annealed at 200° C. in ambient condition for 30 min. After treated ZnO surface with 1% ethanolamine solution in methoxyethanol (3000 rpm for 40 s), the substrates were dried in 90° C. oven then transferred into glovebox immediately. Active layers were spin-coated using the as-prepared solutions at 1,000 rpm in a glove box. $MoO_3$ (7.5 nm) and Al (80 nm) anodes were thermal evaporated in a glove box at a chamber pressure of ~$2.0 \times 10^{-6}$ torr.

Device Fabrication.

The small molecule were co-dissolved with donor polymers, for example, PTB7-Th in chlorobenzene (CB) with or without 5% (v/v) chloronaphthalene (CN) in the weight ratio of 1:1.5. Donor polymer's concentrations are normally 6 mg/mL.

Indium Tin Oxide (ITO)-coated glass substrates (15 Ω/sq) were cleaned stepwise in detergent, water, acetone, and isopropyl alcohol under ultrasonication for 15 min each and subsequently UV-ozone plasma treated for 30 min. Then a thin layer of ZnO was spin-coated onto ITO surface at 4000 rpm. After being baked at 200° C. for 45 min under air. Then substrates were transferred to nitrogen filled glove box. The donor polymer/acceptor composites layer was then spin-cast from the CB solution to ZnO substrate at 800 to 4000 rpm to achieve optimum thickness. Then a MoO3 layer (5-10 nm) and an Al layer (80 nm) were deposited in sequence under the vacuum of $2 \times 10^6$ torr. The effective area of film was measured to be 0.0314 cm2. The current density-voltage (J-V curves were measured using a Keithley 2420 source-measure unit. The photocurrent was measured under AM 1.5 G illumination at 100 mW/cm2 under the Newport Oriel Sol3A Class AAA Solar Simulators 450 W solar simulator (Model: 94023A, 2 in.×2 in. beam size).

To further study properties of tetra-PDI acceptors, QH0311 was used as an acceptor third component in ternary blend organic solar cells. The light absorption in a range of 400-600 nm is complementing the light absorption of the donor material PTB7-Th and HOMO of all three components in the blend form a cascade, which, as previously reported, is beneficial for device performance. Indeed, when incorporated inside an active layer and after optimization we have achieved enhancement in the device performance reaching >10% PCE after optimization. The major enhancement was due to short circuit current density.

TABLE 3

Solar cell parameters for ternary OPV devices studied

| Active layer | $V_{oc}$, (V) | $J_{sc}$, (mA/cm$^2$) | FF, (%) | PCE, (%) | Highest PCE, (%) |
|---|---|---|---|---|---|
| PTB7-Th:PC$_71$BM (1:1.5) | 0.77 ± 0.01 | 18.1 ± 0.1 | 67.9 ± 0.7 | 9.5 ± 0.1 | 9.8 |
| PTB7-Th:TPBDT:PC$_71$BM (1:0.05:1.5) | 0.77 ± 0.01 | 18.7 ± 0.2 | 67.2 ± 0.2 | 9.8 ± 0.1 | 10.2 |
| PTB7-Th:TPBDT:PC$_71$BM (1:0.1:1.5) | 0.76 ± 0.01 | 19.4 ± 0.2 | 68.3 ± 0.8 | 10.1 ± 0.1 | 10.3 |
| PTB7-Th:TPBDT:PC$_71$BM (1:0.2:1.5) | 0.77 ± 0.01 | 19.6 ± 0.4 | 67.7 ± 0.2 | 10.1 ± 0.2 | 10.5 |

Synthesis of Fully Conjugated A-D-A Ladder Type Molecules and their Electronic Properties.

Figure 21:
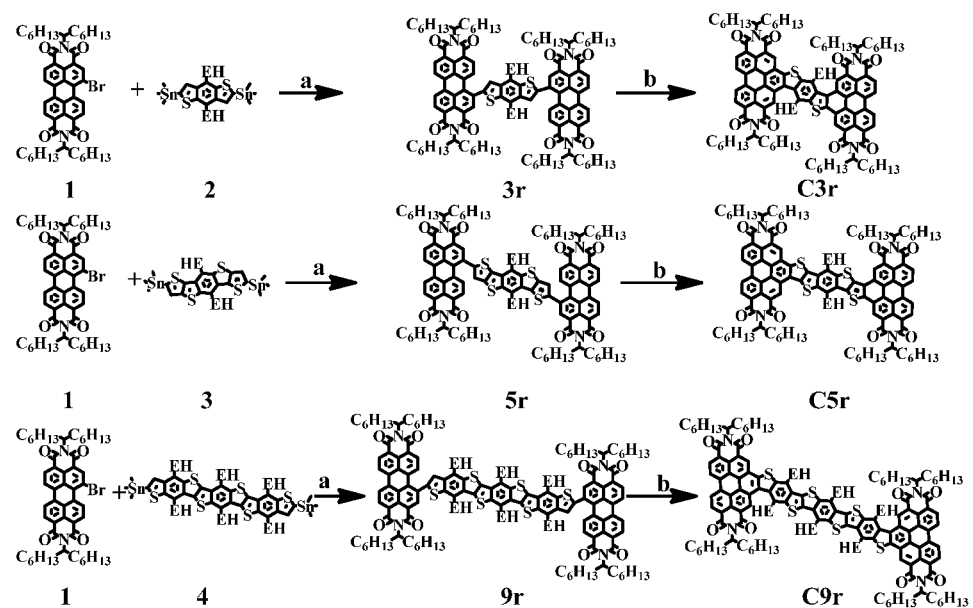
FIG. 21 depicts the synthesis Scheme 1. A-D-A molecules and their fused ring compounds.

Synthesis and structural characterization. See FIG. 21 for synthesis scheme. To stabilize the heteroacene compounds and extend the conjugation, a synthetic strategy as shown in scheme 1 was developed. Non-fused ring molecules (3r, 5r and 9r) were obtained by Pd-mediated coupling reaction between compound 1 and compounds 2-4. Although the thienyl or pheneyl substituted PDIs can be photochemical cyclized, the heteroacene-substituted PDI failed to underdo photocyclization reaction in the presence of 12, when the side chains on heteroacene donor system is alkyl group. However, the desired annulated compounds are obtained in high yields by following the Scholl cyclodehydrogenation using ferric chloride. Oxidative cyclodehydrogenation with ferric chloride is sometimes limited by the electronic character of the substituents. Typically, aromatic rings bearing electron withdrawing groups are less active in the cyclodehydrogenation reaction. Thus, the successful cyclodehydrogenation of fused-ring compounds with PDI to the desired product is a welcome exception. All the materials are soluble in common organic solvents such as $CH_2Cl_2$, $CHCl_3$, THF, and toluene. Thermogravimetric analysis (TGA) reveals that both non-fused ring and fused ring molecules are thermally stable up to 400° C.).

OPV Properties and Active Layer Characterization.

Photovoltaic effects are one of the most important excited state properties in organic molecules. It is strongly influenced by excited energy level, charge separation, and electron transfer processes. Herein, photovoltaic effects of all six novel compounds were evaluated via inverted thin film solar cell devices. The energy levels of the six compounds are suited as electron acceptor; all match well with that of PTB7-Th, an efficient donor polymers for bulk heterojunction organic solar cells 8.69 with enough energy offset for charge separation. Device structure is ITO/ZnO/Active Layer/MoO3/Ag. PTB7-Th was employed as donor polymer with donor/acceptor ratio of 1:2. Active layer thickness was controlled at about 80 nm. Preliminary device results are listed in Table 4 and their I-V curves were shown in FIG. 19. In general, all the fused ring materials exhibit better photovoltaic performance with higher Voc and FF compared to their non-fused counterparts.

Figure 22:
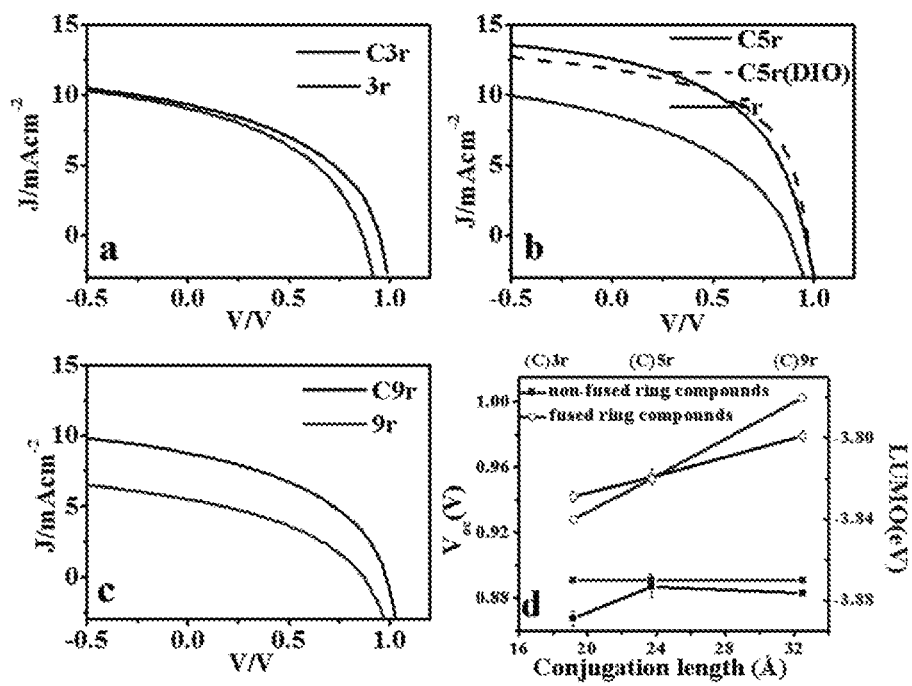
FIG. 22 depicts J-V curves of PTB7-Th/conjugated molecules devices.
Figure 23:
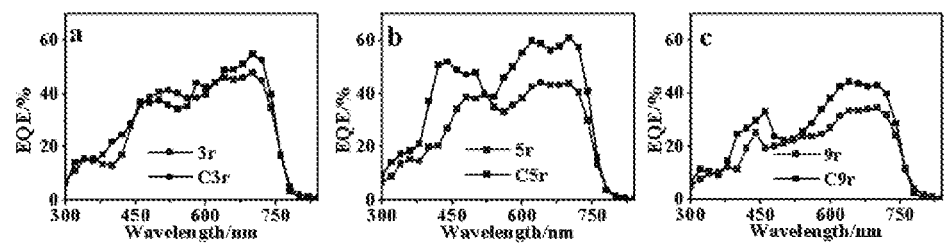
FIG. 23 depicts external quantum efficiency (EQE) spectra of PTB7 Th/conjugated molecules devices.
Figure 24:
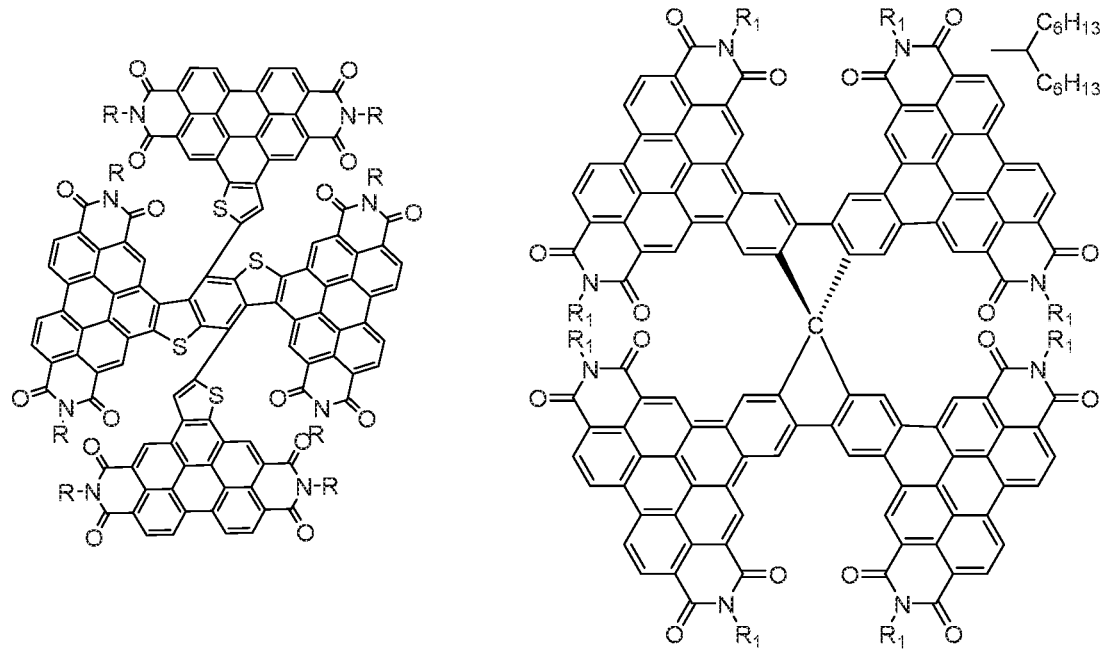
FIG. 24 depicts double bond linked tetra-PDIs.

It was found that fused ring acceptor materials exhibit enhanced Voc value. Cyclization of 3r to C3r increased Voc from 0.87 V to 0.94 V, 5r to C5r from 0.89 V to 0.95 V, 9r to C9r from 0.88 V to 0.98 V. This enhancement of Voc correlates with the band gap increase in the acceptor molecules (Table 1). The LUMO energy levels were dominated by PDI moiety and HOMO by BDT ladder unit for the non-fused ring compounds, so they show almost the same LUMO energy and similar Voc with the molecular length increase (FIG. 7d). For the fused ring molecules, the HOMO energy levels are reduced slightly due to electron withdrawing effect of the PDI and LUMO energy level increased due to electron donating effect of BDT moiety. Thus, both the energy levels and Voc of the fused ring compounds increase linearly with the length of the molecular structures (FIG. 22d).

A dilemma of material design in BHJ solar cells is that, to achieve high Voc with a certain donor polymer, acceptor with higher LUMO would be desirable for high Voc value, however at the same time, higher LUMO of acceptor also implies smaller difference between LUMO of donor and LUMO of acceptor, which will reduce driving force for charge separation, and is detrimental to Jsc value. The system described here shows that devices benefits from obvious Voc enhancement without sacrificing their Jsc. The C3r show almost same Jsc with 3r, and C5r and C9r even have much higher Jsc than that of 5r and 9r. C9r device has Jsc of 8.9 mA/cm2 which is 35% higher than Jsc of 9r device (5.4 mA/cm2). The C5r device showed Jsc of 12.5 mA/cm2, which is 50% enhancement compared to 8.4 mA/cm2 of 5r device. Overall, all fused ring acceptors show higher photo conversion efficiency over their non-fused ring counterparts. Without any processing additive, highest efficiency 5.6% was achieved by C5r device which has outstanding Jsc and FF compared to others. PCE as high as 6.1% was achieved by introducing 0.5% DIO as processing additive of C5r device, implying C5r has great potential as efficient electron acceptor after more careful optimization.

TABLE 4

Solar cell efficiencies of PTB7-Th/conjugated molecules[a].

| | $J_{sc}$/ mA/cm² | $V_{oc}$/ V | FF (%) | PCE (%) | $\mu_h$ (cm²/Vs) | $\mu_e$ (cm²/Vs) |
|---|---|---|---|---|---|---|
| 3r | 8.96 | 0.87 | 0.42 | 3.26 ± 0.02 | 4.43 × 10⁻⁴ | 5.00 × 10⁻⁵ |
| C3r | 9.31 | 0.94 | 0.43 | 3.75 ± 0.07 | 3.08 × 10⁻⁴ | 1.43 × 10⁻⁵ |
| 5r | 8.39 | 0.89 | 0.40 | 2.97 ± 0.03 | 2.67 × 10⁻⁴ | 3.46 × 10⁻⁵ |
| C5r | 12.50 | 0.95 | 0.47 | 5.59 ± 0.10 (6.06)[b] | 3.55 × 10⁻⁴ | 6.21 × 10⁻⁵ |
| 9r | 5.38 | 0.88 | 0.39 | 1.85 ± 0.12 | 2.91 × 10⁻⁴ | 2.03 × 10⁻⁵ |
| C9r | 8.89 | 0.98 | 0.43 | 3.69 ± 0.01 | 2.16 × 10⁻⁴ | 1.22 × 10⁻⁵ |

[a]Results are averaged over 10 devices,
[b]With 0.5% DIO as an additive

Figure 20:
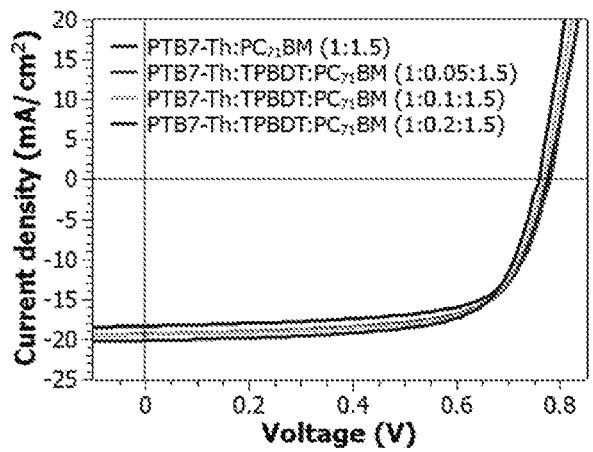
FIG. 20 depicts the JV curves of ternary OPV devices using QH0311.
Figure 20:
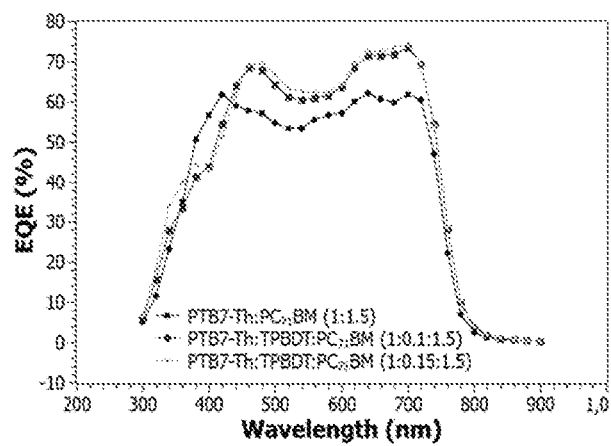

To understand the reason of $J_{sc}$ enhancement, we measured external quantum efficiencies (EQE) of the devices (FIG. 20). The C3r and 3r devices show overall similar EQE spectrum and almost identical $J_{sc}$ value. For 5r and C5r, C5r shows much higher quantum efficiency, with PTB7-Th reaching 60% at 600-800 nm. The high quantum efficiency of 50% between 400-500 nm corresponds to the strong absorption peak of C5r, indicating an efficient hole transfer from acceptor to donor. For 9r and C9r, although both acceptor materials show high absorbance between 400 to 500 nm, their quantum efficiency are lower than 40%, meaning they are inefficient in generating charge carriers.

Charge carrier mobility is evaluated by SCLC method. Hole-only devices are fabricated with the structure of ITO/PEDOT/Active layer/MoO₃/Ag, and electron-only devices are fabricated with the structure of ITO/ZnO/Active layer/Ca/Al. Hole mobilities of blend devices are similar and are of magnitude of $10^{-4}$ cm²V⁻¹ s⁻¹. Electron mobility differs greatly between different acceptors. The best performing device, C5r, show highest electron mobility of 6.21×10⁻⁵ cm²V⁻¹s⁻¹. With hole mobility of 3.55×10⁻⁴ cm²V⁻¹s⁻¹, the hole to electron mobility ratio of C5r blend device is only 5.7. This fairly balanced mobility helps to explain the best $J_{sc}$ and FF value of C5r device among the six acceptors. This high electron mobility of C5r blend is clearly due to the highly planarity of the molecular structure of C5r.

PROPHETIC EXAMPLES

The present disclosure contemplates the following additional molecular acceptors synthesized by the general reaction schemes shown below.

Pd₂(dba)₃ (25 mg) and P(MeOPh)₃ (75 mg) is added to a mixture of starting materials, THF (12 mL) and 2M K₂CO₃ aqueous solution (3 mL) under nitrogen. After refluxing overnight, the mixture is poured into methanol. The precipitate will be filtered and purified by column chromatography, using dichloromethane/hexane=1:1 as the eluent.

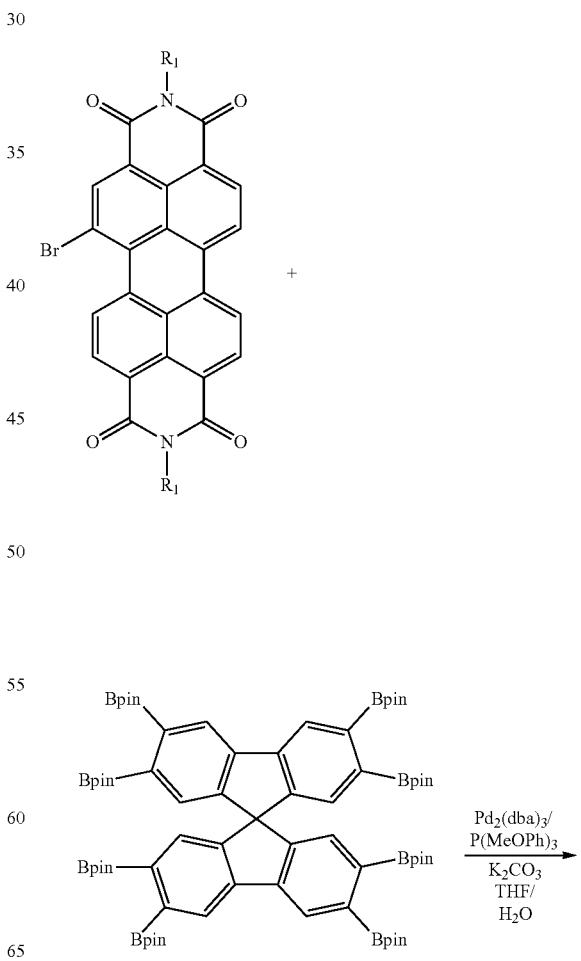

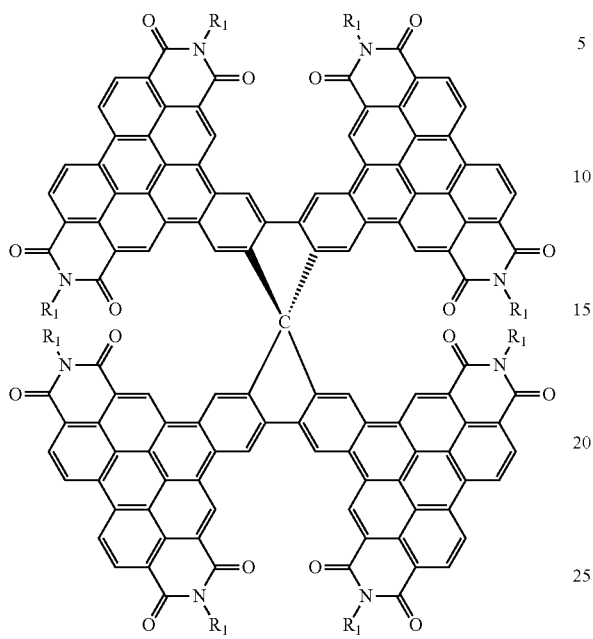
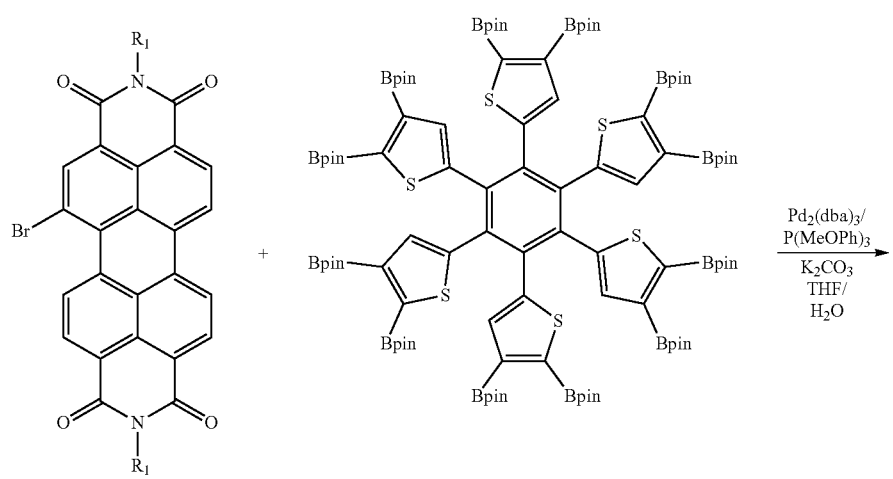

-continued

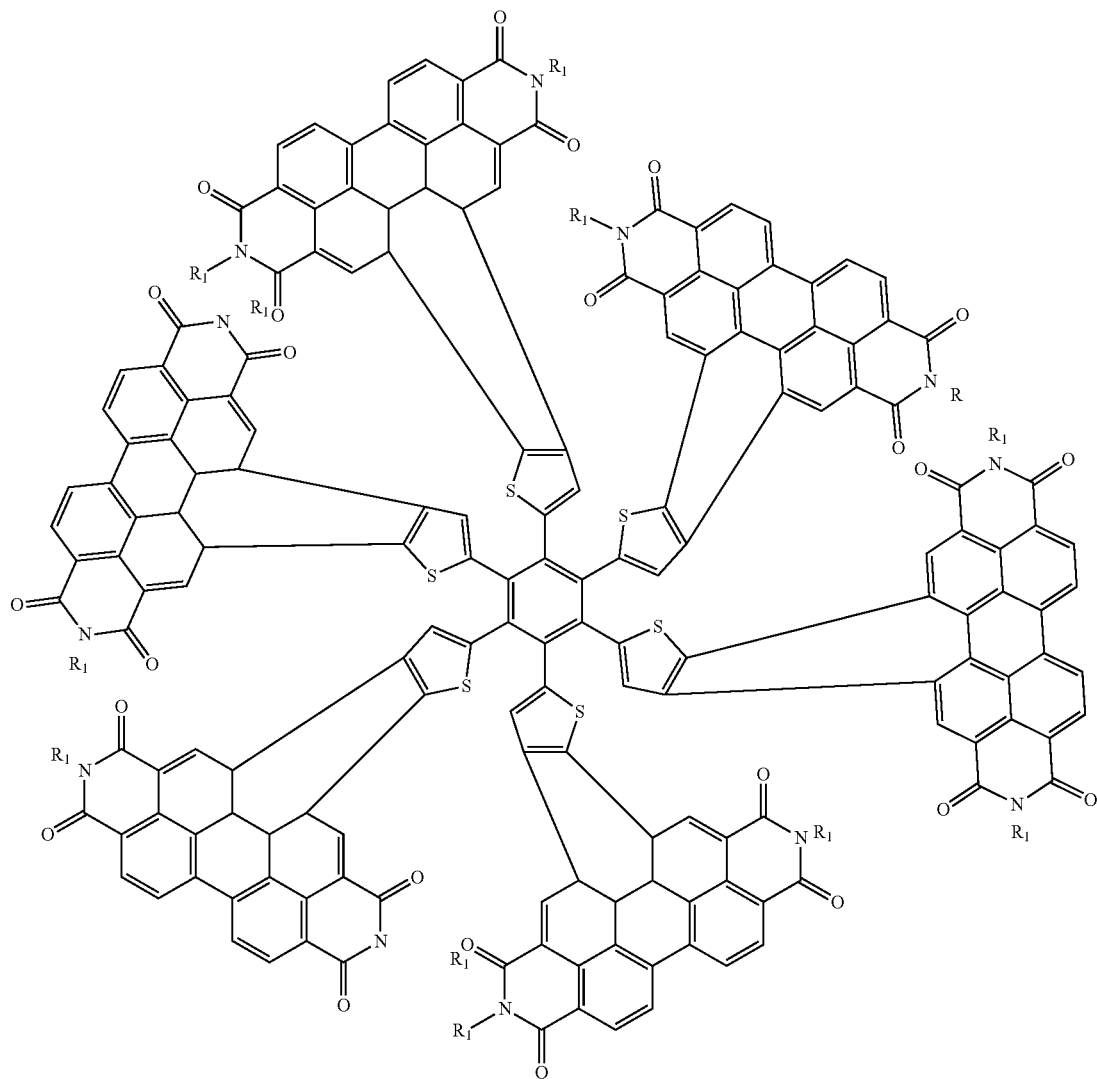

Although specific embodiments of the present disclosure are herein illustrated and described in detail, the disclosure is not limited thereto. The above detailed descriptions are provided as exemplary of the present disclosure and should not be construed as constituting any limitation of the disclosure. Modifications will be obvious to those skilled in the art, and all modifications that do not depart from the spirit of the disclosure are intended to be included with the scope of the appended claims.

What is claimed is:

1. A molecular acceptor of formula A:

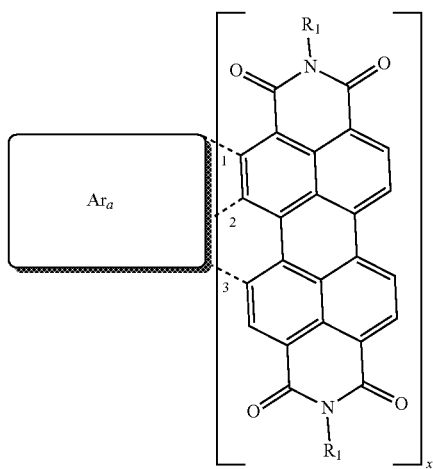

where $R^1$ is selected from: $C_1$-$C_{30}$ linear or branched chain alkyl;

x is an integer selected from: 2, 4 and 6; wherein when $Ar_a$ is bonded at 1, and x is 2, $Ar_a$ is selected from: a bond,

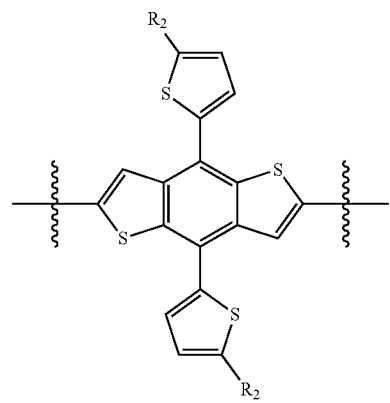

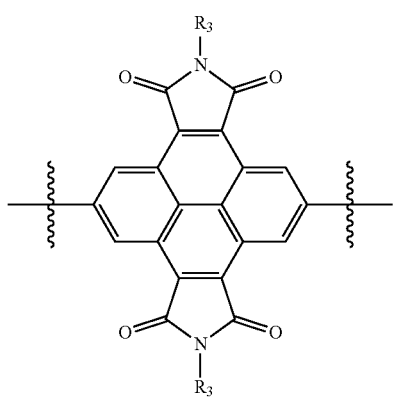

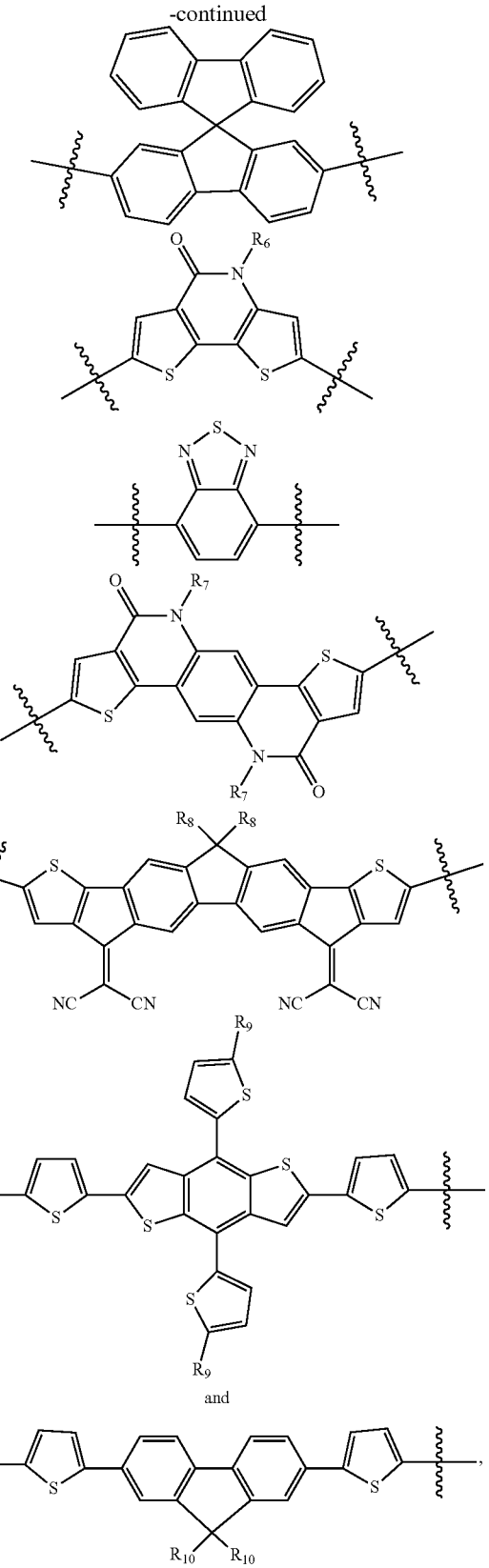

wherein $R^2$, $R^3$, $R^4$, $R^5$, $R^6$, $R^7$, $R^8$, $R^9$, and $R^{10}$, if present, are each independently selected from: $C_1$-$C_{30}$ linear or branched chain alkyl, and

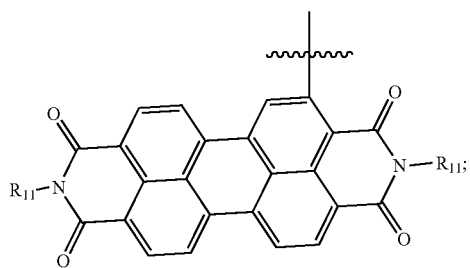
wherein R[11], if present, is $C_1$-$C_{30}$ linear or branched chain alkyl;
or when $Ar_a$ is bonded at 1, and x is 4, $Ar_a$ is selected from:
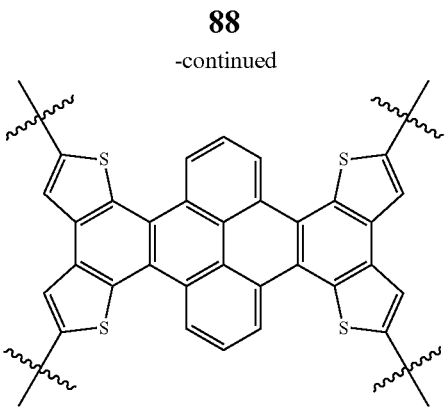
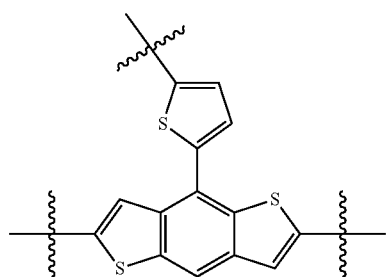
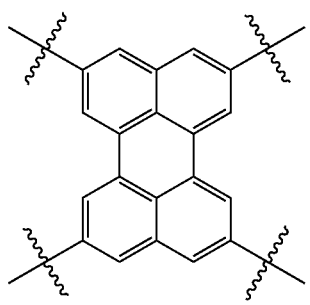
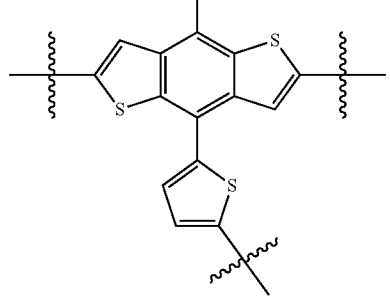
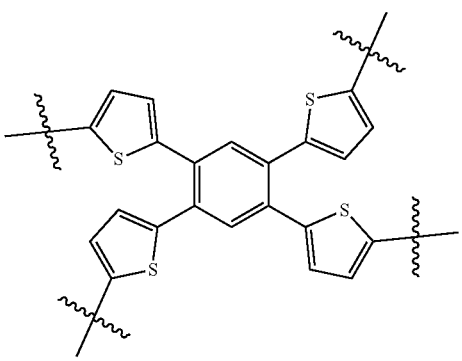
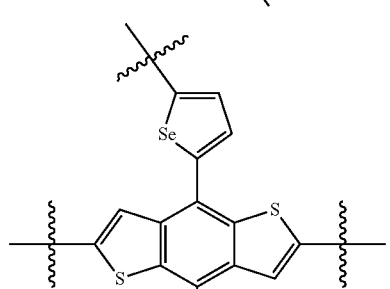
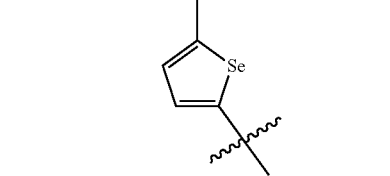
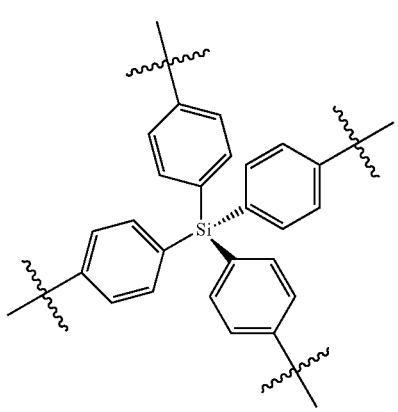
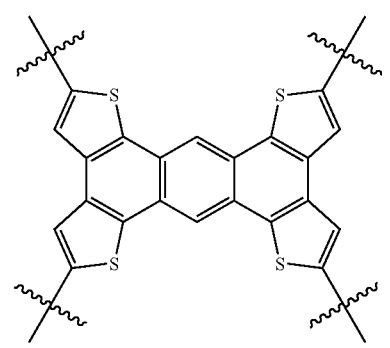

-continued
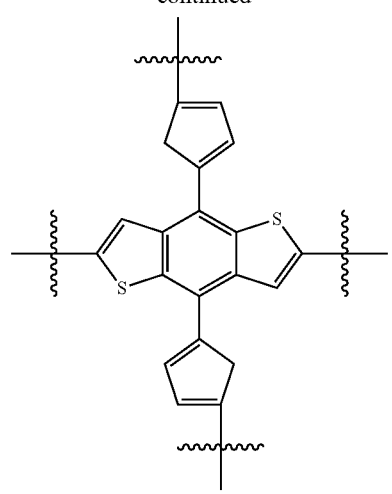
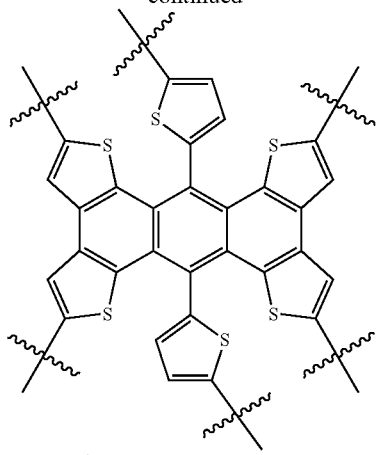
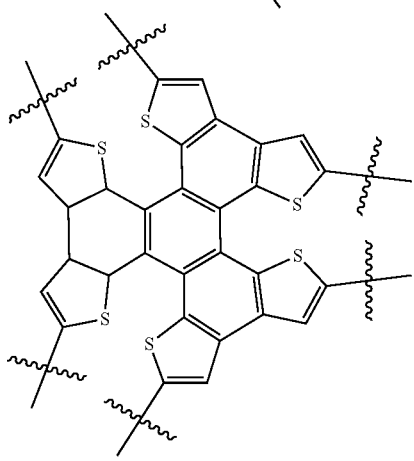
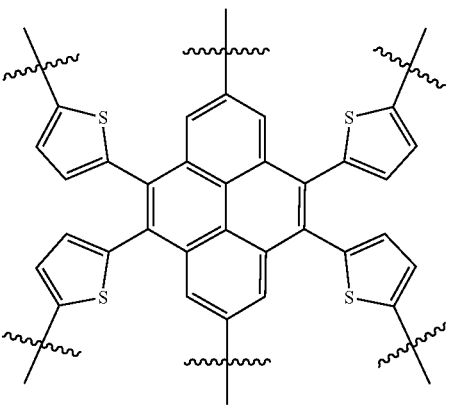
or when Ar$_a$ is bonded at 1, and x is 6, Ar$_a$ is selected from:
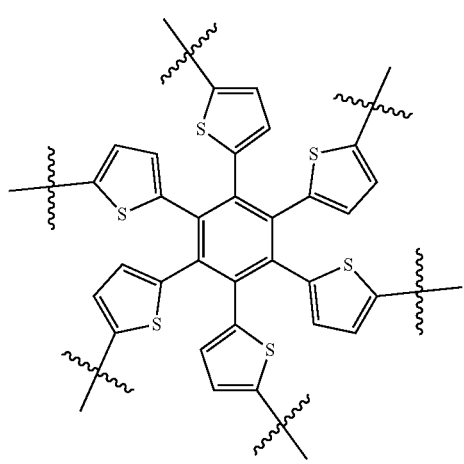
or when Ar$_a$ is bonded at 2 and 3 and x is 2, Ar$_a$ is selected from:
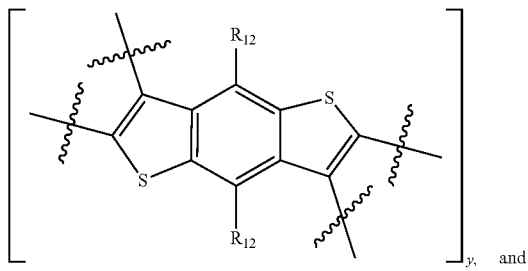
and -continued

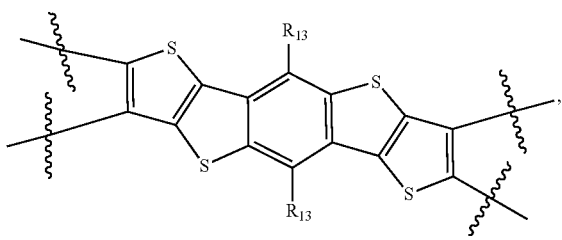

wherein $R^{12}$ and $R^{13}$, if present, are selected from: $C_1$-$C_{30}$ linear or branched chain alkyl; and wherein y is an integer selected from 1 and 3;

or when $Ar_a$ is bonded at 2 and 3 and x is 4, $Ar_a$ is selected from:

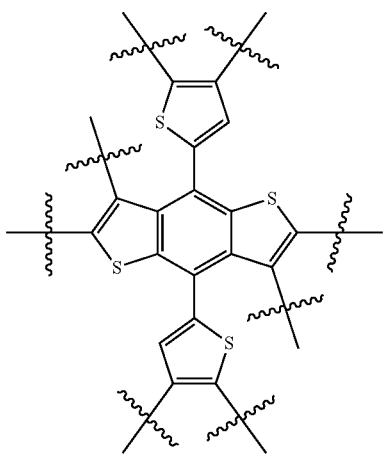

and

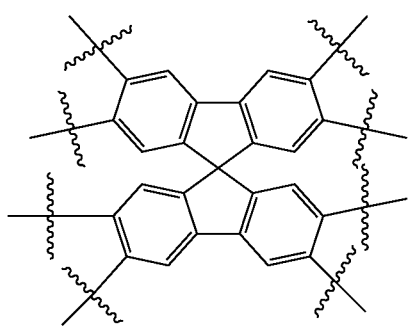

or when $Ar_a$ is bonded at 2 and 3 and x is 6, $Ar_a$ is:

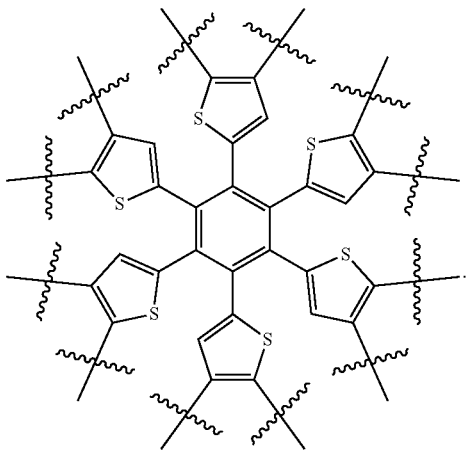 [SMILES: *c1cc(-c2c(-c3cc(*)c(*)s3)c(-c3cc(*)c(*)s3)c(-c3cc(*)c(*)s3)c(-c3cc(*)c(*)s3)c2-c2cc(*)c(*)s2)sc1*]

2. A molecular acceptor of formula I:

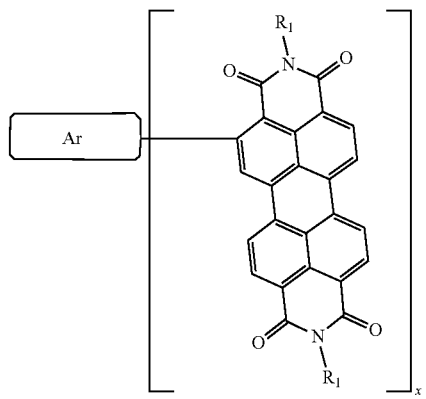

where $R^1$ is selected from: $C_1$-$C_{30}$ linear or branched chain alkyl;

x is an integer selected from: 2, 4 and 6;

wherein when x is 2, Ar is selected from: a bond,

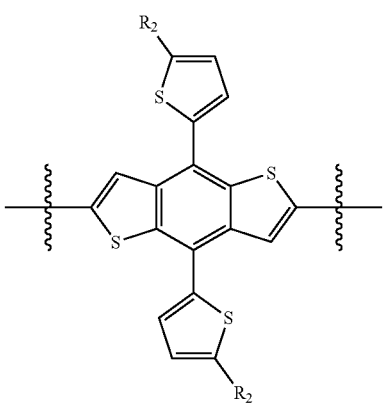

-continued
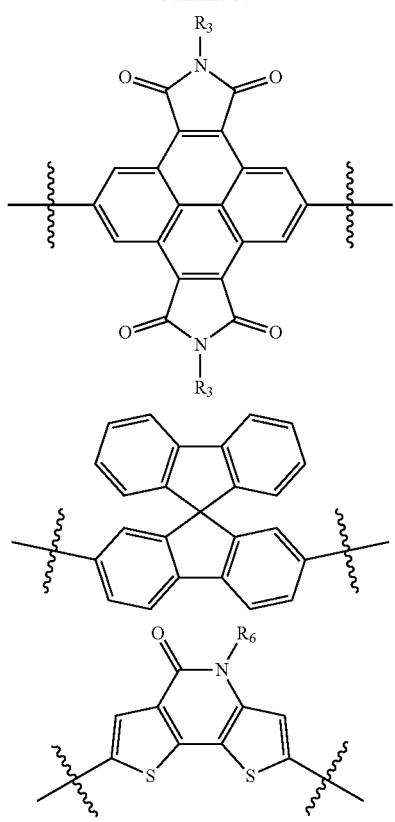
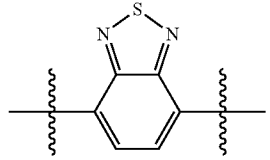
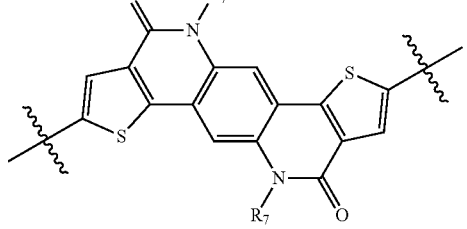
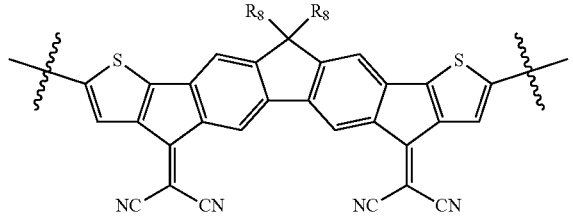
-continued
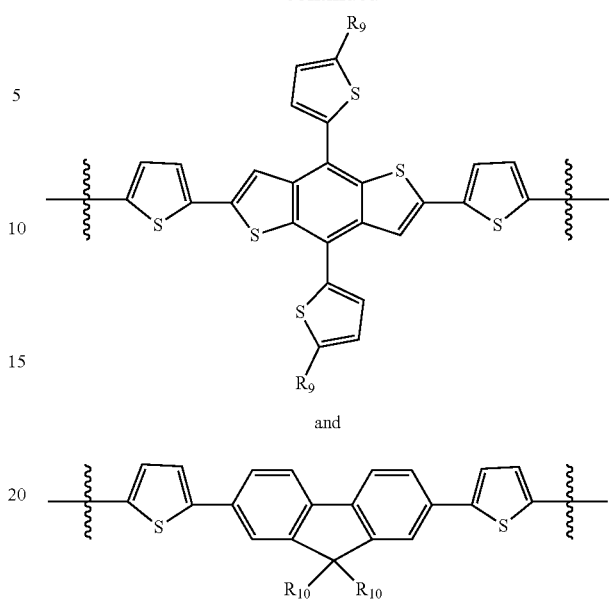
and
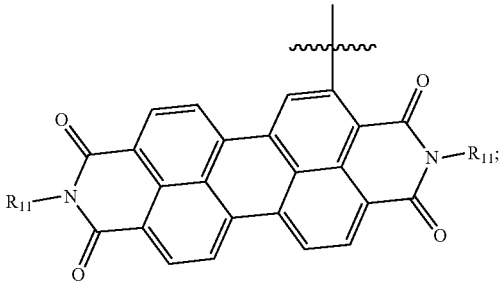
$R^2$, $R^3$, $R^4$, $R^5$, $R^6$, $R^7$, $R^8$, $R^9$ and $R^{10}$, if present, are each independently selected from:
$C_1$-$C_{30}$ linear or branched chain alkyl, and
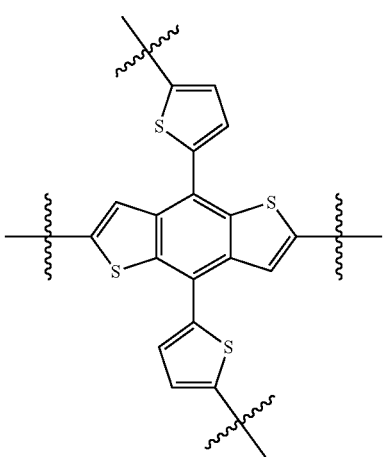
$R^{11}$, if present, is $C_1$-$C_{30}$ linear or branched chain alkyl; or when x is 4, Ar is selected from:

95
-continued
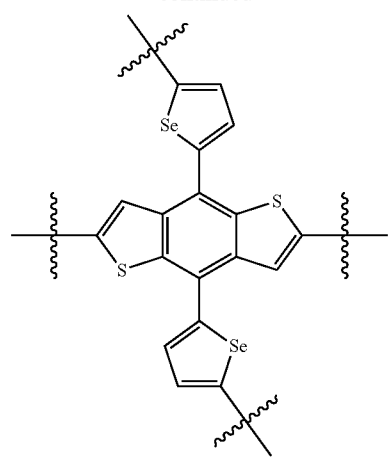
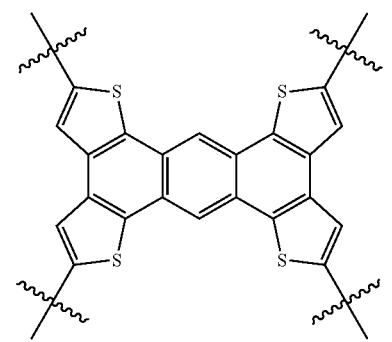
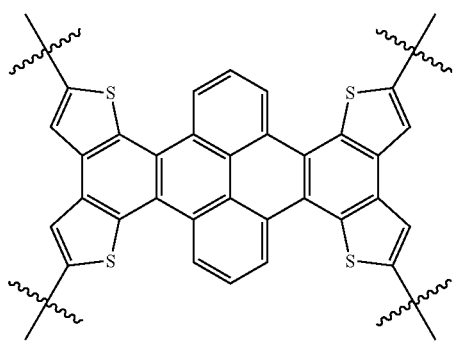
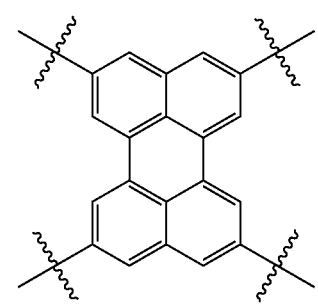
96
-continued
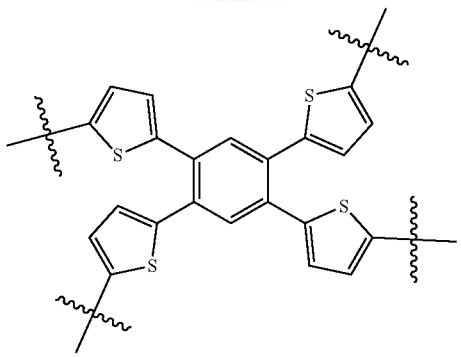
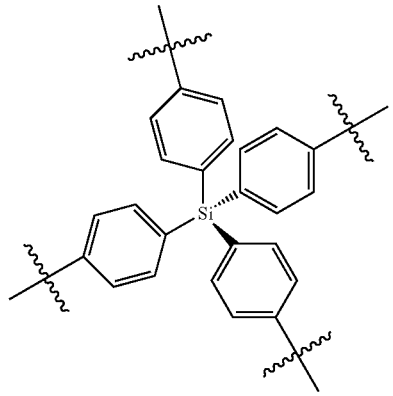
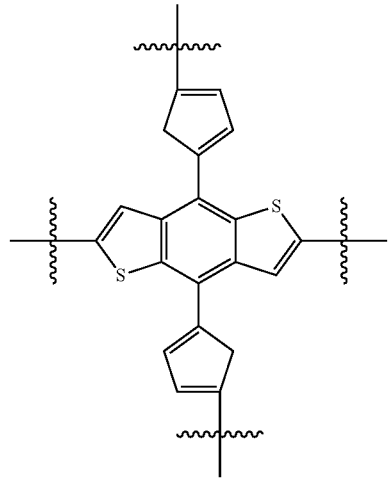
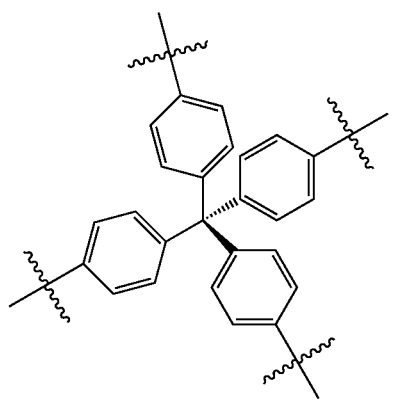

or when x is 6, Ar is selected from:
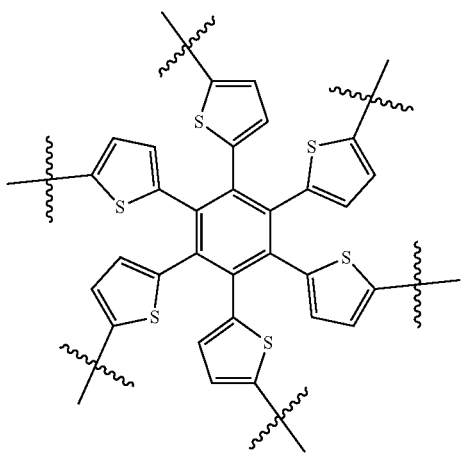
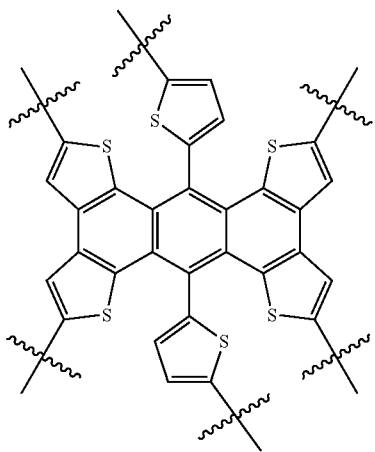
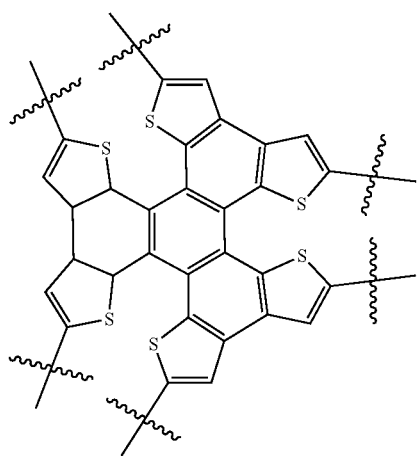
-continued
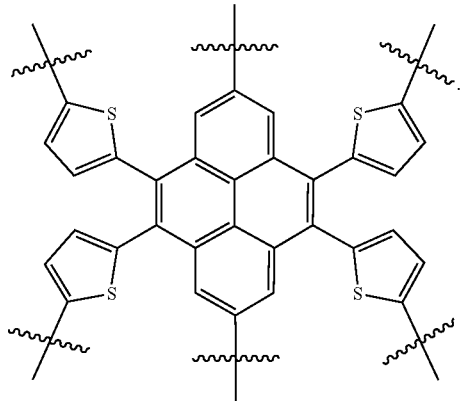
3. The molecular acceptor of claim 2 further selected from an acceptor of formula II:
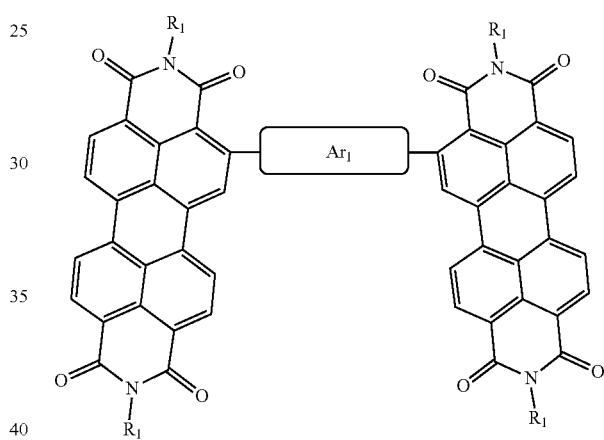
where $R_1$ is a selected from: $C_1$-$C_{30}$ linear or branched chain alkyl; and
$Ar_1$ is selected from: a bond,
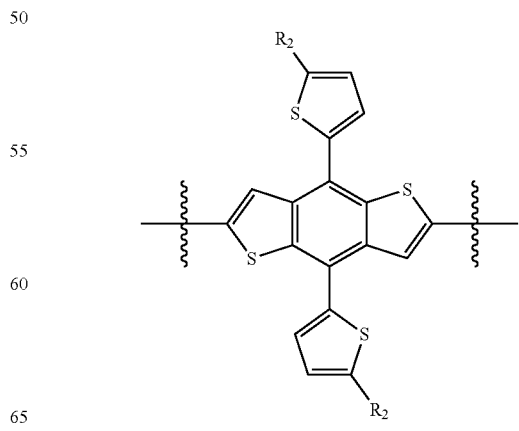

-continued
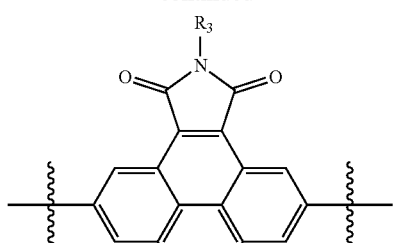
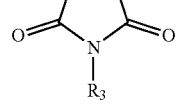
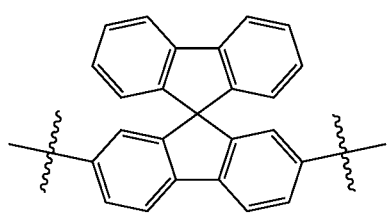
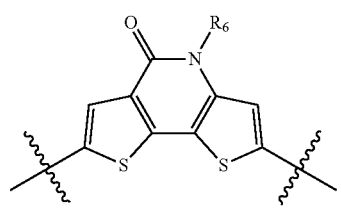
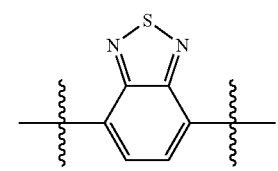
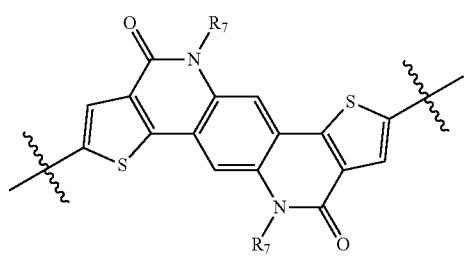
-continued
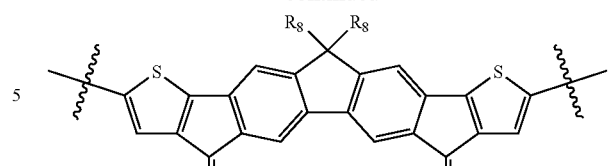
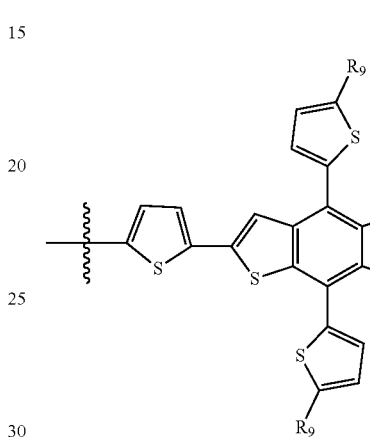
and
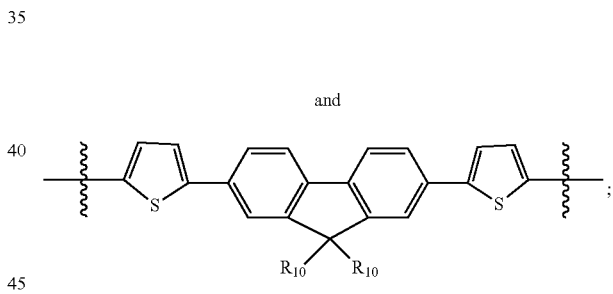
$R^2$, $R^3$, $R^4$, $R^5$, $R^6$, $R^7$, $R^8$, $R^9$ and $R^{10}$, if present, are each independently selected from a: $C_1$-$C_{30}$ linear or branched chain alkyl, and
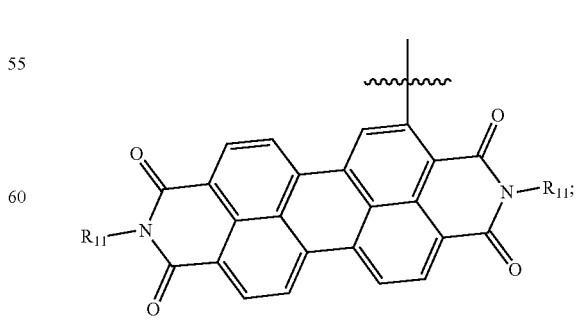
$R^{11}$, if present, is $C_1$-$C_{30}$ linear or branched chain alkyl.

4. The molecular acceptor of claim 3 further selected from:
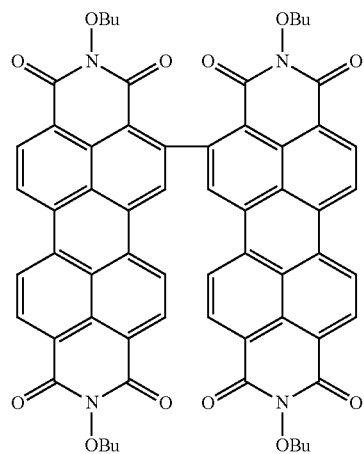
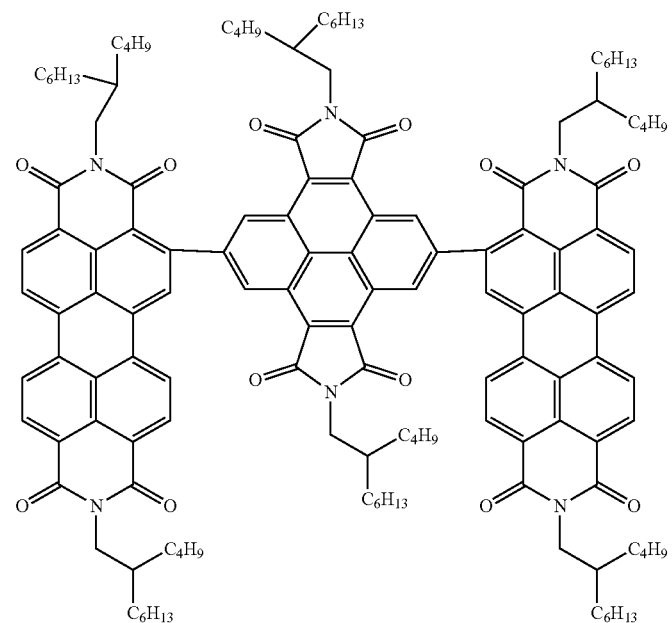
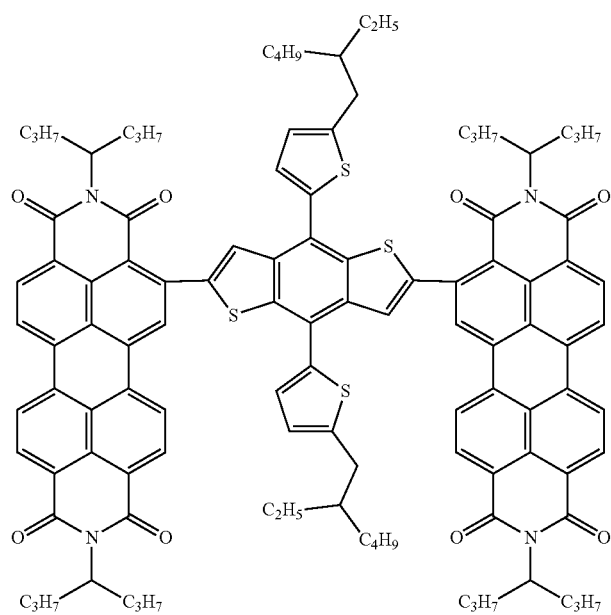
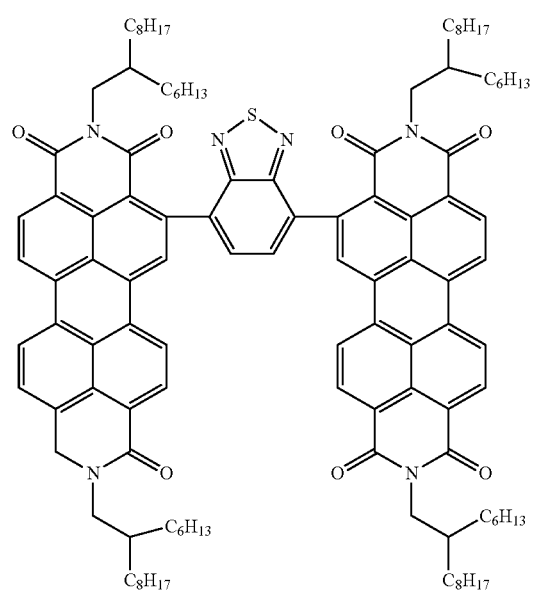

-continued
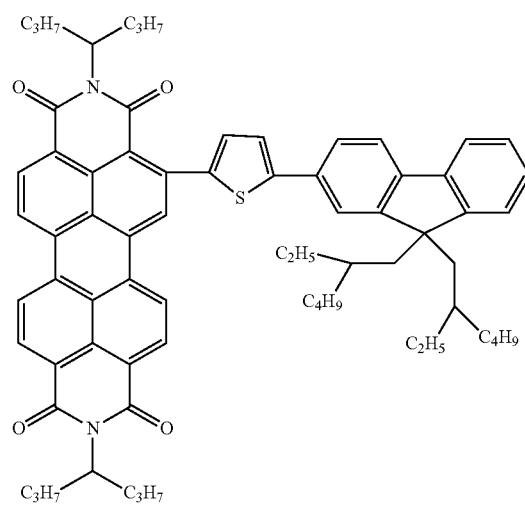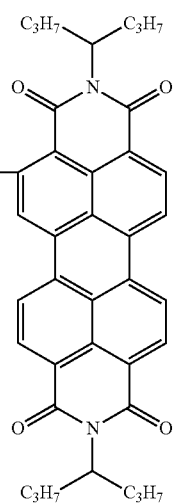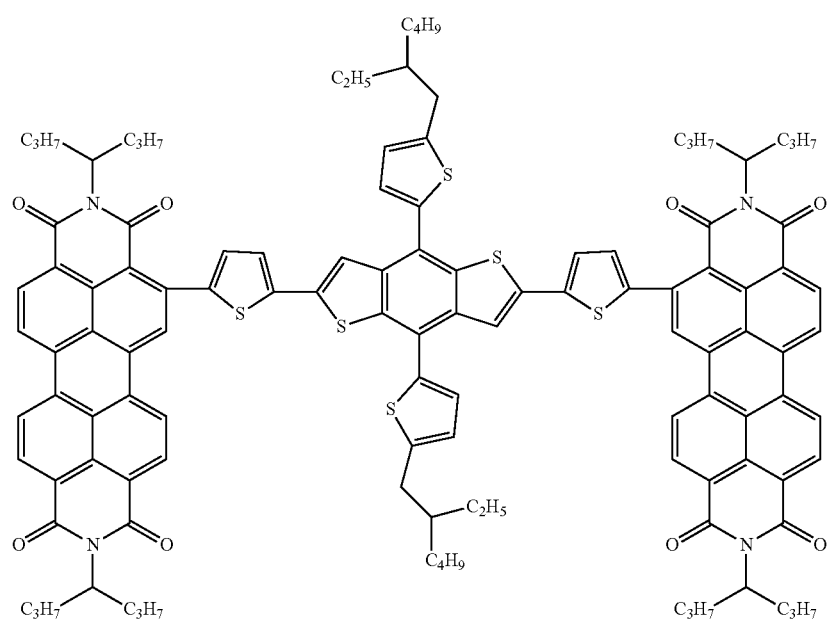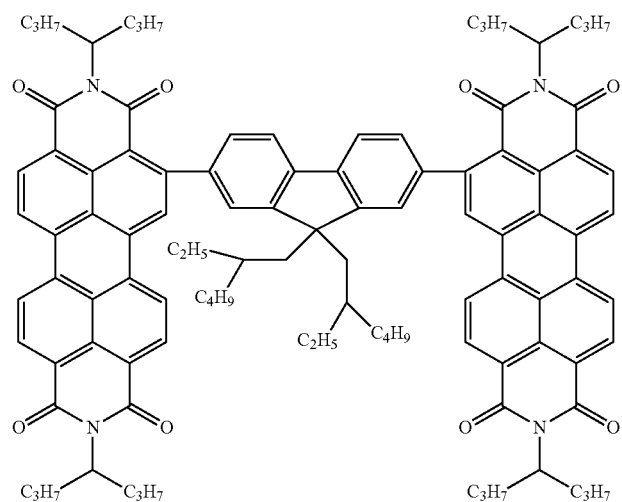

-continued
105
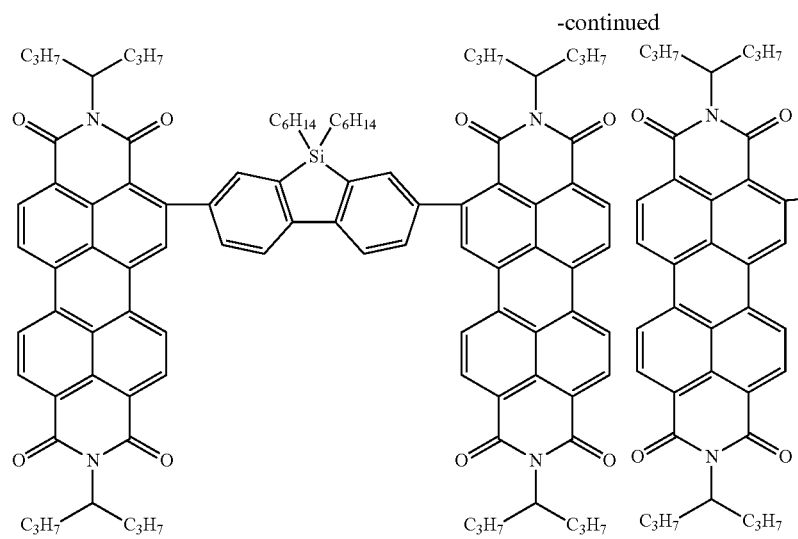
106
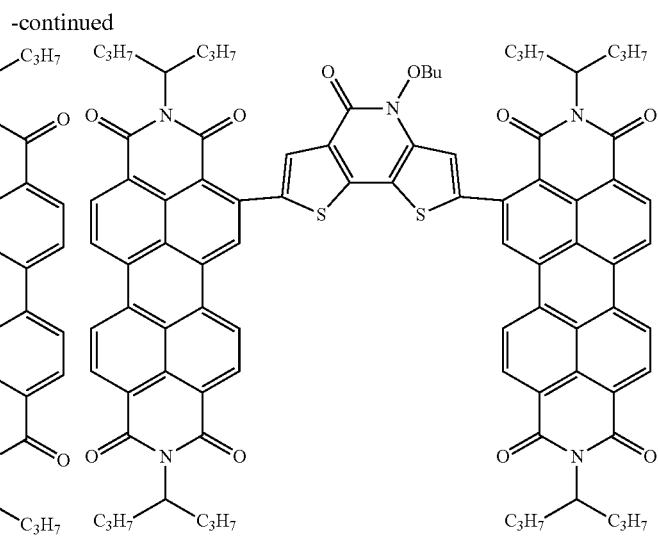
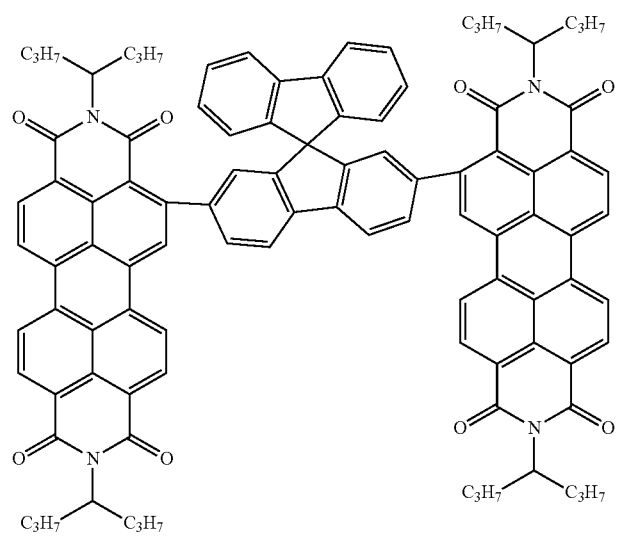

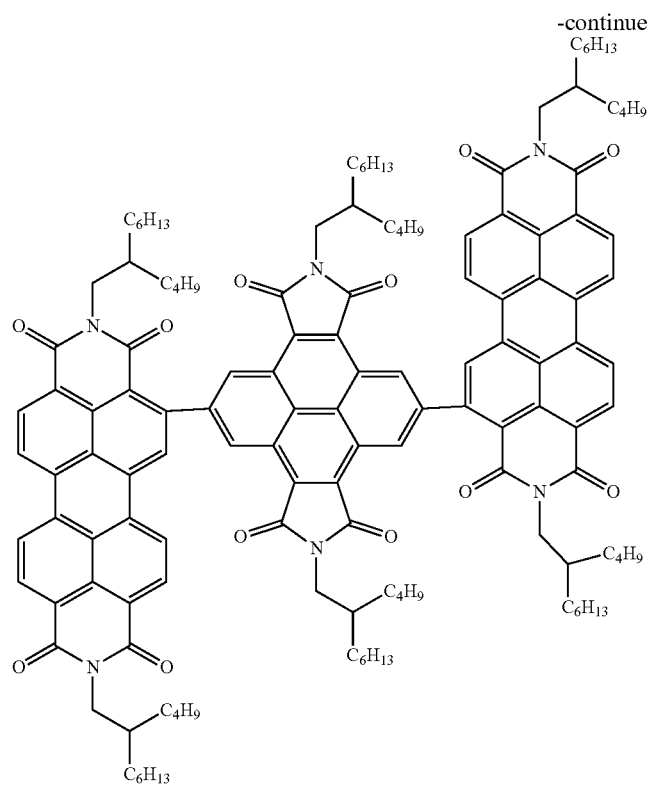
-continued
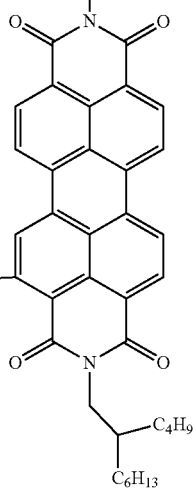
and
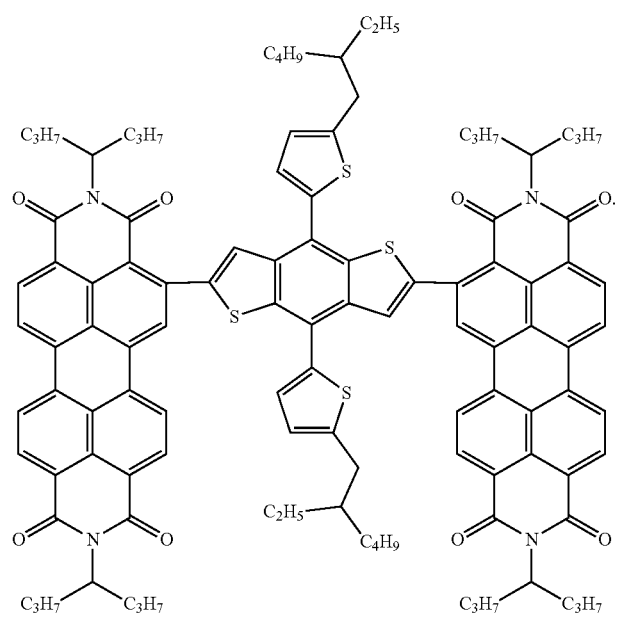

5. The molecular acceptor of claim 4 having a power conversion efficiency of greater than 4.92%.

6. The molecular acceptor of claim 1 further selected from an acceptor of formula VI:

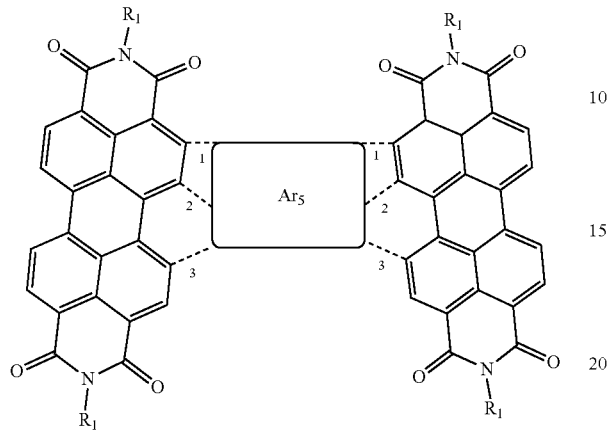

where $R^1$ is a selected from: $C_1$-$C_{30}$ linear or branched chain alkyl; and when $Ar_5$ is bonded at 1, $Ar_5$ is selected from: a bond

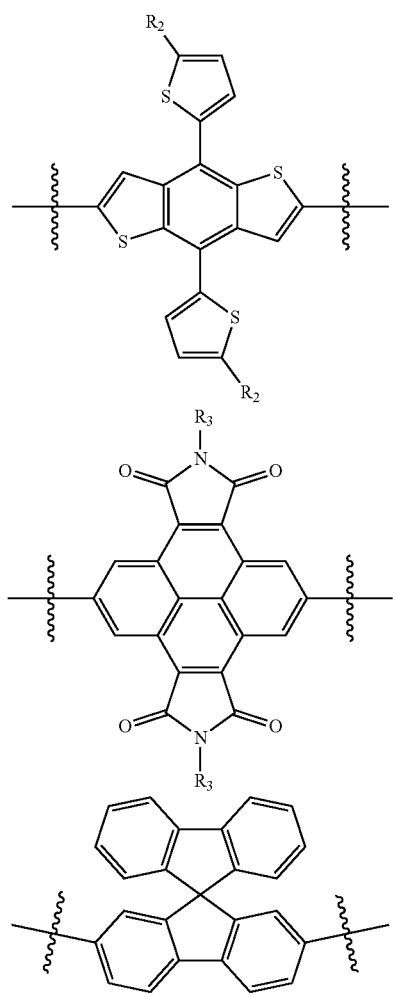

-continued wherein $R^2$, $R^3$, $R^4$, $R^5$, $R^6$, $R^7$, $R^8$, $R^9$ and $R^{10}$, if present, are each independently selected from: $C_1$-$C_{30}$ linear or branched chain alkyl, and

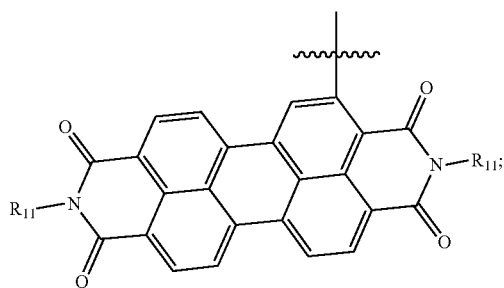

wherein $R^{11}$, if present, is $C_1$-$C_{30}$ linear or branched chain alkyl;

or wherein when $Ar_5$ is bonded at 2 and 3, where $Ar_5$ is selected from:

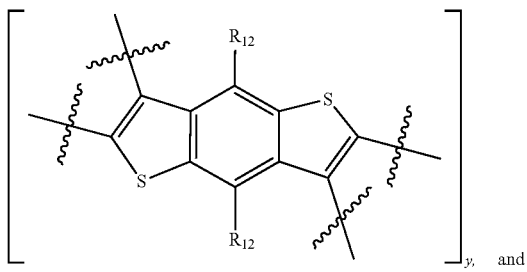

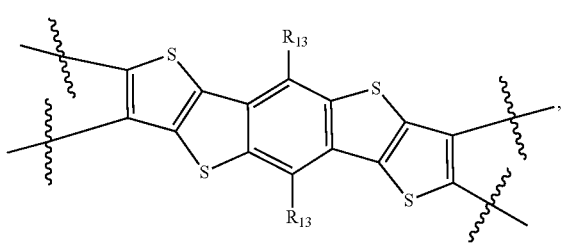

wherein $R^{12}$ and $R^{13}$, if present, are selected from: $C_1$-$C_{30}$ linear or branched chain alkyl; and wherein y is an integer selected from 1 and 3.

7. The molecular acceptor of claim 6 further selected from an acceptor of formula VII:

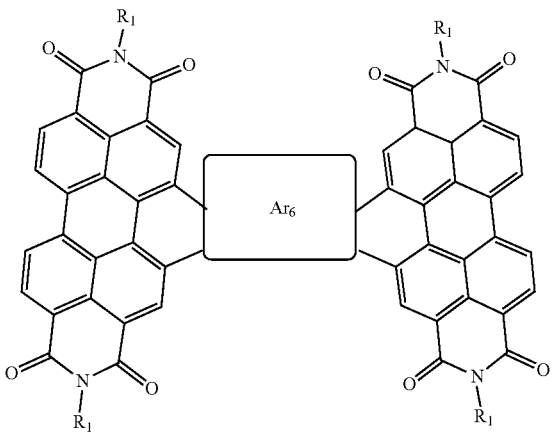

where $R_1$ is a selected from: $C_1$-$C_{30}$ linear or branched chain alkyl; and wherein $Ar_6$ is selected from:

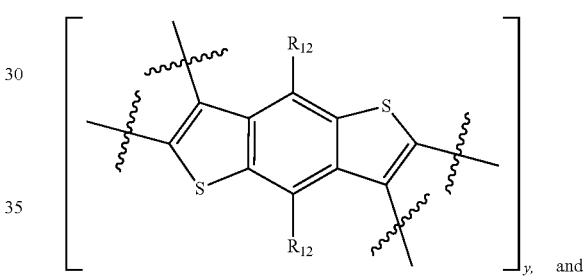

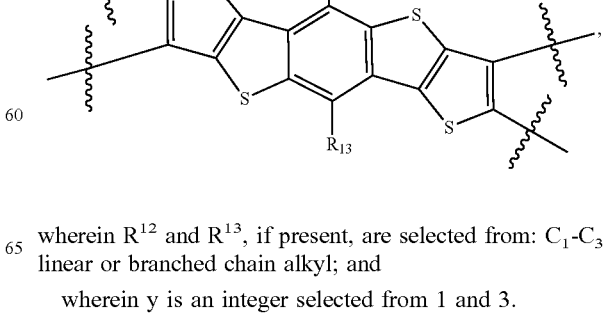

wherein $R^{12}$ and $R^{13}$, if present, are selected from: $C_1$-$C_{30}$ linear or branched chain alkyl; and wherein y is an integer selected from 1 and 3.

8. The molecular acceptor of claim 7 further selected from:
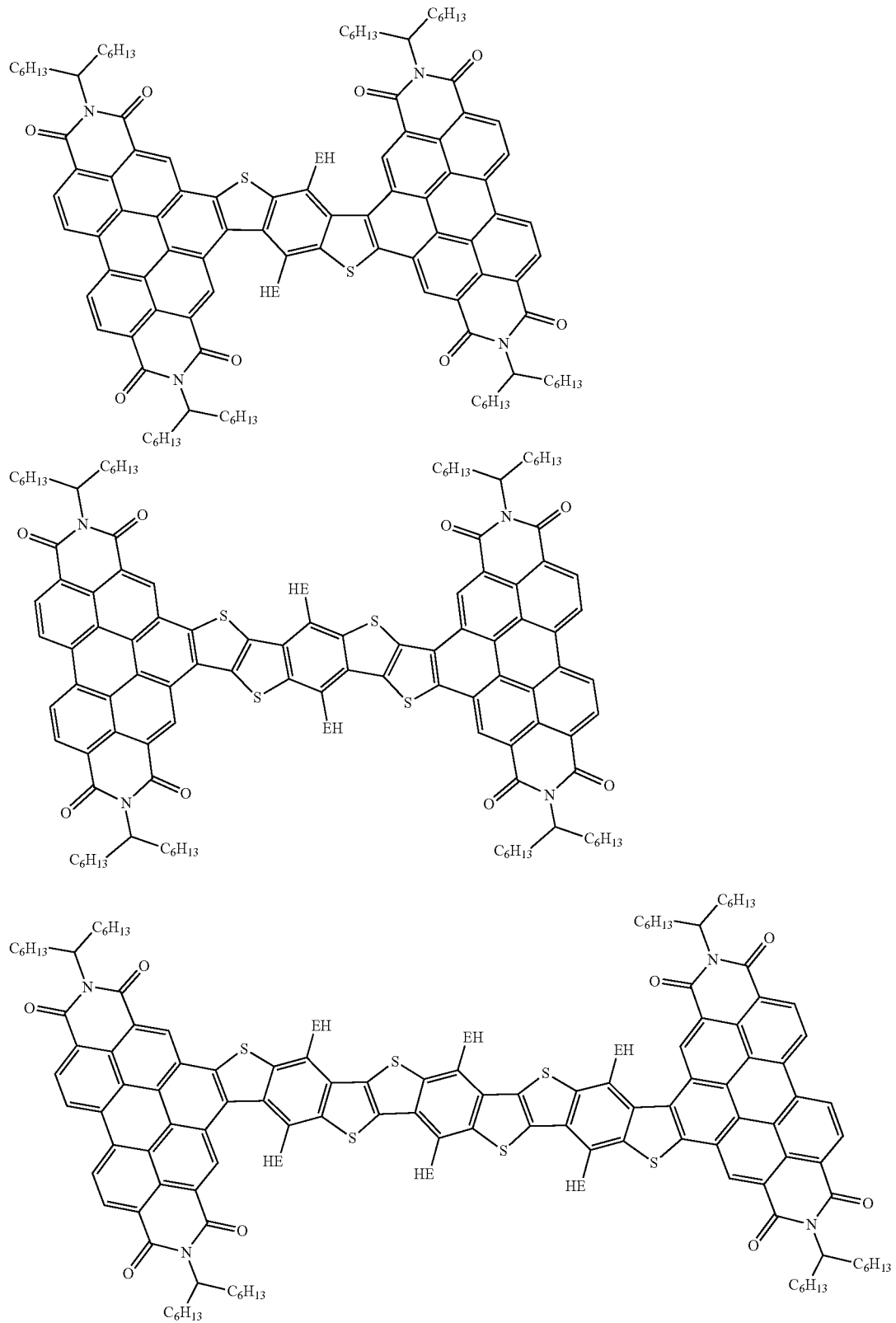
wherein EH is 2-ethyl hexyl.

9. The molecular acceptor of claim 8 having a power conversion efficiency of greater than 5.59%.
10. A molecular acceptor of claim 1, further selected from an acceptor of formula IX:
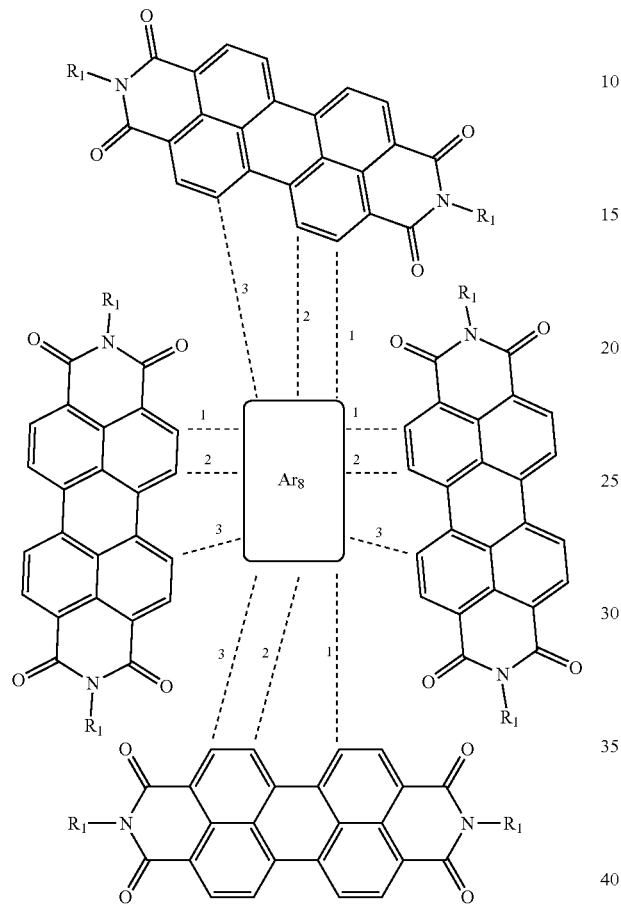
where $R^1$ is $C_1$-$C_{30}$ linear or branched chain alkyl; and
wherein when $Ar_8$ is bonded at 1, $Ar_8$ is selected from
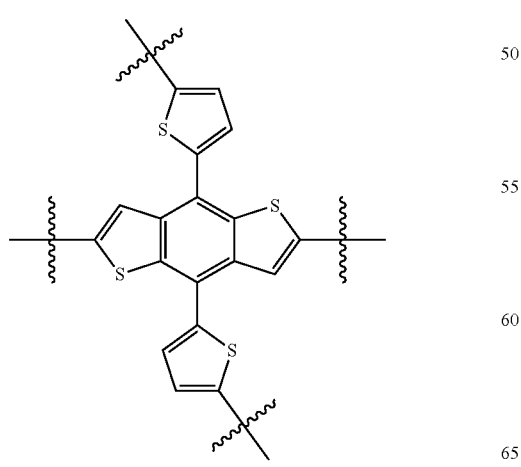
-continued
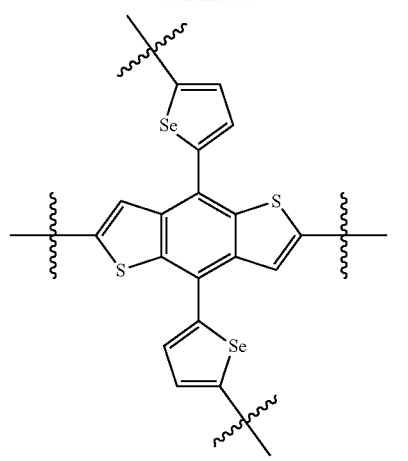
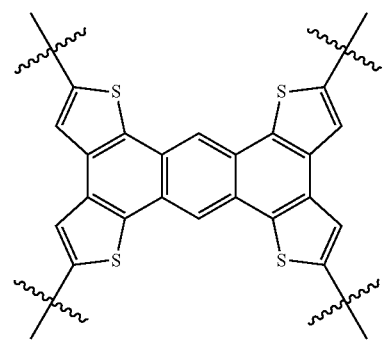
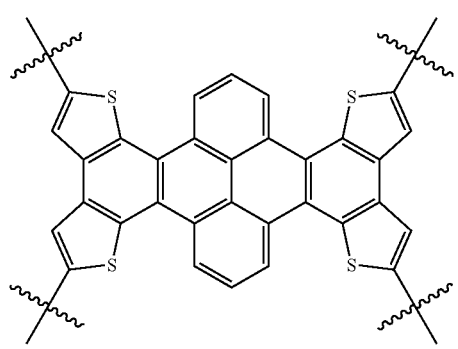
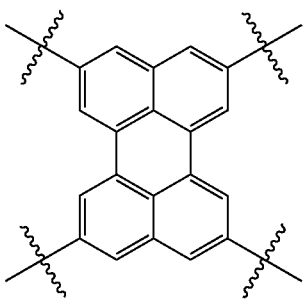

117
-continued
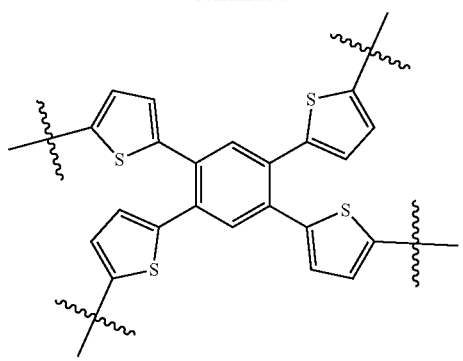
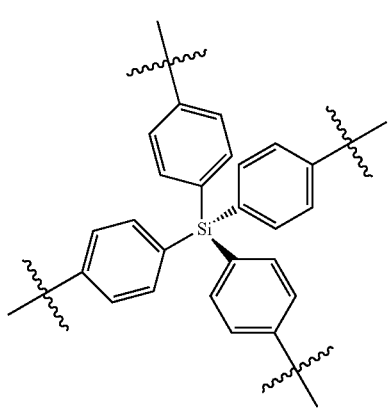
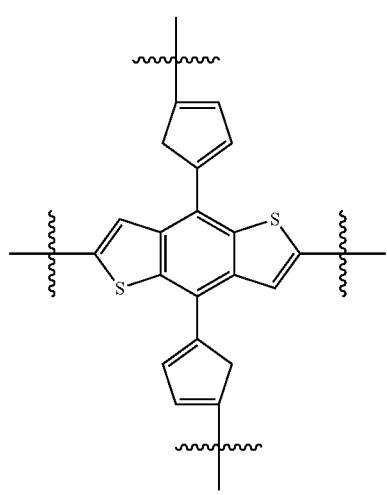
118
-continued
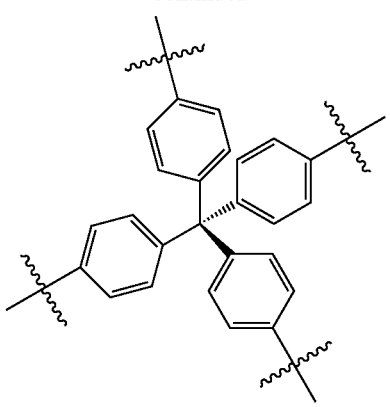
or when Ar$_8$ is bonded at 2 and 3, Ar$_8$ is selected from:
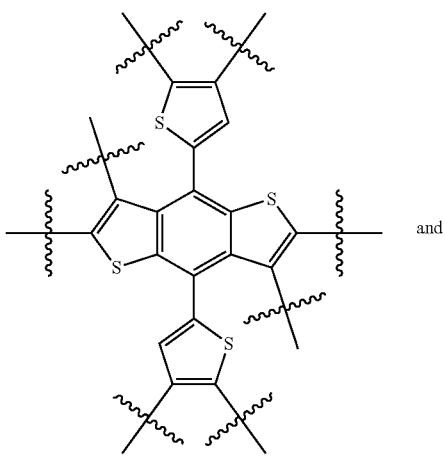 and
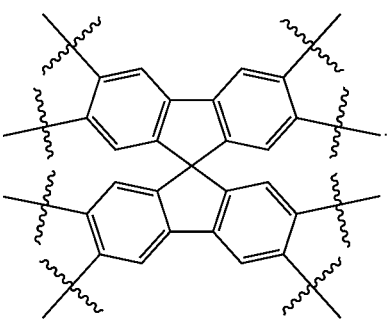

11. A molecular acceptor of claim 10 further selected from an acceptor of formula III:
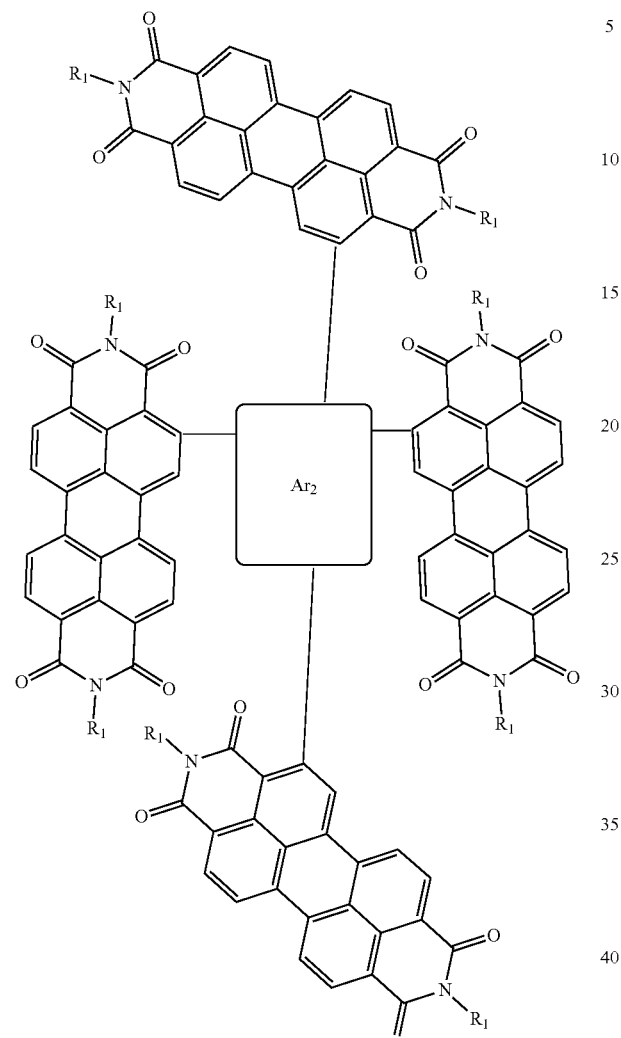
where R¹ is $C_1$-$C_{30}$ linear or branched chain alkyl; and Ar₂ is selected from the group consisting of:
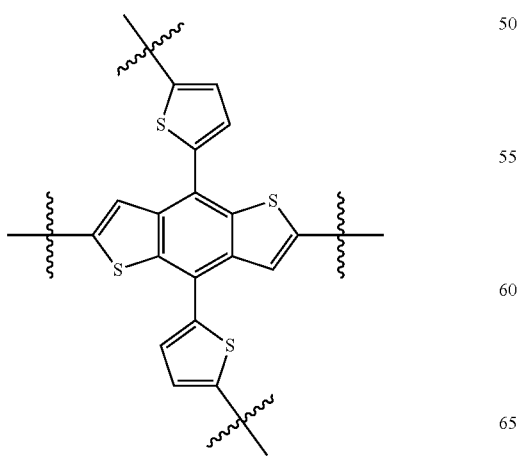
-continued
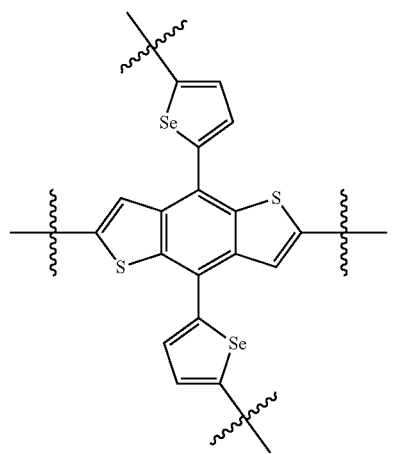
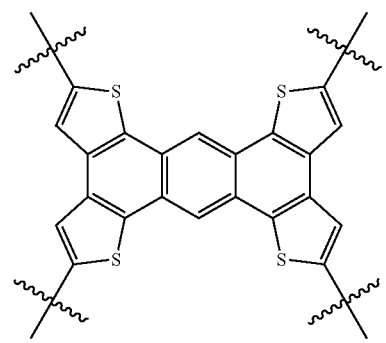
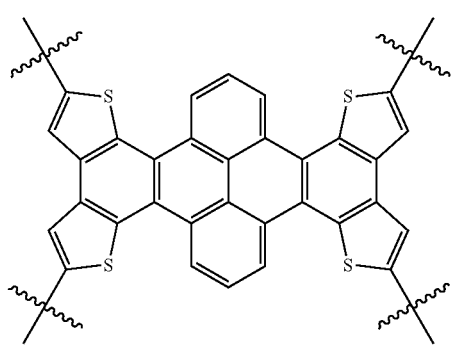
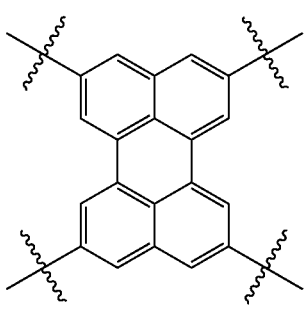

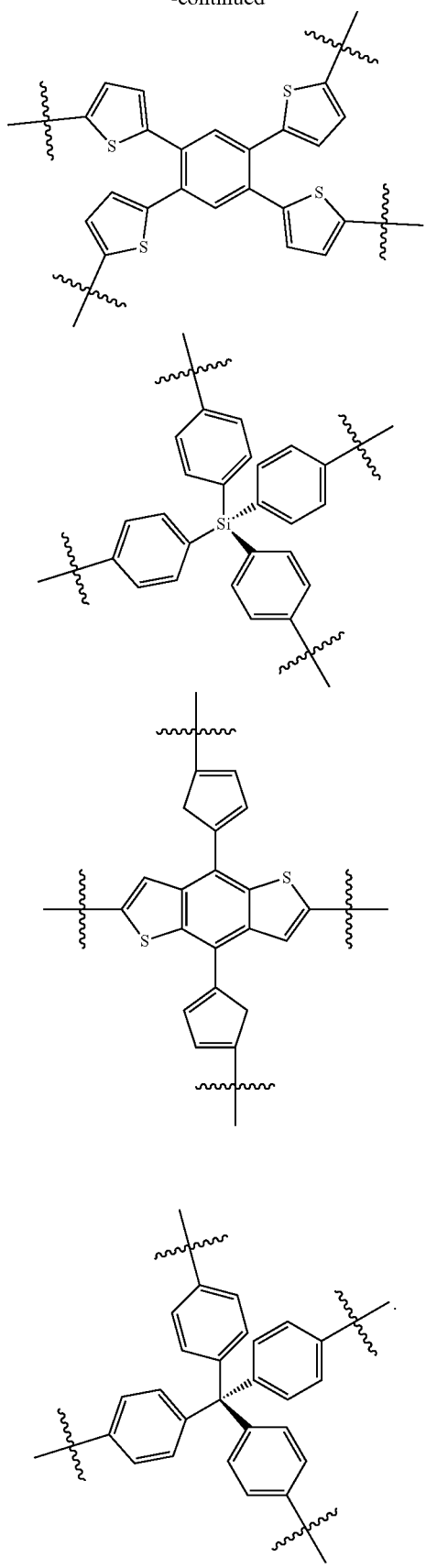
12. The molecular acceptor of claim 11 selected from:
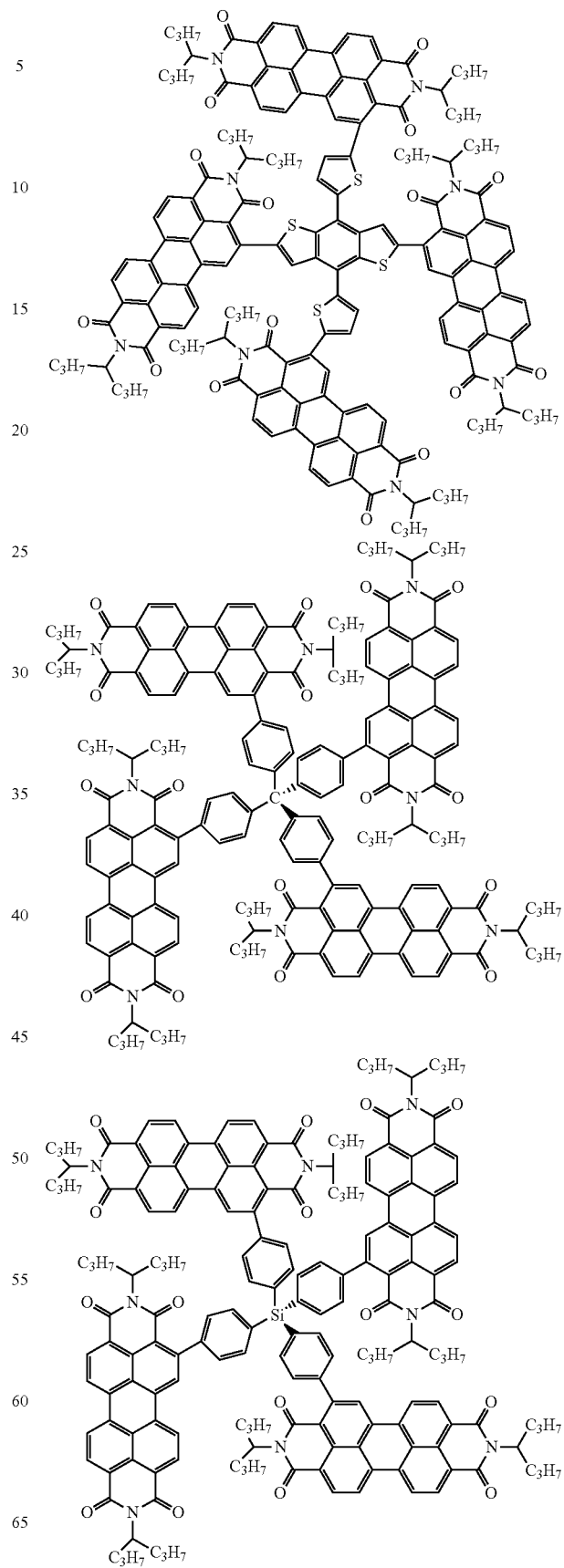

-continued
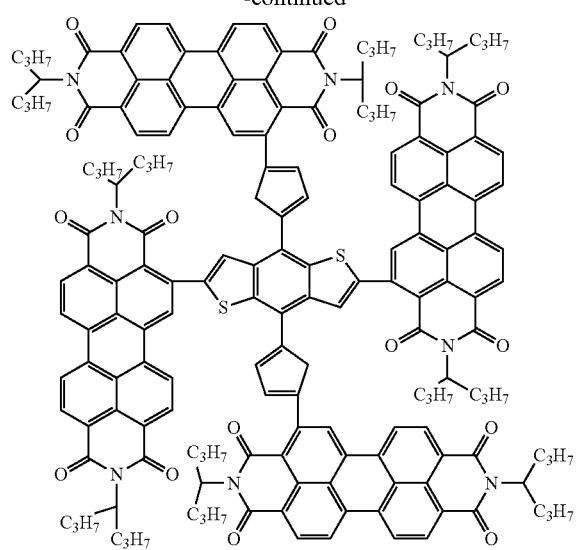
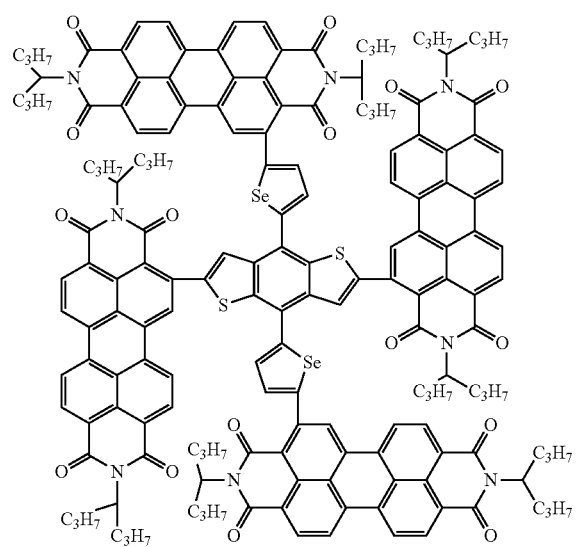
13. A molecular acceptor of claim 10 further selected from an acceptor of formula X:
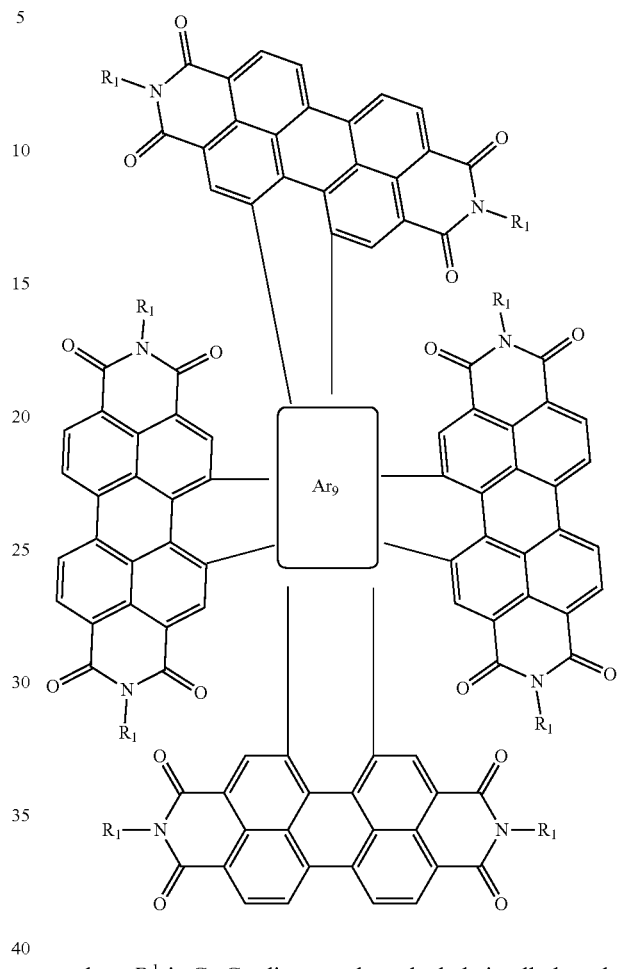
where $R^1$ is $C_1$-$C_{30}$ linear or branched chain alkyl; and
wherein $Ar_9$ is selected from:
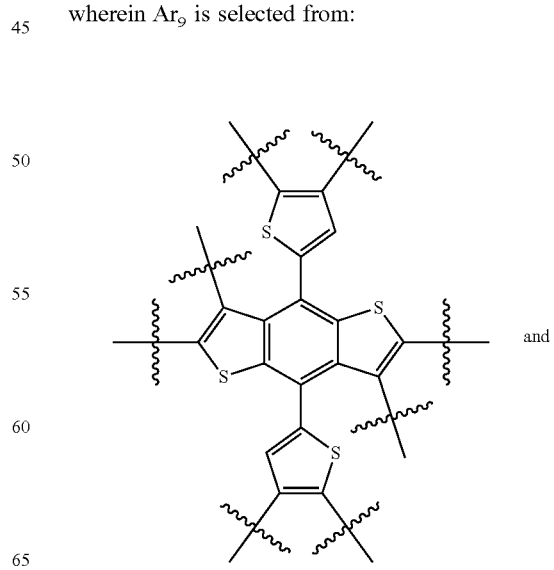
and -continued
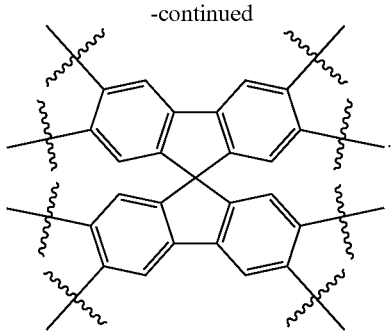
14. The molecular acceptor of claim 13 further selected from:
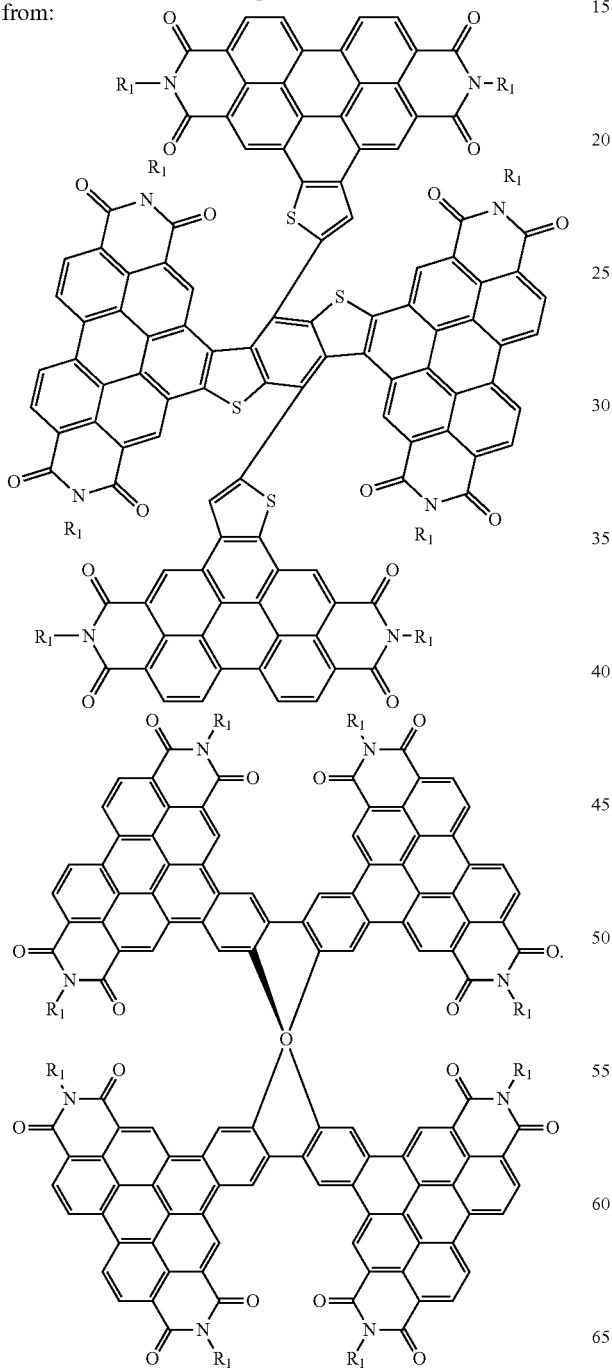

15. The molecular acceptor of claim 1 further selected from an acceptor of formula XI:
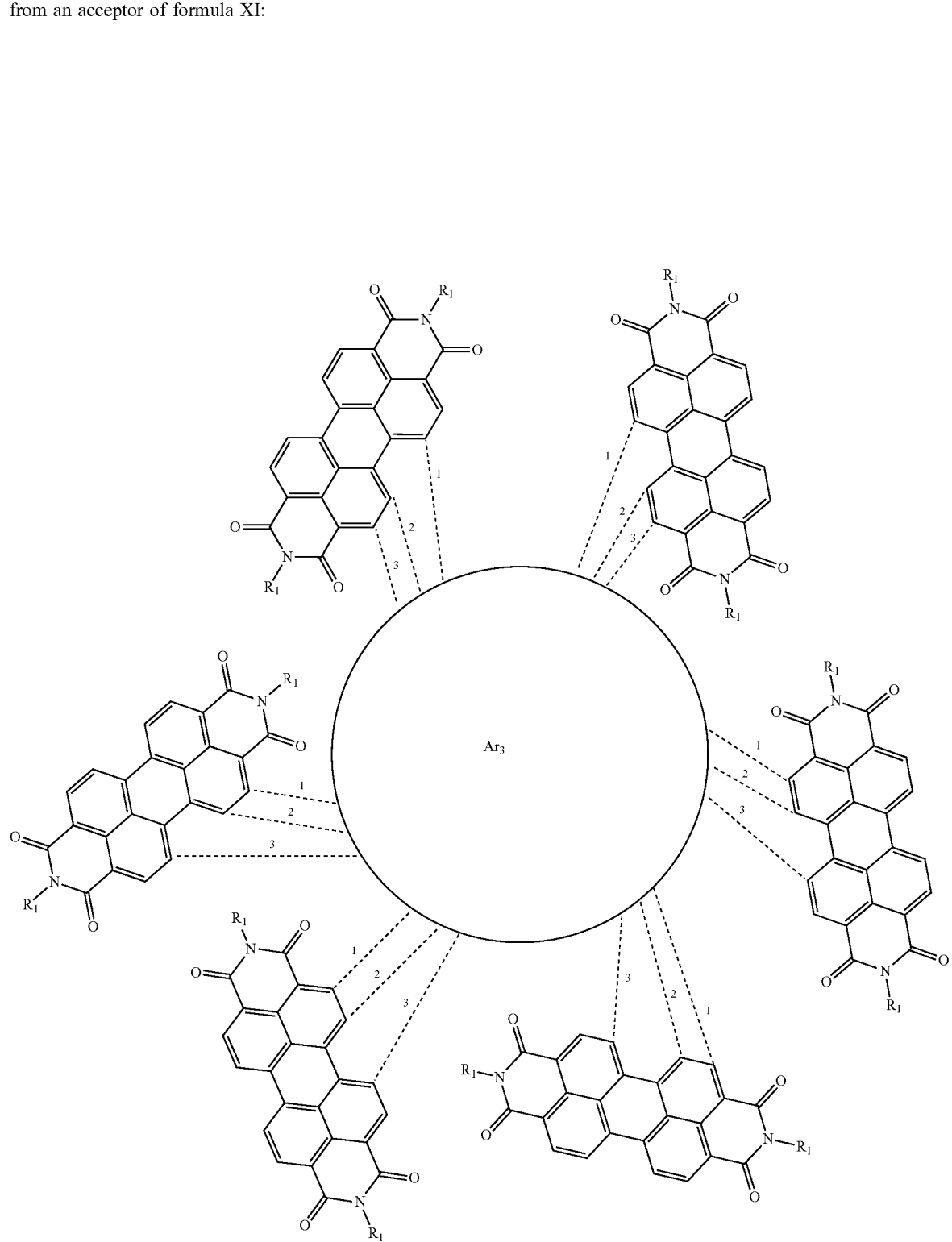

where R¹ is selected from: $C_1$-$C_{30}$ linear or branched chain alkyl; and
when $Ar_{10}$ is bonded at 1, $Ar_{10}$ is selected from:
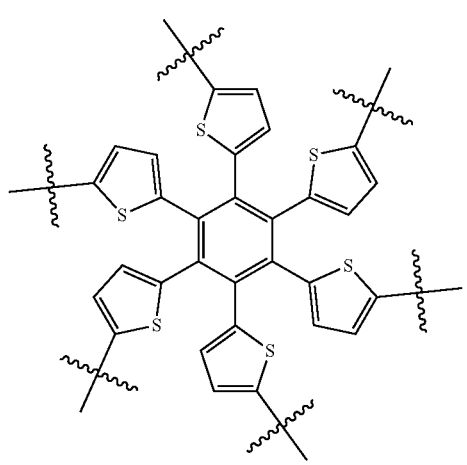
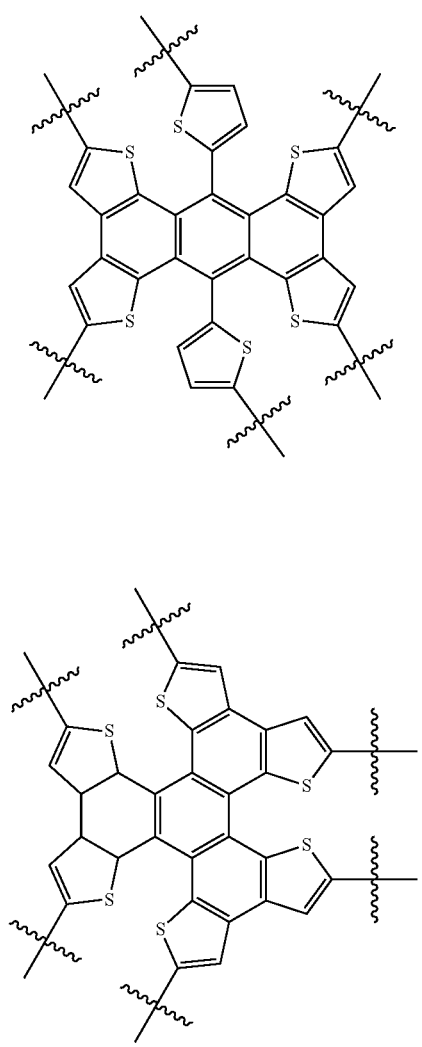
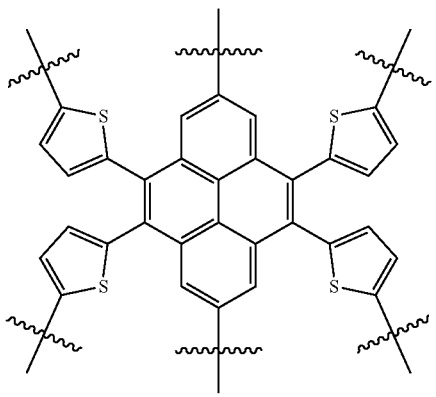
or when $Ar_{10}$ is bonded at 2 and 3, $Ar_{10}$ is:
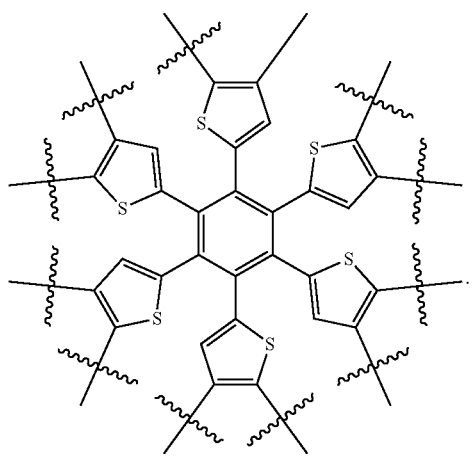 [SMILES: *c1cc(-c2c(-c3cc(*)c(*)s3)c(-c3cc(*)c(*)s3)c(-c3cc(CC)c(*)s3)c(-c3cc(*)c(*)s3)c2-c2cc(*)c(*)s2)sc1*]
16. A molecular acceptor of claim 15 further selected from an acceptor of formula IV:

131 132
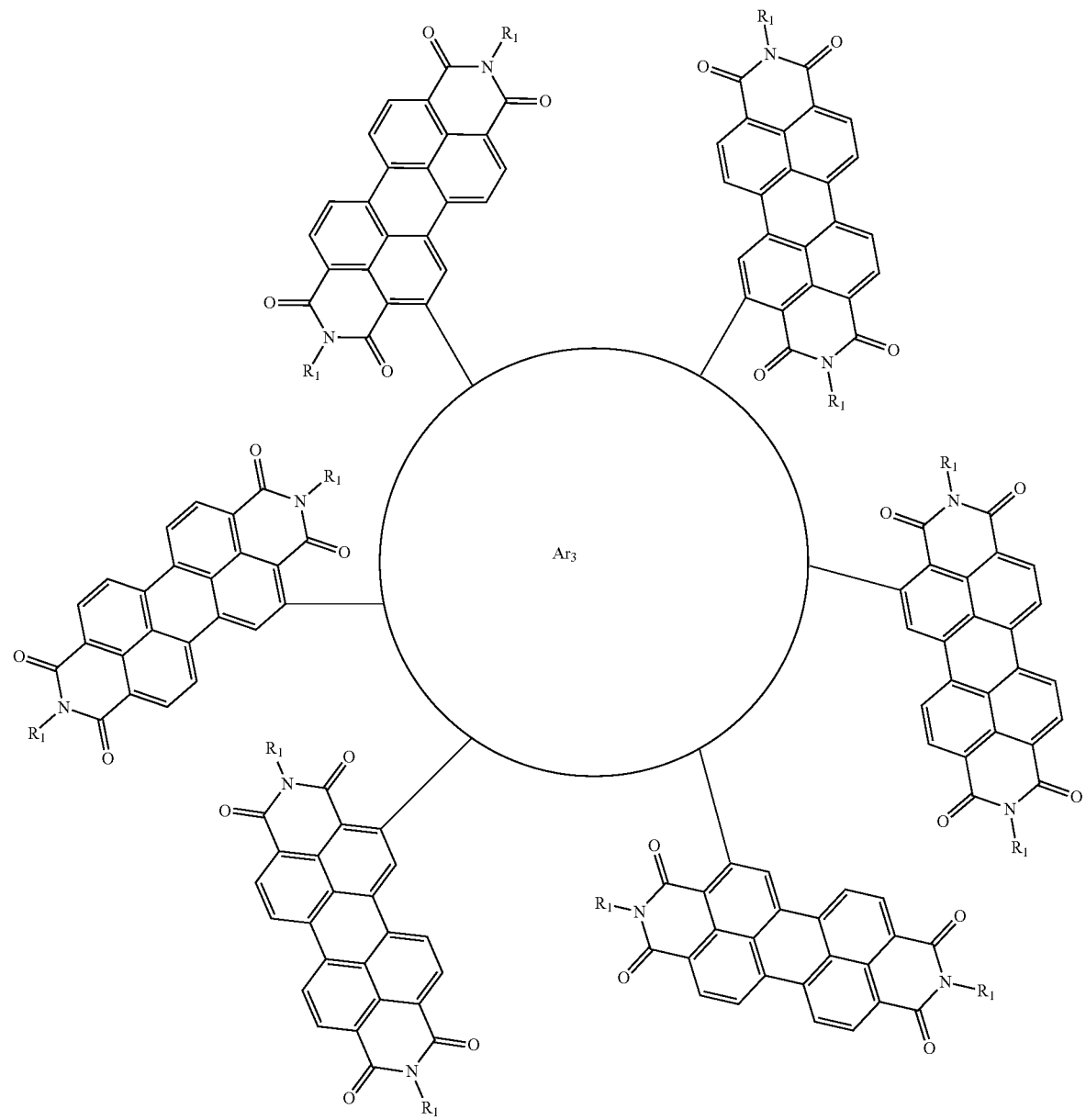

wherein $R^1$ is $C_1$-$C_{30}$ linear or branched chain alkyl; and $Ar^3$ is selected from the group consisting of:

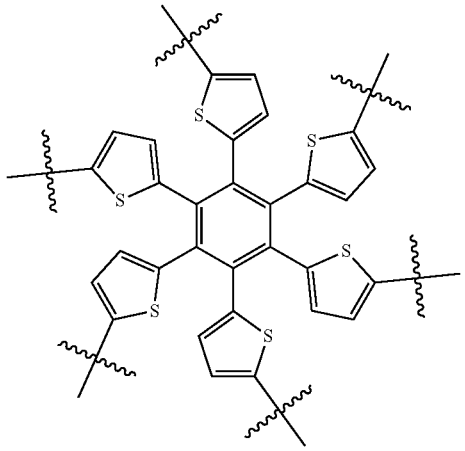

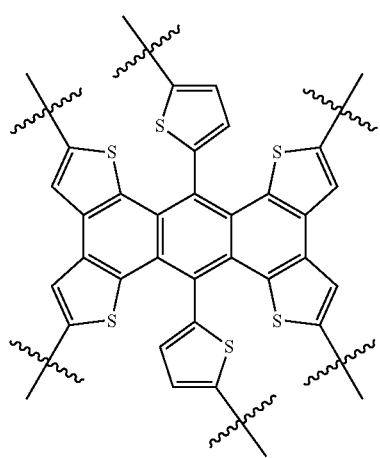

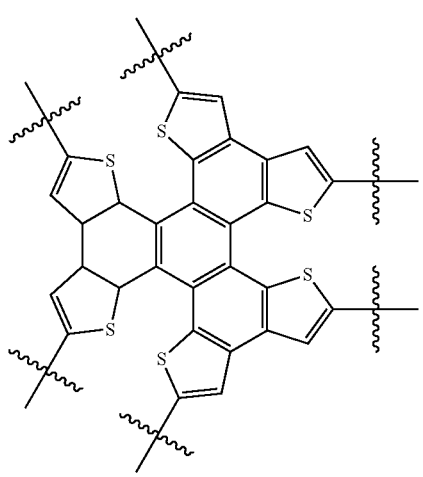

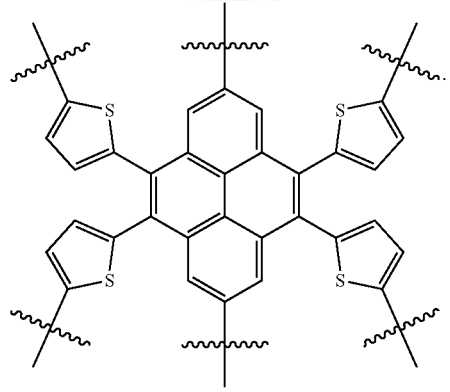

17. The molecular acceptor of claim 1, where $R^1$ and at least one of $R^2$, $R^3$, $R^4$, $R^5$, $R^6$, $R^7$, $R^8$, $R^9$, $R^{10}$ and $R^{11}$ is the same.

18. The molecular acceptor of claim 1, where $R^1$ and at least one of $R^2$, $R^3$, $R^4$, $R^5$, $R^6$, $R^7$, $R^8$, $R^9$, $R^{10}$ and $R^{11}$ is different.

19. The molecular acceptor of claim 1, where $R^1$ and at least one of $R^2$, $R^3$, $R^4$, $R^5$, $R^6$, $R^7$, $R^8$, $R^9$, $R^{10}$ and $R^{11}$ is 2-ethylhexyl.

20. The molecular acceptor of claim 1, where $R^1$ and at least one of $R^2$, $R^3$, $R^4$, $R^5$, $R^6$, $R^7$, $R^8$, $R^9$, $R^{10}$ and $R^{11}$ is 2-butyloctyl.

21. The semiconducting acceptor of claim 1, where $R^1$ and at least one of $R^2$, $R^3$, $R^4$, $R^5$, $R^6$, $R^7$, $R^8$, $R^9$, $R^{10}$ and $R^{11}$ is 1-propylbutyl.

22. A use of the semiconducting acceptor of claim 1 in a solar cell, an optical device, an electroluminescent device, a photovoltaic cell, a semiconducting cell, or photodiode.

23. A semiconducting polymer of formula VIII:

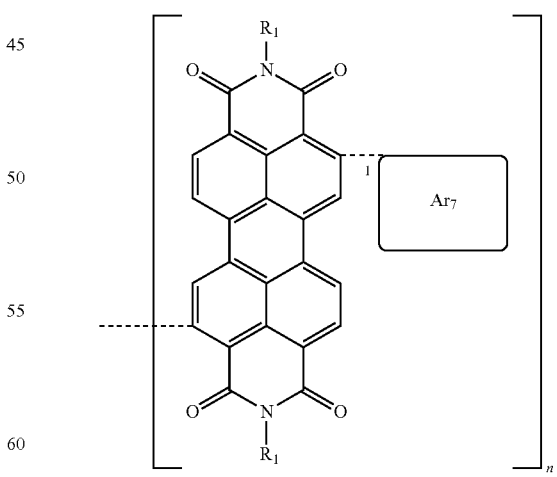

where $R^1$ is a selected from: $C_1$-$C_{30}$ linear or branched chain alkyl;

n is an integer greater than 1; and $Ar_7$ is selected from:
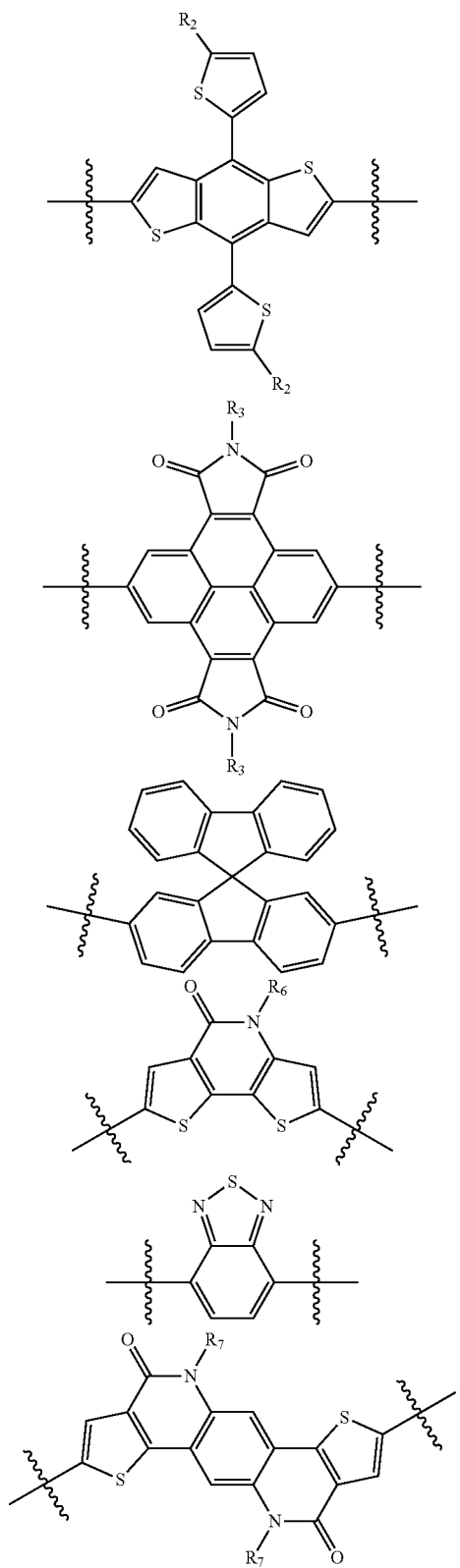
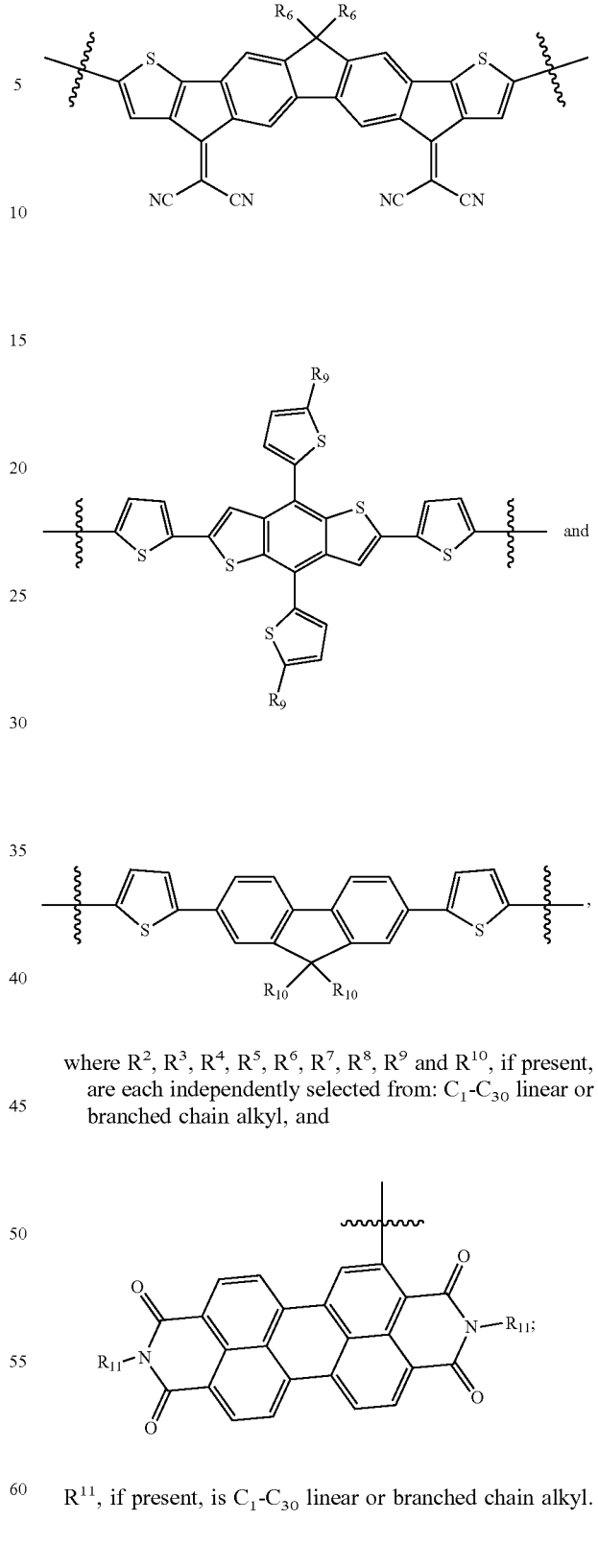
where $R^2$, $R^3$, $R^4$, $R^5$, $R^6$, $R^7$, $R^8$, $R^9$ and $R^{10}$, if present, are each independently selected from: $C_1$-$C_{30}$ linear or branched chain alkyl, and
$R^{11}$, if present, is $C_1$-$C_{30}$ linear or branched chain alkyl.
* * * * *

UNITED STATES PATENT AND TRADEMARK OFFICE
CERTIFICATE OF CORRECTION

PATENT NO. : 10,818,849 B2
APPLICATION NO. : 16/067501
DATED : October 27, 2020
INVENTOR(S) : Donglin Zhao et al.

Page 1 of 3

It is certified that error appears in the above-identified patent and that said Letters Patent is hereby corrected as shown below:

In the Claims

Column 125, Claim 14, delete the last compound, between Lines 42-65, and replace with

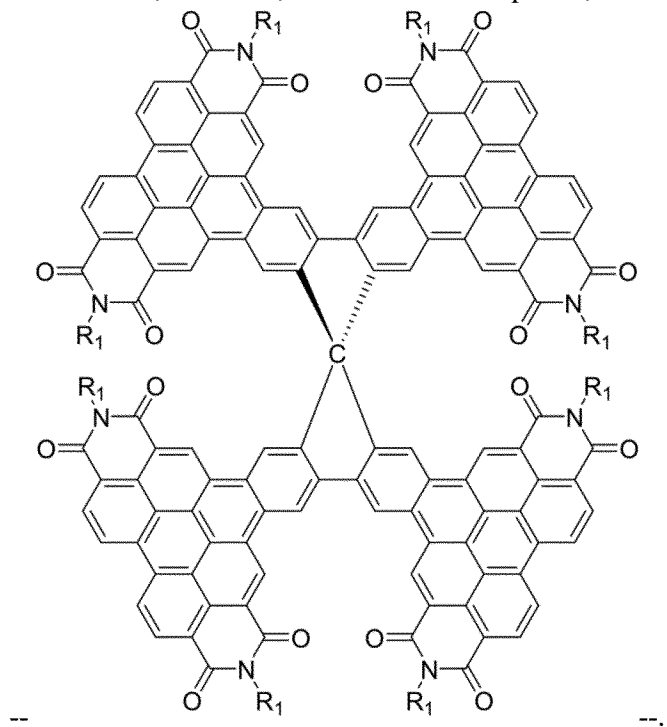

-- --.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,818,849 B2

Column 127, Claim 15, delete the chemical structure on Columns 127-128, and replace with

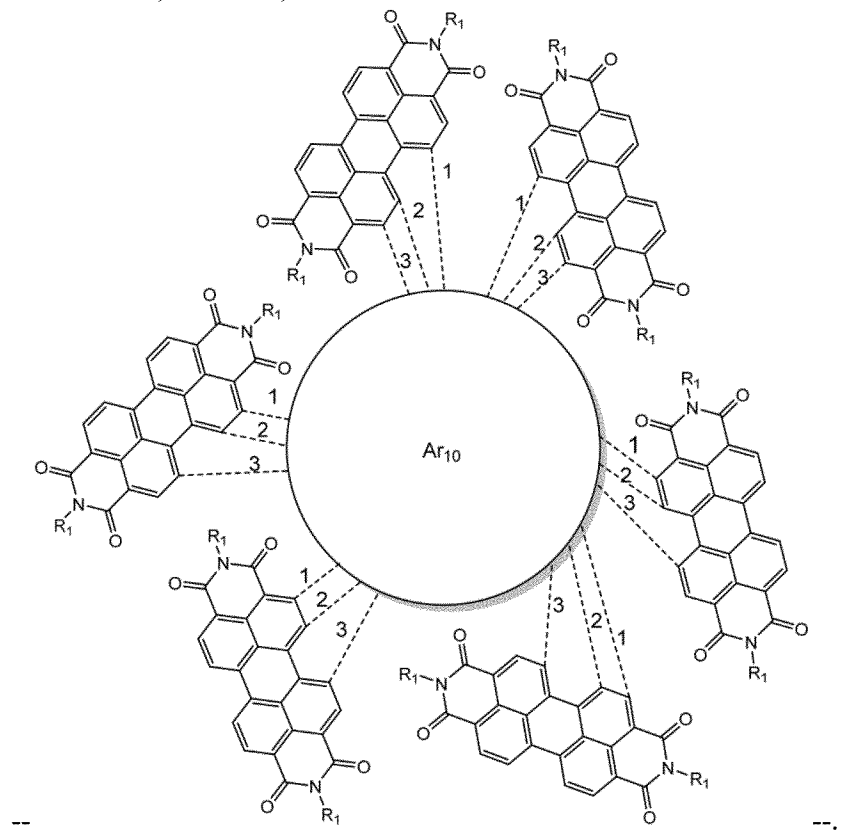

-- --.

Column 130, Claim 15, delete the second chemical structure down, between Lines 35-55,

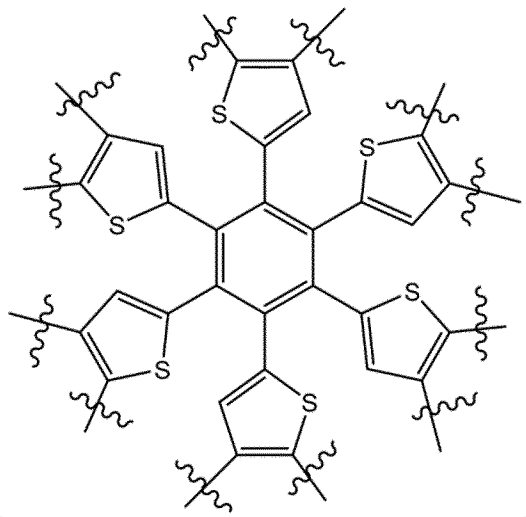

and replace with -- --.

CERTIFICATE OF CORRECTION (continued)

Column 136, Claim 23, delete the first chemical structure down, between Lines 1-10, and replace with -- 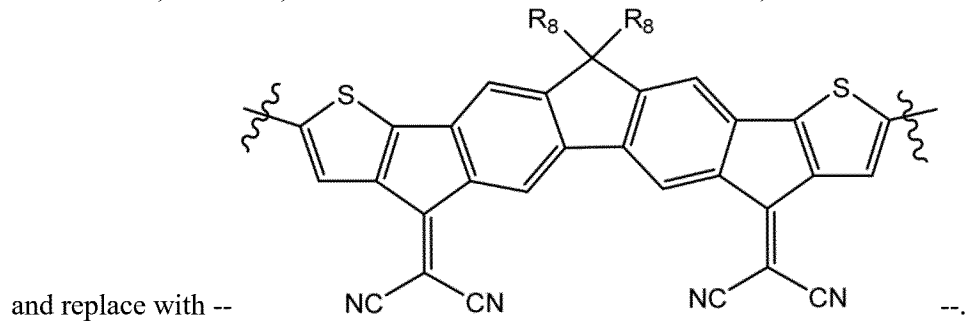 --.